US012590145B2

(12) United States Patent
Chen et al.

(10) Patent No.: US 12,590,145 B2
(45) Date of Patent: Mar. 31, 2026

(54) BI-SPECIFIC CHIMERIC ANTIGEN RECEPTOR

(71) Applicant: The Regents of the University of California, Oakland, CA (US)

(72) Inventors: Yvonne Yu-Hsuan Chen, Los Angeles, CA (US); Zenan Li Chang, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 696 days.

(21) Appl. No.: 17/323,568

(22) Filed: May 18, 2021

(65) Prior Publication Data

US 2021/0277099 A1 Sep. 9, 2021

Related U.S. Application Data

(62) Division of application No. 15/772,403, filed as application No. PCT/US2016/059444 on Oct. 28, 2016, now Pat. No. 11,014,980.

(60) Provisional application No. 62/248,685, filed on Oct. 30, 2015.

(51) Int. Cl.

| | |
|---|---|
| ***C07K 16/22*** | (2006.01) |
| ***A61K 38/00*** | (2006.01) |
| ***A61K 39/00*** | (2006.01) |
| ***A61K 40/11*** | (2025.01) |
| ***A61K 40/22*** | (2025.01) |
| ***A61K 40/31*** | (2025.01) |
| ***A61K 40/41*** | (2025.01) |
| ***A61K 40/42*** | (2025.01) |
| ***A61P 35/00*** | (2006.01) |
| ***A61P 37/02*** | (2006.01) |
| ***C07K 14/725*** | (2006.01) |
| ***C12N 5/0783*** | (2010.01) |
| ***G01N 33/50*** | (2006.01) |
| *A61K 35/00* | (2006.01) |

(52) U.S. Cl.

CPC .......... *C07K 16/22* (2013.01); *A61K 39/0008* (2013.01); *A61K 40/11* (2025.01); *A61K 40/22* (2025.01); *A61K 40/31* (2025.01); *A61K 40/416* (2025.01); *A61K 40/4211* (2025.01); *A61K 40/4229* (2025.01); *A61P 35/00* (2018.01); *A61P 37/02* (2018.01); *C07K 14/7051* (2013.01); *C12N 5/0636* (2013.01); *C12N 5/0637* (2013.01); *G01N 33/505* (2013.01); *A61K 35/00* (2013.01); *A61K 38/00* (2013.01); *C07K 2317/33* (2013.01); *C07K 2317/622* (2013.01); *C07K 2317/76* (2013.01); *C07K 2319/02* (2013.01); *C07K 2319/03* (2013.01); *C07K 2319/33* (2013.01); *C12N 2501/15* (2013.01); *C12N 2501/2302* (2013.01)

(58) Field of Classification Search

CPC .......................... C07K 16/22; C07K 14/7051; C07K 2317/33; A61K 39/0008; A61K 2039/5158

See application file for complete search history.

(56) References Cited

U.S. PATENT DOCUMENTS

| | | | |
|---|---|---|---|
| 4,797,368 | A | 1/1989 | Carter et al. |
| 5,138,941 | A | 8/1992 | Strauss |
| 5,139,941 | A | 8/1992 | Muzyczka |
| 5,670,373 | A | 9/1997 | Kishimoto |
| 5,821,337 | A | 10/1998 | Carter et al. |
| 6,319,494 | B1 | 11/2001 | Capon et al. |
| 7,151,169 | B2 | 12/2006 | Thompson et al. |
| 7,276,477 | B2 | 10/2007 | Osslund et al. |
| 7,479,543 | B2 | 1/2009 | Tsuchiya et al. |
| 7,741,465 | B1 | 6/2010 | Eshhar et al. |
| 8,012,482 | B2 | 9/2011 | Adams et al. |
| 8,063,182 | B1 | 11/2011 | Brockhaus et al. |
| 8,236,541 | B2 | 8/2012 | Black |
| 8,399,645 | B2 | 3/2013 | Campana et al. |
| 8,507,657 | B2 | 8/2013 | Nicolades et al. |
| 8,580,264 | B2 | 11/2013 | Zhang et al. |
| 9,447,194 | B2 | 9/2016 | Jensen |
| 9,464,140 | B2 | 10/2016 | June et al. |
| 9,518,123 | B2 | 12/2016 | June et al. |
| 9,540,445 | B2 | 1/2017 | June et al. |
| 9,834,590 | B2 | 12/2017 | Campana et al. |

(Continued)

FOREIGN PATENT DOCUMENTS

| | | |
|---|---|---|
| CN | 105837693 A | 8/2016 |
| CN | 107074957 A | 8/2016 |

(Continued)

OTHER PUBLICATIONS

Reverdatto et al.—Peptide aptamers: Development and Applications—Curr. Top. Med. Chem. 15, 1082-1101, 2015. (Year: 2015).*

(Continued)

*Primary Examiner* — Elly-Gerald Stoica
(74) *Attorney, Agent, or Firm* — Norton Rose Fulbright US LLP

(57) ABSTRACT

Aspects of the disclosure relate to polypeptides comprising a signal peptide, an antigen-binding domain that specifically binds TGF-β, a peptide spacer, a transmembrane domain, and an endodomain. When expressed in a cell, the polypeptides are capable of not only neutralizing the TGF-β but also specifically triggering T-cell activation in the presence of TGF-β. T-cell activation spurs the immune cell to produce immunostimulatory cytokines and proliferate, thus turning TGF-β from an immunosuppressive signal to an activating stimulus.

10 Claims, 16 Drawing Sheets

Specification includes a Sequence Listing.

(56) References Cited

U.S. PATENT DOCUMENTS

| | | | |
|---|---|---|---|
| 9,932,412 | B2 | 4/2018 | Kim et al. |
| 10,189,903 | B2 | 1/2019 | Jensen |
| 10,266,592 | B2 | 4/2019 | Jensen |
| 10,442,867 | B2 | 10/2019 | Orentas et al. |
| 10,697,749 | B1 | 6/2020 | June et al. |
| 10,736,918 | B2 | 8/2020 | Jensen et al. |
| 10,780,118 | B2 | 9/2020 | Jensen et al. |
| 10,829,556 | B2 | 11/2020 | Jensen |
| 10,869,889 | B2 | 12/2020 | Jensen et al. |
| 10,888,581 | B2 | 1/2021 | Wu et al. |
| 2004/0026871 | A1 | 2/2004 | Stephens et al. |
| 2004/0254774 | A1 | 12/2004 | Loh et al. |
| 2006/0135517 | A1 | 6/2006 | Lee et al. |
| 2006/0251658 | A1 | 11/2006 | Ledbetter et al. |
| 2007/0142376 | A1 | 6/2007 | Fleenor et al. |
| 2007/0237779 | A1 | 10/2007 | Ledbetter et al. |
| 2009/0068158 | A1 | 3/2009 | Medin et al. |
| 2010/0330676 | A1 | 12/2010 | Horowitz et al. |
| 2011/0008364 | A1 | 1/2011 | Ledbetter et al. |
| 2011/0286980 | A1 | 11/2011 | Brenner et al. |
| 2013/0071414 | A1 | 3/2013 | Dotti et al. |
| 2013/0280220 | A1 | 10/2013 | Ahmed et al. |
| 2014/0004132 | A1 | 1/2014 | Brenner et al. |
| 2014/0141000 | A1 | 5/2014 | Chiu et al. |
| 2014/0314760 | A1 | 10/2014 | Rosenblum et al. |
| 2015/0038684 | A1 | 2/2015 | Jensen |
| 2017/0333480 | A1 | 11/2017 | Cooper et al. |
| 2017/0342144 | A1 | 11/2017 | Wei et al. |
| 2017/0362582 | A1 | 12/2017 | Chen et al. |
| 2017/0368098 | A1 | 12/2017 | Chen et al. |
| 2018/0022815 | A1 | 1/2018 | Chang |
| 2018/0057608 | A1 | 3/2018 | Jung et al. |
| 2018/0125892 | A1 | 5/2018 | Brannetti et al. |
| 2018/0162939 | A1 | 6/2018 | Ma et al. |
| 2018/0230225 | A1 | 8/2018 | Fan et al. |
| 2018/0280433 | A1 | 10/2018 | Cooper et al. |
| 2018/0319862 | A1 | 11/2018 | Thompson et al. |
| 2019/0169289 | A1 | 6/2019 | Young et al. |
| 2019/0202937 | A1 | 7/2019 | Humphreys et al. |
| 2020/0071421 | A1 | 3/2020 | Zhou et al. |
| 2020/0108142 | A1 | 4/2020 | Wiltzius |
| 2020/0215108 | A1 | 7/2020 | Jensen |
| 2020/0246382 | A1 | 8/2020 | Perez et al. |
| 2020/0392200 | A1 | 12/2020 | Orentas et al. |
| 2021/0061879 | A1 | 3/2021 | Williams et al. |
| 2021/0309740 | A1 | 10/2021 | Jensen |

FOREIGN PATENT DOCUMENTS

| | | | |
|---|---|---|---|
| CN | 106414502 A | 2/2017 | |
| EP | 0610046 | 12/2005 | |
| EP | 1810980 | 7/2007 | |
| EP | 2330193 | 6/2011 | |
| EP | 1638510 | 9/2015 | |
| EP | 2445530 | 9/2016 | |
| EP | 3240805 | 11/2017 | |
| EP | 3443002 | 2/2019 | |
| EP | 3550020 | 10/2019 | |
| EP | 3661964 | 6/2020 | |
| EP | 3227323 | 8/2020 | |
| EP | 3730512 | 10/2020 | |
| EP | 2884999 | 11/2020 | |
| EP | 3732205 | 11/2020 | |
| EP | 3824905 | 5/2021 | |
| EP | 3006459 | 10/2021 | |
| EP | 3687553 | 1/2022 | |
| JP | 2003-501348 | 1/2003 | |
| JP | 2007-515949 | 6/2007 | |
| JP | 2008-529503 | 8/2008 | |
| JP | 2013-542179 | 11/2013 | |
| JP | 2015-513394 | 5/2015 | |
| WO | WO 1992/019759 | 11/1992 | |
| WO | WO 1994/012520 | 6/1994 | |
| WO | WO 98/50432 | 11/1998 | |
| WO | WO200066631 | * 9/2000 | ............ C07K 16/22 |
| WO | WO 2004/019990 | 3/2004 | |
| WO | WO200500200 | * 6/2005 | ............ G01N 33/50 |
| WO | WO 2005/097832 | 10/2005 | |
| WO | WO 2006/046661 | 5/2006 | |
| WO | WO2006086469 | * 8/2006 | ............ C07K 16/22 |
| WO | 2010065818 | 6/2010 | |
| WO | WO 2011/140170 | 11/2011 | |
| WO | WO 2012/030394 | 3/2012 | |
| WO | WO 2013/123061 | 8/2013 | |
| WO | WO 2014/072233 | 5/2014 | |
| WO | WO 2014/164709 | 10/2014 | |
| WO | WO 2014/172584 | 10/2014 | |
| WO | WO 2015/121454 | 8/2015 | |
| WO | 2016100232 | 6/2016 | |
| WO | WO 2016/094304 | 6/2016 | |
| WO | WO 2016/174652 | 11/2016 | |
| WO | WO 2017/075433 | 5/2017 | |
| WO | WO 2017/096329 | 6/2017 | |
| WO | WO 2017/172981 | 10/2017 | |
| WO | WO 2017222593 | 12/2017 | |
| WO | WO 2018/103502 | 6/2018 | |
| WO | WO 2018102795 | 6/2018 | |
| WO | WO 2019237022 | 12/2018 | |
| WO | WO 2019/134866 | 7/2019 | |
| WO | WO 2019/232444 | 12/2019 | |
| WO | WO 2019/242632 | 12/2019 | |
| WO | WO 2020/001344 | 1/2020 | |
| WO | WO 2020/010235 | 1/2020 | |
| WO | WO 2020/033272 | 2/2020 | |
| WO | WO 2020/070289 | 4/2020 | |
| WO | WO 2020/070290 | 4/2020 | |
| WO | WO 2020/097193 | 5/2020 | |
| WO | WO 2020/113188 | 6/2020 | |
| WO | WO 2020/172177 | 8/2020 | |
| WO | WO 2020/172641 | 8/2020 | |
| WO | WO 2020/181164 | 9/2020 | |
| WO | WO 2020/216238 | 10/2020 | |
| WO | WO 2020/232447 | 11/2020 | |
| WO | WO 2020/236792 | 11/2020 | |
| WO | WO 2020/253393 | 12/2020 | |
| WO | WO 2021/003739 | 1/2021 | |
| WO | WO 2021/027867 | 2/2021 | |
| WO | WO 2021/030586 | 2/2021 | |

OTHER PUBLICATIONS

Extended Search Report issued in Corresponding European Application No. 19/819799.8, dated Jan. 25, 2022.

Zah et al., Systematically optimized BCMA/CS1 bispecific CAR-T cells robustly control heterogeneous multiple myeloma; *Nature Communications*, vol. 11, No. 1 (2020).

Homach A et al., "An anti-CD30 chimeric receptor that mediates CD3-zeta-independent T-cell activation against Hodgkin's lymphoma cells in the presence of soluble CD30." *Cancer Research, American Association for Cancer Research, US*, vol. 58, No. 6, Mar. 15, 1998, pp. 1116-1119.

Lanitis, Evripidis et al. "Redirected Antitumor Activity of Primary Human Lymphocytes Transduced With a Fully Human Anti-mesothelin Chimeric Receptor", *Molecular Therapy*, vol. 20, No. 3, Mar. 1, 2012, pp. 633-643.

Ma Q. et al. "Carcinoembryonic antigen-immunoglobulin Fe fusion protein (CEA-Fe). For identification and activation of anti-CEA im-munoglobulin-T-cell receptor-modified cells, representative of a new class of Ig fusion proteins", *Cancer Gene Therapy*, vol. 11, Jan. 1, 2004, pp. 297-306.

Summons to attend oral proceedings pursuant to Rule 115(1) EPC issued in European Application No. 16860930.3 dated Oct. 13, 2021.

Westwood, "The Lewis-Y Carbohydrate Antigen is Expressed by Many Human Tumors and Can Serve as a Target for Genetically Redirected T cells Despite the Presence of Soluble Antigen in Serum." *Journal of Immunotherapy*, Apr. 1, 2009.

Yang, Zhi-Zhang et al. "Soluble and Membrane-Bound TGF- [beta]-Mediated Regulation of Intratumoral T Cell Differentiation and Function in B-Cell Non-Hodgkin Lymphoma", *PLoS ONE*, vol. 8, No. 3, Jan. 1, 2013, p. e59456.

(56) References Cited

OTHER PUBLICATIONS

Zhang, Cheng et al., "Engineering CAR-T cells." *Biomarker Research, Biomed Central Ltd, London, UK*, vol. 5, No. 1, Jun. 24, 2017, pp. 1-6.
Extended Search Report issued on Mar. 28, 2023 in European Application No. 22199829.7.
Office Action and Search Report issued on Oct. 12, 2022 in Chinese Application No. 201980053239.6.
Ramadoss, NS et al., An anti-B cell maturation antigen bispecific antibody for multiple myeloma. *J Am Chem Soc*; pp. 5288-5291; Apr. 15, 2015 (Abstract).
Final Rejection issued in corresponding Korean Application No. 10-2018-7015353, dated Jan. 15, 2024. (English Translation Provided).
Kershaw, M.H. et al., "Gene-engineered T cells for cancer therapy", *Nature Reviews: Cancer*, 13, pp. 525-541, 2013.
Pulè MA et al. A chimeric T cell antigen receptor that augments cytokine release and supports clonal expansion of primary human T cells. *Mol Ther*. Nov. 2005;12(5):933-41.
Ahmad et al., "scFv Antibody: Principles and Clinical Application," *Clin Dev Immunol*, 2012:980250, (2012).
Ali, et al., "T Cells Expressing an Anti-B-Cell Maturation Antigen Chimeric Antigen Receptor Cause Remissions of Multiple Myeloma," *Blood*, 128:1688-1700, 2016.
Bendle et al., "Blockade of TGF-β signaling greatly enhances the efficacy of TCR gene therapy of cancer." J. Immunol, 191(6):3232-3239, (2013).
Berdeja, et al., "First-In-Human Multicenter Study of bb2121 Anti-BCMA CAR T-Cell Therapy for Relapsed/Refractory Multiple Myeloma: Updated Results.," *Journal of Clinical Oncology*, 35(15 suppl):3010-3010, 2017.
Birchenough, et al., "Equity Research: Deep Dive on Emerging Cell Therapies for Cancer," Research Report Online Wells Fargo Securities, LLC Apr. 19, 2017, retrieved on Nov. 22, 2019 from the internet https://cdn2.hubspot.net/hubfs/4625168/%5B2017%5D%20Wells%20Fargo%20-%20Deep%20Dive%20on%20Emerging%20Cell%20Therapies.pdf 1-94, p. 37, 5th paragraph.
Blat et al., "Suppression of murine colitis and its associated cancer by carcinoembryonic antigen-specific regulatory T cells," Mol Ther, 22:1018-1028, (2014).
Boissel et al., "Retargeting NK-92 cells bty means of CD19-and CD20-specific chemieric antigen receptors compares favorably with antibody-dependent cellular cytotoxicity," *OncoImmunology*, 2(10):e26527, (2013).
Bollard et al., "Adapting a transforming growth factor B-related tumor protection strategy to enhance antitumor immunity." Blood, 99(9):3179-3187, (2002).
Bond & Butler, "Intracellular Proteases," *Annual Review of Biochemistry*, 56: 333-364, 1987.
Brentjens et al., "CD19-targeted T cells rapidly induce molecular remissions in adults with chemotherapy-refractory acute lymphoblastic leukemia", Sci. Transl. Med., 5:177ra138, (2013).
Brudno et al., "Toxicities of chimeric antigen receptor T cells: recognition and management," Blood, 127:3321-3330, (2016).
Brunstein et al., "Umbilical cord blood-derived T regulatory cells to prevent GVHD: kinetics, toxicity profile, and clinical effect," Blood, 127:1044-1051, (2016).
Brusko et al., "Human antigen-specific regulatory T cells generated by T cell receptor gene transfer", PLoS One, 5:e11726, (2010).
Budde et al., "Combining a CD20 chimeric antigen receptor and an inducible caspase 9 suicide switch to improve the efficacy and safety of T cell adoptive immunotherapy for lymphoma," *PloS One*, 8(12): e82742, (2013.
Carpenter, et al. B-cell Maturation Antigen Is a Promising Target for Adoptive Tcell Therapy of Multiple Myeloma, *Clinical Cancer Research*, 19(8): 2048-2060, 2013.
Chang et al., "Rewiring T-cell responses to soluble factors with chimeric antigen receptors," Nat. Chem. Biol., 2018, 14(3):317-324.
Chen et al, "Fusion protein linkers: Property, design and functionality", Advanced Drug Delivery Reviews, vol. 65, (2003), pp. 1357-1369.
Chen, et al., "A Unique Substrate Recognition Profile for Matrix Metalloproteinase-2," *The Journal of Biological Chemistry*, 277(6): 4485-4491, 2002.
Chen, et al., "A Compound Chimeric Antigen Receptor Strategy For Targeting Multiple Myyeloma," *Leukemia*, 32(2):402-412, 2018.
Chmielewski, et al., "IL-12 Release by Engineered T Cells Expressing Chimeric Antigen Receptors Can Effectively Muster an Antigen-Independent Macrophage Response on Tumor Cells That Have Shut Down Tumor Antigen Expression," Cancer Research, 71(17): 5697-5706, 2011.
Chu, "Genetic Modification of T Cells Redirected toward CS1 Enhances Eradication of Myeloma Cells," *Clinical Cancer Research*, 20(15):3989-4000, 2014.
Chu, et al., "CS1-Specific Chimeric Antigen Receptor (CAR)-Engineered Natural Killer Cells Enhance In Vitro and In Vivo Antitumor Activity Against Human Multiple Myeloma," *Leukemia*, 28: 917-927, 2014.
Cohen, et al., "B-Cell Maturation Antigen (BCMA) Specific Chimeric Antigen Receptor T Cells (CART-BCMA) for Multiple Myeloma (MM): Initial Safety and Efficacy From a Phase I Study," *Blood*, 128:1147, 2016.
Corrigan-Curay et al., T-Cell Immunotherapy: Looking forward. Mol. Ther., 22, 1564-1574, 2014.
Dalken, et al., "Targeted Induction of Apoptosis by Chimeric Granzyme B Fusion Proteins Carrying Antibody and Growth Factor Domains for Cell Recognition," *Cell Death Differentiation*, 13, pp. 576-585. (2006).
Davila et al., "Efficacy and toxicity management of 19-28z CAR T cell therapy in B cell acute lymphoblastic leukemia.", Sci. Transl. Med., 6:224ra225, (2014).
Dotti et al., "Design and development of therapies using chimeric antigen receptor-expressing T-cells", Immunological Reviews, 257:107-126, (2014).
Duebner, et al., "Reprogramming Control of an Allosteric Signaling Switch Through Modular Recombination," *Science*, 301(5641), pp. 1904-1908. (2003).
Duffy, M.J., "Proteases as Prognostic Markers in Cancer," *Clinical Cancer Research*, 2: 613-618, 1996.
Dull et al., "A Third-Generataion Lentivirus Vector with a Conditional Packaging System," *J. Virol*, 72(11):8463-8471, (1998).
Ellebrecht et al., "Reengineering chimeric antigen receptor T cells for targeted therapy of autoimmune disease," Science, 353:179-184, (2016).
Extended European Search Report Issued in Corresponding European Patent Application No. 16860930.3, dated Oct. 9, 2019.
Extended European Search Report Issued in Corresponding European Patent Application No. 17845645.5, dated Mar. 24, 2020.
Extended European Search Report Issued in Corresponding European Application 15870819.8, dated Apr. 13, 2018.
Foster et al., "Antitumor activity of EBC-specific T lymphocytes transduced with a dominant negative TGF-β receptor," *J. Immunother*., 31(5):500-505, (2008).
Gogishvili, et al., "SLAMF7-CAR T Cells Eliminate Myeloma and Confer Selective Fratricide of SLAMF7+ Normal Lymphocytes," *Blood*, 130: 2838-2847, 2017.
Gorelik and Flavell, "Immune-mediated eradication of tumors through the blockade of transforming growth factor-β signaling in T cells" *Nat. Med*., 7:1118-1122 (2001).
Hay, "SUMO-Specific Proteases: A Twist in the Tail," *Trends in Cell Biology*, 17(8): 370-376, 2007.
Hillerdal et al., "Chimeric antigen receptor-engineered T cells for the treatment of metastatic prostate cancer," BioDrugs, 29:75-89, (2015).
Ho, et al., "Covert Cancer Therapeutics: Engineering T Cells to Interrogate Intracellular Tumor Antigens," 2015 AlChE Annual Meeting, Nov. 12, 2015, Salt Lake City, UT. (Abstract Only).
Ho, et al., "Modularly Constructed Synthetic Granzyme B Molecule Enables Interrogation of Intracellular Proteases for Targeted Cytotoxicity," ACS Synthetic Biology, 6, pp. 1484-1495. (2017).

(56) References Cited

OTHER PUBLICATIONS

International Preliminary Report on Patentability Issued in Corresponding PCT Patent Application No. PCT/US2019/036731, dated Dec. 15, 2020.
International Search Report and Written Opinion Issued in Corresponding PCT Application No. PCT/US2015/065623, mailed Apr. 19, 2016.
International Search Report and Written Opinion Issued in Corresponding PCT Patent Application No. PCT/US2019/036731, dated Dec. 27, 2019.
International Search Report and Written Opinion issued in International Application No. PCT/US2016/059444, dated Feb. 14, 2017.
International Search Report and Written Opinion issued in International Patent Application No. PCT/IB2017/055281, dated Mar. 8, 2018.
International Search Report and Written Opinion Issued in International Application No. PCT/US2015/065620, dated Mar. 28, 2016.
Kalos et al., "T cells with chimeric antigen receptors have potent antitumor effects and can establish memory in patients with advanced leukemia," Sci. Transl. Med., 3(95):95ra73, (2011).
Kelchtermans et al., "Activated CD4+CD25+ regulatory T cells inhibit osteoclastogenesis and collagen-induced arthritis", Ann. Rheum. Dis., 68:744-750, (2009).
Kelchtermans et al., "Defective CD4+CD25+ regulatory T cell functioning in collagen- induced arthritis: an important factor in pathogenesis, counter-regulated by endogenous IFN-gamma", Arthritis Res. Ther., 7:R402-415, (2005).
Kessenbrock, et al., "Matrix Metalloproteinases: Regulators of the Tumor Microenvironment," *Cell*, 141(1): 52-67, 2010.
Kochenderfer et al., "B-cell depletion and remissions of malignancy along with cytokine-associated toxicity in a clinical trial of anti-CD19 chimeric-antigen-receptor-transduced T cells", Blood, 119:2709-2720, (2012).
Le Gall et al., "Effect of linker sequences between the antibody variable domains on the formation, stability and biological activity of a bispecific tandem diabody" *Protein Engineering, Design & Selection* 2004, 17(4), 357-366.
Le Gall et al., "Immunosuppressive properties of anti-CD3 single-chain Fv and diabody" *Journal of Immunological Methods* 2004, 285, 111-127.
Lee et al., "Current concepts in the diagnosis and management of cytokine release syndrome," Blood, 124:188-195, (2014).
Lee, et al., "An APRIL-Based Chimeric Antigen Receptor for Dual Targeting of BCMA and TACI in Multiple Myeloma," *Blood*, 131:746-758, 2018.
Lopez-Otin & Matrisian, "Emerging Roles of Proteases in Tumour Suppression," *Nature*, 7: 800-808, 2007.
Malakhov, et al., SUMO Fusions and SUMO-Specific Protease for Efficient Expression and Purification of Proteins, *Journal of Structural and Functional Genomics*, 5(1-2). (2004).
Maude, et al., "Managing Cytokine Release Syndrome Associated with Novel T Cell-Engaging Therapies," The Cancer Journal, 20(2): 119-122, 2014.
Morgan et al., "Effective treatment of collagen-induced arthritis by adoptive transfer of CD25+ regulatory T cells," Arthritis Rheum, 52:2212-2221, (2005).
Myasoedova et al., "Is the incidence of rheumatoid arthritis rising?: results from Olmsted County, Minnesota, 1955-2007", Arthritis Rheum, 62-1576-1582, (2010).
Nakamura et al., "TGF-beta 1 plays an important role in the mechanism of CD4+CD25+ regulatory T cell activity in both humans and mice," J Immunol, 164:183-190, (2004).
Office Action Issued in Corresponding Japanese Patent Application No. 2018-522004, dated Oct. 12, 2020.
Office Action Issued in Corresponding U.S. Appl. No. 15/772,403, dated Apr. 9, 2020.
Office Action Issued in Corresponding U.S. Appl. No. 15/772,403, dated Oct. 8, 2020.
Partial Search Report issued in Corresponding European Patent Application No. 16860930, dated Jun. 26, 2019.
Pastan, et al., "Immunotoxin Treatment of Cancer," Annual Review of Medicine, 58, pp. 221-237. (2007).
Patel, et al., "Cancer CARtography: Charting Out a New Approach to Cancer Immunotherapy," 6(6): 675-678, 2014.
Porter et al., "Chimeric antigen receptor-modified T cells in chronic lymphoid leukemia," N. Engl. J. Med., 365:725-733, (2011).
Qin et al, "Preclinical Development of Bivalent Chimeric Antigen Receptors Targeting Both CD19 and CD22", *Molecular Therapy: Oncolytics*, vol. 11, Dec. 21, 2018, pp. 127-137.
Qin et al, "Supplemental Information. Preclinical Development of Bivalent Chimeric Antigen Receptors Targeting Both CD19 and CD22", *Molecular Therapy: Oncolytics*, vol. 11, 2018.
Quatromoni et al., "T cell receptor (TCR)-transgenic CD8 lymphocytes rendered insensitive to transforming growth factor beta (TGFβ) signaling mediate superior tumor regression in an animal model of adoptive cell therapy" J. Transl. Med., 10:127, (2012).
Rosenberg, "Finding suitable targets is the major obstacle to cancer gene therapy", Cancer Gene Ther., 21:45-47, (2017).
Rosenzweig, et al., "Preclinical Data Support Leveraging CS1 Chimeric Antigen Receptor T-Cell Therapy For Systemic Light Chain Amyloidosis," *Cytotherapy*, 19(7):861-866, 2017.
Stahnke, et al., "Granzyme B-H22 (scFv), a Human Immunotoxin Targeting CD64 in Acute Myeloid Leukemia in Monocytic Subtypes," *Molecular Cancer Therapeutics*, 7(9), pp. 2924-2932. (2008).
Stone et al., "A sensitivity scale for targeting T cells with chimeric antigen receptors (CARs) and bispecific T-cell engagers (BiTEs)" *Oncoimmunology*, 1(6):863-873, (2012).
Suarez, et al., "Chimeric Antigen Receptor T Cells Secreting Anti-PD-L1 Antibodies More Effectively Regress Renal Cell Carcinoma in a Humanized Mouse Model," Oncotarget, 7(23): 34341-34355, 2016.
Supplementary European Search Report issued in European Patent Application No. 15870818, dated Apr. 10, 2018.
Szymczak-Workman et al., "Design and construction of 2A peptide-linked multicistronic vectors," *Cold Spring Harbor Protocols*, 2012(2):199-204, (2012).
Tang et al., "Regulatory T-cell therapy in transplantation: moving to the clinic", Cold Spring Harbor Perspectives in Medicine, 3:a015552, (2013).
Thornberry, et al., "A Combinatorial Approach Defines Specificities of Members of the Caspase Family and Granzyme B," *The Journal of Biological Chemistry*, 272(29): 17907-17911, 1997.
Thornton et al., "Suppressor effector function of CD4+CD25+ immunoregulatory T cells is antigen nonspecific", J Immunol, 164:183-190, (2000).
Wang, et al., "Lenalidomide Enhances the Function of CS1 Chimeric Antigen Receptor-Redirected T Cells Against Multiple Myeloma," *Clinical Cancer Research*, 24(1):106-119, 2018.
Widdifield et al., "The epidemiology of rheumatoid arthritis in Ontario, Canada." Arthritis Rheumatol, 66:786-793 (2014).
Wright et al., "Adoptive therapy with redirected primary regulatory T cells results in antigen-specific suppression of arthritis," Proc. Natl. Acad. Sci. USA, 106(45):19078-19083, (2009).
Wright et al., "Regulatory T-cell adoptive immunotherapy: potential for treatment of autoimmunity", Expert Rev. Clin. Immunol., 7:213-225, (2011).
Wu et al., "FOXP3 controls regulatory T cell function through cooperation with NFAT", Cell, 126:375-387, (2006).
Wyatt, et al., "Human Telomerase Reverse Transcriptase (hTERT) Q169 Is Essential for Telomerase Function In Vitro and In Vivo," *PLoS One*, 4(9), pp. 1-14. (2009).
Yingling et al., "Development of TGF-β signalling inhibitors for cancer therapy" Nat. Rev. Drug Discov., 3:1011-1022 (2004).
Zhang et al., "Adoptive Transfer of Tumor-Reactive Transforming Growth Factor-β-Insensitive CD8+ T Cells" Cancer Res. 65(5):1761-1769. (2005).
Zhang et al., "Inhibition of TGF-β signaling in genetically engineered tumor antigen-reactive T cells significantly enhances tumor treatment efficacy," Gene Ther., 20:575-580, (2012).

(56) References Cited

OTHER PUBLICATIONS

Zhao, et al., "Secreted Antibody/Granzyme B Fusion Protein Stimulates Selective Killing of HER2-Overexpressing Tumor Cells," *The Journal of Biological Chemistry*, 279(20), pp. 21343-21348. (2004).

* cited by examiner

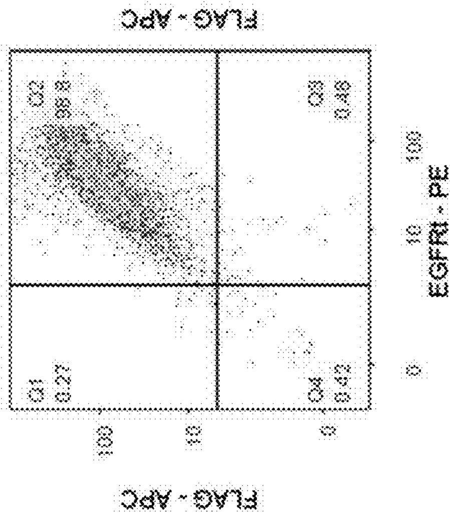
CD8+
FIG. 2
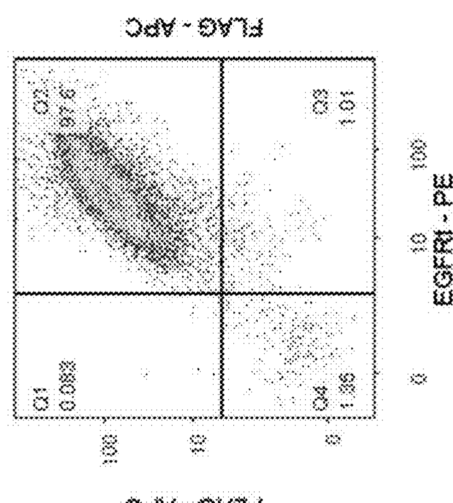
CD4+

SEQUENCE LISTING

```
<160> NUMBER OF SEQ ID NOS: 101

<210> SEQ ID NO 1
<211> LENGTH: 124
<212> TYPE: PRT
<213> ORGANISM: Artificial Sequence
<220> FEATURE:
<223> OTHER INFORMATION: Synthetic Peptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Lys Gly Leu Glu Trp Val
        35                  40                  45

Gly Val Ile Asn Pro Gly Ser Gly Gly Ser Asn Tyr Asn Glu Lys Phe
    50                  55                  60

Lys Gly Arg Ala Thr Ile Ser Ala Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Gly Phe Tyr Phe Asp Tyr Trp Gly Gln Gly Thr Leu
            100                 105                 110

Val Thr Val Ser Ser Ala Ser Thr Lys Gly Pro Ser
        115                 120


<210> SEQ ID NO 2
<211> LENGTH: 116
<212> TYPE: PRT
<213> ORGANISM: Artificial Sequence
<220> FEATURE:
<223> OTHER INFORMATION: Synthetic Peptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Leu Tyr Ser
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys His Gln
                85                  90                  95
```

```
Tyr Leu Ser Ser Asp Thr Phe Gly Gln Gly Thr Lys Val Glu Ile Lys
            100                 105                 110

Arg Thr Val Ala
        115


<210> SEQ ID NO 3
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Val Ile Ser Trp Val Arg Gln Ala Pro Gly Gln Gly Leu Glu Trp Met
        35                  40                  45

Gly Gly Val Ile Pro Ile Val Asp Ile Ala Asn Tyr Ala Gln Arg Phe
    50                  55                  60

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Leu Pro Arg Ala Phe Val Leu Asp Ala Met Asp Tyr Trp Gly Gln
            100                 105                 110

Gly Thr Leu Val Thr Val Ser Ser
        115                 120


<210> SEQ ID NO 4
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 4

Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Arg Leu Glu Ile Lys
            100                 105


<210> SEQ ID NO 5
<211> LENGTH: 10
<212> TYPE: PRT
<213> ORGANISM: Artificial Sequence
<220> FEATURE:
<223> OTHER INFORMATION: Synthetic Peptide
```

<400> SEQUENCE: 5

Gly Tyr Ala Phe Thr Asn Tyr Leu Ile Glu
1 5 10

<210> SEQ ID NO 6
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 6

Val Ile Asn Pro Gly Ser Gly Gly Ser Asn Tyr Asn Glu Lys Phe Lys
1 5 10 15

Gly

<210> SEQ ID NO 7
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 7

Ser Gly Gly Phe Tyr Phe Asp Tyr
1 5

<210> SEQ ID NO 8
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 8

Arg Ala Ser Gln Ser Val Leu Tyr Ser Ser Asn Gln Lys Asn Tyr Leu
1 5 10 15

Ala

<210> SEQ ID NO 9
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 9

Trp Ala Ser Thr Arg Glu Ser
1 5

<210> SEQ ID NO 10
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 10

His Gln Tyr Leu Ser Ser Asp Thr
1 5

<210> SEQ ID NO 11
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 11

Ser Asn Val Ile Ser
1 5

<210> SEQ ID NO 12
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 12

Gly Val Ile Pro Ile Val Asp Ile Ala Asn Tyr Ala Gln Arg Phe Lys
1 5 10 15

Gly

<210> SEQ ID NO 13
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 13

Pro Arg Ala Phe Val Leu Asp Ala Met Asp Tyr
1 5 10

<210> SEQ ID NO 14
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 14

Arg Ala Ser Gln Ser Leu Gly Ser Ser Tyr Leu Ala
1 5 10

<210> SEQ ID NO 15
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 15

Gly Ala Ser Ser Arg Ala Pro
1 5

<210> SEQ ID NO 16
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 16

Gln Gln Tyr Ala Asp Ser Pro Ile Thr
1 5

<210> SEQ ID NO 17
<211> LENGTH: 8
<212> TYPE: PRT

<213> ORGANISM: Artificial Sequence
<220> FEATURE:
<223> OTHER INFORMATION: Synthetic Peptide

<400> SEQUENCE: 17

Asp Tyr Lys Asp Asp Asp Asp Lys
1               5

<210> SEQ ID NO 18
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 18

Met Glu Thr Asp Thr Leu Leu Leu Trp Val Leu Leu Leu Trp Val Pro
1               5                   10                  15

Gly Ser Thr Gly
            20

<210> SEQ ID NO 19
<211> LENGTH: 123
<212> TYPE: PRT
<213> ORGANISM: Artificial Sequence
<220> FEATURE:
<223> OTHER INFORMATION: Synthetic Peptide

<400> SEQUENCE: 19

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Tyr Ser
            100                 105                 110

Trp Gly Gln Gly Thr Thr Val Thr Val Ser Ser
        115                 120

<210> SEQ ID NO 20
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 20

Glu Ile Val Leu Thr Gln Ser Pro Ser Ser Leu Ser Ala Ser Val Gly
1               5                   10                  15

Asp Arg Val Thr Ile Thr Cys Arg Ser Ser Gln Gly Ile Gly Asp Asp
            20                  25                  30

Leu Gly Trp Tyr Gln Gln Lys Pro Gly Lys Ala Pro Ile Leu Leu Ile
        35                  40                  45

Tyr Gly Thr Ser Thr Leu Gln Ser Gly Val Pro Ser Arg Phe Ser Gly

```
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Leu Gln Asp Ser Asn Tyr Pro Leu
                85                  90                  95

Thr Phe Gly Gly Gly Thr Arg Leu Glu Ile Lys
            100                 105


<210> SEQ ID NO 21
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 21

Ser Tyr Gly Met His
1               5


<210> SEQ ID NO 22
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 22

Val Ile Ser Tyr Asp Gly Ser Ile Lys Tyr Tyr Ala Asp Ser Val Lys
1               5                   10                  15

Gly


<210> SEQ ID NO 23
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 23

Thr Gly Glu Tyr Ser Gly Tyr Asp Thr Asp Pro Gln Tyr Ser
1               5                   10


<210> SEQ ID NO 24
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 24

Arg Ser Ser Gln Gly Ile Gly Asp Asp Leu Gly
1               5                   10


<210> SEQ ID NO 25
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 25

Gly Thr Ser Thr Leu Gln Ser
1               5
```

<210> SEQ ID NO 26
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 26

Leu Gln Asp Ser Asn Tyr Pro Leu Thr
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 27

Asp Lys Thr His Thr
1               5

<210> SEQ ID NO 28
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 28

Cys Pro Pro Cys
1

<210> SEQ ID NO 29
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 29

Cys Pro Glu Pro Lys Ser Cys Asp Thr Pro Pro Pro Cys Pro Arg
1               5                   10                  15

<210> SEQ ID NO 30
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 30

Glu Leu Lys Thr Pro Leu Gly Asp Thr Thr His Thr
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 31

Lys Ser Cys Asp Lys Thr His Thr Cys Pro
1               5                   10

<210> SEQ ID NO 32

<211> LENGTH: 7
<212> TYPE: PRT
<213> ORGANISM: Artificial Sequence
<220> FEATURE:
<223> OTHER INFORMATION: Synthetic Peptide

<400> SEQUENCE: 32

Lys Cys Cys Val Asp Cys Pro
1 5

<210> SEQ ID NO 33
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 33

Lys Tyr Gly Pro Pro Cys Pro
1 5

<210> SEQ ID NO 34
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 34

Glu Pro Lys Ser Cys Asp Lys Thr His Thr Cys Pro Pro Cys Pro
1 5 10 15

<210> SEQ ID NO 35
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 35

Glu Arg Lys Cys Cys Val Glu Cys Pro Pro Cys Pro
1 5 10

<210> SEQ ID NO 36
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 36

Glu Leu Lys Thr Pro Leu Gly Asp Thr Thr His Thr Cys Pro Arg Cys
1 5 10 15

Pro

<210> SEQ ID NO 37
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 37

Ser Pro Asn Met Val Pro His Ala His His Ala Gln
1 5 10

<210> SEQ ID NO 38
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 38

```
Glu Pro Lys Ser Cys Asp Lys Thr Tyr Thr Cys Pro Pro Cys Pro
1               5                   10                  15
```

<210> SEQ ID NO 39
<211> LENGTH: 45
<212> TYPE: PRT
<213> ORGANISM: Artificial Sequence
<220> FEATURE:
<223> OTHER INFORMATION: Synthetic Peptide

<400> SEQUENCE: 39

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

<210> SEQ ID NO 40
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(4)
<223> OTHER INFORMATION: Repeated more than once

<400> SEQUENCE: 40

```
Gly Ser Gly Gly Ser
1               5
```

<210> SEQ ID NO 41
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(4)
<223> OTHER INFORMATION: Repeated more than once

<400> SEQUENCE: 41

```
Gly Gly Gly Ser
1
```

<210> SEQ ID NO 42
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 42

```
Gly Gly Ser Gly
1
```

<210> SEQ ID NO 43
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 43

Gly Gly Ser Gly Gly
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 44

Gly Ser Gly Ser Gly
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 45

Gly Ser Gly Gly Gly
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 46

Gly Gly Gly Ser Gly
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 47

Gly Ser Ser Ser Gly
1               5

<210> SEQ ID NO 48
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 48

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 49
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 49

```
Leu Gly Leu Leu Val Ala Gly Val Leu Val Leu Leu Val Ser Leu Gly
1               5                   10                  15

Val Ala Ile His Leu Cys Cys
            20
```

<210> SEQ ID NO 50
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 50

```
Ala Leu Ile Val Leu Gly Gly Val Ala Gly Leu Leu Leu Phe Ile Gly
1               5                   10                  15

Leu Gly Ile Phe Phe Cys Val Arg Cys
            20                  25
```

<210> SEQ ID NO 51
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 51

```
Leu Cys Tyr Leu Leu Asp Gly Ile Leu Phe Ile Tyr Gly Val Ile Leu
1               5                   10                  15

Thr Ala Leu Phe Leu Arg Val
            20
```

<210> SEQ ID NO 52
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 52

```
Trp Val Leu Val Val Val Gly Gly Val Leu Ala Cys Tyr Ser Leu Leu
1               5                   10                  15

Val Thr Val Ala Phe Ile Ile Phe Trp Val
            20                  25
```

<210> SEQ ID NO 53
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 53

```
Val Ala Ala Ile Leu Gly Leu Gly Leu Val Leu Gly Leu Leu Gly Pro
1               5                   10                  15

Leu Ala Ile Leu Leu Ala Leu Tyr Leu Leu
```

```
            20                  25


<210> SEQ ID NO 54
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 54

Ala Leu Pro Ala Ala Leu Ala Val Ile Ser Phe Leu Leu Gly Leu Gly
1               5                   10                  15

Leu Gly Val Ala Cys Val Leu Ala
            20


<210> SEQ ID NO 55
<211> LENGTH: 42
<212> TYPE: PRT
<213> ORGANISM: Artificial Sequence
<220> FEATURE:
<223> OTHER INFORMATION: Synthetic Peptide

<400> SEQUENCE: 55

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 56
<211> LENGTH: 44
<212> TYPE: PRT
<213> ORGANISM: Artificial Sequence
<220> FEATURE:
<223> OTHER INFORMATION: Synthetic Peptide

<400> SEQUENCE: 56

Phe Trp Val Arg Ser Lys Arg Ser Arg Leu Leu His Ser Asp Tyr Met
1               5                   10                  15

Asn Met Thr Pro Arg Arg Pro Gly Pro Thr Arg Lys His Tyr Gln Pro
            20                  25                  30

Tyr Ala Pro Pro Arg Asp Phe Ala Ala Tyr Arg Ser
        35                  40


<210> SEQ ID NO 57
<211> LENGTH: 35
<212> TYPE: PRT
<213> ORGANISM: Artificial Sequence
<220> FEATURE:
<223> OTHER INFORMATION: Synthetic Peptide

<400> SEQUENCE: 57

Thr Lys Lys Lys Tyr Ser Ser Ser Val His Asp Pro Asn Gly Glu Tyr
1               5                   10                  15

Met Phe Met Arg Ala Val Asn Thr Ala Lys Lys Ser Arg Leu Thr Asp
            20                  25                  30

Val Thr Leu
        35


<210> SEQ ID NO 58
<211> LENGTH: 37
<212> TYPE: PRT
```

```
<213> ORGANISM: Artificial Sequence
<220> FEATURE:
<223> OTHER INFORMATION: Synthetic Peptide

<400> SEQUENCE: 58

Arg Arg Asp Gln Arg Leu Pro Pro Asp Ala His Lys Pro Pro Gly Gly
1               5                   10                  15

Gly Ser Phe Arg Thr Pro Ile Gln Glu Glu Gln Ala Asp Ala His Ser
            20                  25                  30

Thr Leu Ala Lys Ile
        35


<210> SEQ ID NO 59
<211> LENGTH: 114
<212> TYPE: PRT
<213> ORGANISM: Artificial Sequence
<220> FEATURE:
<223> OTHER INFORMATION: Synthetic Peptide

<400> SEQUENCE: 59

Cys Cys Leu Arg Arg His Gln Gly Lys Gln Asn Glu Leu Ser Asp Thr
1               5                   10                  15

Ala Gly Arg Glu Ile Asn Leu Val Asp Ala His Leu Lys Ser Glu Gln
            20                  25                  30

Thr Glu Ala Ser Thr Arg Gln Asn Ser Gln Val Leu Leu Ser Glu Thr
        35                  40                  45

Gly Ile Tyr Asp Asn Asp Pro Asp Leu Cys Phe Arg Met Gln Glu Gly
    50                  55                  60

Ser Glu Val Tyr Ser Asn Pro Cys Leu Glu Glu Asn Lys Pro Gly Ile
65                  70                  75                  80

Val Tyr Ala Ser Leu Asn His Ser Val Ile Gly Pro Asn Ser Arg Leu
                85                  90                  95

Ala Arg Asn Val Lys Glu Ala Pro Thr Glu Tyr Ala Ser Ile Cys Val
            100                 105                 110

Arg Ser


<210> SEQ ID NO 60
<211> LENGTH: 49
<212> TYPE: PRT
<213> ORGANISM: Artificial Sequence
<220> FEATURE:
<223> OTHER INFORMATION: Synthetic Peptide

<400> SEQUENCE: 60

His Gln Arg Arg Lys Tyr Arg Ser Asn Lys Gly Glu Ser Pro Val Glu
1               5                   10                  15

Pro Ala Glu Pro Cys Arg Tyr Ser Cys Pro Arg Glu Glu Glu Gly Ser
            20                  25                  30

Thr Ile Pro Ile Gln Glu Asp Tyr Arg Lys Pro Glu Pro Ala Cys Ser
        35                  40                  45

Pro


<210> SEQ ID NO 61
<211> LENGTH: 187
<212> TYPE: PRT
<213> ORGANISM: Artificial Sequence
<220> FEATURE:
<223> OTHER INFORMATION: Synthetic Peptide

<400> SEQUENCE: 61
```

```
Arg Arg Ala Cys Arg Lys Arg Ile Arg Gln Lys Leu His Leu Cys Tyr
1               5                   10                  15

Pro Val Gln Thr Ser Gln Pro Lys Leu Glu Leu Val Asp Ser Arg Pro
            20                  25                  30

Arg Arg Ser Ser Thr Gln Leu Arg Ser Gly Ala Ser Val Thr Glu Pro
        35                  40                  45

Val Ala Glu Glu Arg Gly Leu Met Ser Gln Pro Leu Met Glu Thr Cys
    50                  55                  60

His Ser Val Gly Ala Ala Tyr Leu Glu Ser Leu Pro Leu Gln Asp Ala
65                  70                  75                  80

Ser Pro Ala Gly Gly Pro Ser Ser Pro Arg Asp Leu Pro Glu Pro Arg
                85                  90                  95

Val Ser Thr Glu His Thr Asn Asn Lys Ile Glu Lys Ile Tyr Ile Met
            100                 105                 110

Lys Ala Asp Thr Val Ile Val Gly Thr Val Lys Ala Glu Leu Pro Glu
        115                 120                 125

Gly Arg Gly Leu Ala Gly Pro Ala Glu Pro Glu Leu Glu Glu Glu Leu
    130                 135                 140

Glu Ala Asp His Thr Pro His Tyr Pro Glu Gln Glu Thr Glu Pro Pro
145                 150                 155                 160

Leu Gly Ser Cys Ser Asp Val Met Leu Ser Val Glu Glu Glu Gly Lys
                165                 170                 175

Glu Asp Pro Leu Pro Thr Ala Ala Ser Gly Lys
            180                 185


<210> SEQ ID NO 62
<211> LENGTH: 54
<212> TYPE: PRT
<213> ORGANISM: Artificial Sequence
<220> FEATURE:
<223> OTHER INFORMATION: Synthetic Peptide

<400> SEQUENCE: 62

His Ile Trp Gln Leu Arg Ser Gln Cys Met Trp Pro Arg Glu Thr Gln
1               5                   10                  15

Leu Leu Leu Glu Val Pro Pro Ser Thr Glu Asp Ala Arg Ser Cys Gln
            20                  25                  30

Phe Pro Glu Glu Glu Arg Gly Glu Arg Ser Ala Glu Glu Lys Gly Arg
        35                  40                  45

Leu Gly Asp Leu Trp Val
    50


<210> SEQ ID NO 63
<211> LENGTH: 60
<212> TYPE: PRT
<213> ORGANISM: Artificial Sequence
<220> FEATURE:
<223> OTHER INFORMATION: Synthetic Peptide

<400> SEQUENCE: 63

Cys Val Lys Arg Arg Lys Pro Arg Gly Asp Val Val Lys Val Ile Val
1               5                   10                  15

Ser Val Gln Arg Lys Arg Gln Glu Ala Glu Gly Glu Ala Thr Val Ile
            20                  25                  30

Glu Ala Leu Gln Ala Pro Pro Asp Val Thr Thr Val Ala Val Glu Glu
        35                  40                  45

Thr Ile Pro Ser Phe Thr Gly Arg Ser Pro Asn His
    50                  55                  60
```

<210> SEQ ID NO 64
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(3)
<223> OTHER INFORMATION: X is any amino acid
<220> FEATURE:
<221> NAME/KEY: MISC_FEATURE
<222> LOCATION: (4)..(4)
<223> OTHER INFORMATION: X is leucine or isoleucine

<400> SEQUENCE: 64

Tyr Xaa Xaa Xaa
1

<210> SEQ ID NO 65
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(3)
<223> OTHER INFORMATION: X is any amino acid
<220> FEATURE:
<221> NAME/KEY: MISC_FEATURE
<222> LOCATION: (4)..(4)
<223> OTHER INFORMATION: X is leucine or isoleucine
<220> FEATURE:
<221> NAME/KEY: MISC_FEATURE
<222> LOCATION: (5)..(12)
<223> OTHER INFORMATION: X is any amino acid or absent
<220> FEATURE:
<221> NAME/KEY: MISC_FEATURE
<222> LOCATION: (14)..(15)
<223> OTHER INFORMATION: X is any amino acid
<220> FEATURE:
<221> NAME/KEY: MISC_FEATURE
<222> LOCATION: (16)..(16)
<223> OTHER INFORMATION: X is leucine or isoleucine

<400> SEQUENCE: 65

Tyr Xaa Xaa Xaa Xaa Xaa Xaa Xaa Xaa Xaa Xaa Xaa Tyr Xaa Xaa Xaa
1               5                   10                  15

<210> SEQ ID NO 66
<211> LENGTH: 113
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (82)..(82)
<223> OTHER INFORMATION: X is pyrrolysine
<220> FEATURE:
<221> NAME/KEY: MISC_FEATURE
<222> LOCATION: (92)..(92)
<223> OTHER INFORMATION: X is pyrrolysine
<220> FEATURE:
<221> NAME/KEY: MISC_FEATURE
<222> LOCATION: (95)..(95)
<223> OTHER INFORMATION: X is pyrrolysine
<220> FEATURE:
<221> NAME/KEY: MISC_FEATURE
<222> LOCATION: (97)..(97)
<223> OTHER INFORMATION: X is pyrrolysine

<400> SEQUENCE: 66

```
Met Gly Gly Leu Glu Pro Cys Ser Arg Leu Leu Leu Leu Pro Leu Leu
1               5                   10                  15

Leu Ala Val Ser Gly Leu Arg Pro Val Gln Ala Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Ala Thr Arg
65                  70                  75                  80

Lys Xaa Arg Ile Thr Glu Thr Glu Ser Pro Tyr Xaa Glu Leu Xaa Gly
                85                  90                  95

Xaa Arg Ser Asp Val Tyr Ser Asp Leu Asn Thr Gln Arg Pro Tyr Tyr
            100                 105                 110

Lys
```

<210> SEQ ID NO 67
<211> LENGTH: 112
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (81)..(81)
<223> OTHER INFORMATION: X is pyrrolysine
<220> FEATURE:
<221> NAME/KEY: MISC_FEATURE
<222> LOCATION: (91)..(91)
<223> OTHER INFORMATION: X is pyrrolysine
<220> FEATURE:
<221> NAME/KEY: MISC_FEATURE
<222> LOCATION: (94)..(94)
<223> OTHER INFORMATION: X is pyrrolysine
<220> FEATURE:
<221> NAME/KEY: MISC_FEATURE
<222> LOCATION: (96)..(96)
<223> OTHER INFORMATION: X is pyrrolysine

<400> SEQUENCE: 67

```
Met Gly Gly Leu Glu Pro Cys Ser Arg Leu Leu Leu Leu Pro Leu Leu
1               5                   10                  15

Leu Ala Val Ser Gly Leu Arg Pro Val Gln Ala Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Thr Arg Lys
65                  70                  75                  80

Xaa Arg Ile Thr Glu Thr Glu Ser Pro Tyr Xaa Glu Leu Xaa Gly Xaa
                85                  90                  95

Arg Ser Asp Val Tyr Ser Asp Leu Asn Thr Gln Arg Pro Tyr Tyr Lys
            100                 105                 110
```

<210> SEQ ID NO 68
<211> LENGTH: 102
<212> TYPE: PRT
<213> ORGANISM: Artificial Sequence
<220> FEATURE:
<223> OTHER INFORMATION: Synthetic Peptide

```
<220> FEATURE:
<221> NAME/KEY: MISC_FEATURE
<222> LOCATION: (71)..(71)
<223> OTHER INFORMATION: X is pyrrolysine
<220> FEATURE:
<221> NAME/KEY: MISC_FEATURE
<222> LOCATION: (81)..(81)
<223> OTHER INFORMATION: X is pyrrolysine
<220> FEATURE:
<221> NAME/KEY: MISC_FEATURE
<222> LOCATION: (84)..(84)
<223> OTHER INFORMATION: X is pyrrolysine
<220> FEATURE:
<221> NAME/KEY: MISC_FEATURE
<222> LOCATION: (86)..(86)
<223> OTHER INFORMATION: X is pyrrolysine

<400> SEQUENCE: 68

Met Gly Gly Leu Glu Pro Cys Ser Arg Leu Leu Leu Leu Pro Leu Leu
1               5                   10                  15

Leu Ala Val Ser Asp Cys Ser Cys Ser Thr Val Ser Pro Gly Val Leu
            20                  25                  30

Ala Gly Ile Val Met Gly Asp Leu Val Leu Thr Val Leu Ile Ala Leu
        35                  40                  45

Ala Val Tyr Phe Leu Gly Arg Leu Val Pro Arg Gly Arg Gly Ala Ala
    50                  55                  60

Glu Ala Ala Thr Arg Lys Xaa Arg Ile Thr Glu Thr Glu Ser Pro Tyr
65                  70                  75                  80

Xaa Glu Leu Xaa Gly Xaa Arg Ser Asp Val Tyr Ser Asp Leu Asn Thr
                85                  90                  95

Gln Arg Pro Tyr Tyr Lys
            100


<210> SEQ ID NO 69
<211> LENGTH: 101
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (70)..(70)
<223> OTHER INFORMATION: X is pyrrolysine
<220> FEATURE:
<221> NAME/KEY: MISC_FEATURE
<222> LOCATION: (80)..(80)
<223> OTHER INFORMATION: X is pyrrolysine
<220> FEATURE:
<221> NAME/KEY: MISC_FEATURE
<222> LOCATION: (83)..(83)
<223> OTHER INFORMATION: X is pyrrolysine
<220> FEATURE:
<221> NAME/KEY: MISC_FEATURE
<222> LOCATION: (85)..(85)
<223> OTHER INFORMATION: X is pyrrolysine

<400> SEQUENCE: 69

Met Gly Gly Leu Glu Pro Cys Ser Arg Leu Leu Leu Leu Pro Leu Leu
1               5                   10                  15

Leu Ala Val Ser Asp Cys Ser Cys Ser Thr Val Ser Pro Gly Val Leu
            20                  25                  30

Ala Gly Ile Val Met Gly Asp Leu Val Leu Thr Val Leu Ile Ala Leu
        35                  40                  45

Ala Val Tyr Phe Leu Gly Arg Leu Val Pro Arg Gly Arg Gly Ala Ala
    50                  55                  60

Glu Ala Thr Arg Lys Xaa Arg Ile Thr Glu Thr Glu Ser Pro Tyr Xaa
```

```
65                  70                  75                  80

Glu Leu Xaa Gly Xaa Arg Ser Asp Val Tyr Ser Asp Leu Asn Thr Gln
                85                  90                  95

Arg Pro Tyr Tyr Lys
            100


<210> SEQ ID NO 70
<211> LENGTH: 21
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: X is pyrrolysine
<220> FEATURE:
<221> NAME/KEY: MISC_FEATURE
<222> LOCATION: (8)..(8)
<223> OTHER INFORMATION: X is pyrrolysine
<220> FEATURE:
<221> NAME/KEY: MISC_FEATURE
<222> LOCATION: (10)..(10)
<223> OTHER INFORMATION: X is pyrrolysine
<220> FEATURE:
<221> NAME/KEY: MISC_FEATURE
<222> LOCATION: (21)..(21)
<223> OTHER INFORMATION: X is pyrrolysine

<400> SEQUENCE: 70

Glu Ser Pro Tyr Xaa Glu Leu Xaa Gly Xaa Arg Ser Asp Val Tyr Ser
1               5                   10                  15

Asp Leu Asn Thr Xaa
            20


<210> SEQ ID NO 71
<211> LENGTH: 86
<212> TYPE: PRT
<213> ORGANISM: Artificial Sequence
<220> FEATURE:
<223> OTHER INFORMATION: Synthetic Peptide

<400> SEQUENCE: 71

Met Ile Pro Ala Val Val Leu Leu Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
        35                  40                  45

Gln Val Arg Lys Ala Ala Ile Thr Ser Tyr Glu Lys Ser Asp Gly Val
    50                  55                  60

Tyr Thr Gly Leu Ser Thr Arg Asn Gln Glu Thr Tyr Glu Thr Leu Lys
65                  70                  75                  80

His Glu Lys Pro Pro Gln
                85


<210> SEQ ID NO 72
<211> LENGTH: 21
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (12)..(12)
<223> OTHER INFORMATION: X is pyrrolysine
```

<400> SEQUENCE: 72

```
Asp Gly Val Tyr Thr Gly Leu Ser Thr Arg Asn Xaa Glu Thr Tyr Glu
1               5                   10                  15

Thr Leu Lys His Glu
            20
```

<210> SEQ ID NO 73
<211> LENGTH: 171
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (140)..(140)
<223> OTHER INFORMATION: X is pyrrolysine
<220> FEATURE:
<221> NAME/KEY: MISC_FEATURE
<222> LOCATION: (147)..(147)
<223> OTHER INFORMATION: X is pyrrolysine
<220> FEATURE:
<221> NAME/KEY: MISC_FEATURE
<222> LOCATION: (150)..(150)
<223> OTHER INFORMATION: X is pyrrolysine
<220> FEATURE:
<221> NAME/KEY: MISC_FEATURE
<222> LOCATION: (159)..(159)
<223> OTHER INFORMATION: X is pyrrolysine

<400> SEQUENCE: 73

```
Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Xaa Ala Leu Leu Arg
    130                 135                 140

Asn Asp Xaa Val Tyr Xaa Pro Leu Arg Asp Arg Asp Asp Ala Xaa Tyr
145                 150                 155                 160

Ser His Leu Gly Gly Asn Trp Ala Arg Asn Lys
                165                 170
```

<210> SEQ ID NO 74
<211> LENGTH: 127
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (87)..(87)
<223> OTHER INFORMATION: X is pyrrolysine

```
<220> FEATURE:
<221> NAME/KEY: MISC_FEATURE
<222> LOCATION: (96)..(96)
<223> OTHER INFORMATION: X is pyrrolysine
<220> FEATURE:
<221> NAME/KEY: MISC_FEATURE
<222> LOCATION: (103)..(103)
<223> OTHER INFORMATION: X is pyrrolysine
<220> FEATURE:
<221> NAME/KEY: MISC_FEATURE
<222> LOCATION: (106)..(106)
<223> OTHER INFORMATION: X is pyrrolysine

<400> SEQUENCE: 74

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Xaa Val His Tyr Arg Thr Ala Asp Thr Xaa
                85                  90                  95

Ala Leu Leu Arg Asn Asp Xaa Val Tyr Xaa Pro Leu Arg Asp Arg Asp
            100                 105                 110

Asp Ala Gln Tyr Ser His Leu Gly Gly Asn Trp Ala Arg Asn Lys
        115                 120                 125


<210> SEQ ID NO 75
<211> LENGTH: 21
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is pyrrolysine
<220> FEATURE:
<221> NAME/KEY: MISC_FEATURE
<222> LOCATION: (5)..(5)
<223> OTHER INFORMATION: X is pyrrolysine
<220> FEATURE:
<221> NAME/KEY: MISC_FEATURE
<222> LOCATION: (14)..(14)
<223> OTHER INFORMATION: X is pyrrolysine

<400> SEQUENCE: 75

Asp Xaa Val Tyr Xaa Pro Leu Arg Asp Arg Asp Asp Ala Xaa Tyr Ser
1               5                   10                  15

His Leu Gly Gly Asn
            20


<210> SEQ ID NO 76
<211> LENGTH: 207
<212> TYPE: PRT
<213> ORGANISM: Artificial Sequence
<220> FEATURE:
<223> OTHER INFORMATION: Synthetic Peptide

<400> SEQUENCE: 76

Met Gln Ser Gly Thr His Trp Arg Val Leu Gly Leu Cys Leu Leu Ser
1               5                   10                  15
```

```
Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205


<210> SEQ ID NO 77
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 77

Asn Pro Asp Tyr Glu Pro Ile Arg Lys Gly Gln Arg Asp Leu Tyr Ser
1               5                   10                  15

Gly Leu Asn Gln Arg
            20


<210> SEQ ID NO 78
<211> LENGTH: 182
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (139)..(139)
<223> OTHER INFORMATION: X is pyrrolysine
<220> FEATURE:
<221> NAME/KEY: MISC_FEATURE
<222> LOCATION: (144)..(144)
<223> OTHER INFORMATION: X is pyrrolysine
<220> FEATURE:
<221> NAME/KEY: MISC_FEATURE
<222> LOCATION: (151)..(151)
<223> OTHER INFORMATION: X is pyrrolysine
<220> FEATURE:
<221> NAME/KEY: MISC_FEATURE
<222> LOCATION: (158)..(158)
<223> OTHER INFORMATION: X is pyrrolysine
<220> FEATURE:
<221> NAME/KEY: MISC_FEATURE
<222> LOCATION: (161)..(161)
```

<223> OTHER INFORMATION: X is pyrrolysine

<400> SEQUENCE: 78

Met Glu Gln Gly Lys Gly Leu Ala Val Leu Ile Leu Ala Ile Ile Leu
1 5 10 15

Leu Gln Gly Thr Leu Ala Gln Ser Ile Lys Gly Asn His Leu Val Lys
20 25 30

Val Tyr Asp Tyr Gln Glu Asp Gly Ser Val Leu Leu Thr Cys Asp Ala
35 40 45

Glu Ala Lys Asn Ile Thr Trp Phe Lys Asp Gly Lys Met Ile Gly Phe
50 55 60

Leu Thr Glu Asp Lys Lys Lys Trp Asn Leu Gly Ser Asn Ala Lys Asp
65 70 75 80

Pro Arg Gly Met Tyr Gln Cys Lys Gly Ser Gln Asn Lys Ser Lys Pro
85 90 95

Leu Gln Val Tyr Tyr Arg Met Cys Gln Asn Cys Ile Glu Leu Asn Ala
100 105 110

Ala Thr Ile Ser Gly Phe Leu Phe Ala Glu Ile Val Ser Ile Phe Val
115 120 125

Leu Ala Val Gly Val Tyr Phe Ile Ala Gly Xaa Asp Gly Val Arg Xaa
130 135 140

Ser Arg Ala Ser Asp Lys Xaa Thr Leu Leu Pro Asn Asp Xaa Leu Tyr
145 150 155 160

Xaa Pro Leu Lys Asp Arg Glu Asp Asp Gln Tyr Ser His Leu Gln Gly
165 170 175

Asn Gln Leu Arg Arg Asn
180

<210> SEQ ID NO 79
<211> LENGTH: 21
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is pyrrolysine
<220> FEATURE:
<221> NAME/KEY: MISC_FEATURE
<222> LOCATION: (5)..(5)
<223> OTHER INFORMATION: X is pyrrolysine
<220> FEATURE:
<221> NAME/KEY: MISC_FEATURE
<222> LOCATION: (14)..(14)
<223> OTHER INFORMATION: X is pyrrolysine
<220> FEATURE:
<221> NAME/KEY: MISC_FEATURE
<222> LOCATION: (19)..(19)
<223> OTHER INFORMATION: X is pyrrolysine

<400> SEQUENCE: 79

Asp Xaa Leu Tyr Xaa Pro Leu Lys Asp Arg Glu Asp Asp Xaa Tyr Ser
1 5 10 15

His Leu Xaa Gly Asn
20

<210> SEQ ID NO 80
<211> LENGTH: 163
<212> TYPE: PRT
<213> ORGANISM: Artificial Sequence
<220> FEATURE:
<223> OTHER INFORMATION: Synthetic Peptide

```
<220> FEATURE:
<221> NAME/KEY: MISC_FEATURE
<222> LOCATION: (114)..(114)
<223> OTHER INFORMATION: X is pyrrolysine
<220> FEATURE:
<221> NAME/KEY: MISC_FEATURE
<222> LOCATION: (142)..(142)
<223> OTHER INFORMATION: X is pyrrolysine

<400> SEQUENCE: 80

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Arg Arg Lys Asn Pro Gln Glu Gly Leu Tyr Asn Glu
            100                 105                 110

Leu Xaa Lys Asp Lys Met Ala Glu Ala Tyr Ser Glu Ile Gly Met Lys
        115                 120                 125

Gly Glu Arg Arg Arg Gly Lys Gly His Asp Gly Leu Tyr Xaa Gly Leu
    130                 135                 140

Ser Thr Ala Thr Lys Asp Thr Tyr Asp Ala Leu His Met Gln Ala Leu
145                 150                 155                 160

Pro Pro Arg


<210> SEQ ID NO 81
<211> LENGTH: 164
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (115)..(115)
<223> OTHER INFORMATION: X is pyrrolysine
<220> FEATURE:
<221> NAME/KEY: MISC_FEATURE
<222> LOCATION: (143)..(143)
<223> OTHER INFORMATION: X is pyrrolysine

<400> SEQUENCE: 81

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95
```

```
Gly Gly Lys Pro Gln Arg Arg Lys Asn Pro Gln Glu Gly Leu Tyr Asn
            100                 105                 110

Glu Leu Xaa Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Xaa Gly
    130                 135                 140

Leu Ser Thr Ala Thr Lys Asp Thr Tyr Asp Ala Leu His Met Gln Ala
145                 150                 155                 160

Leu Pro Pro Arg


<210> SEQ ID NO 82
<211> LENGTH: 112
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (14)..(14)
<223> OTHER INFORMATION: X is pyrrolysine
<220> FEATURE:
<221> NAME/KEY: MISC_FEATURE
<222> LOCATION: (17)..(17)
<223> OTHER INFORMATION: X is pyrrolysine
<220> FEATURE:
<221> NAME/KEY: MISC_FEATURE
<222> LOCATION: (19)..(19)
<223> OTHER INFORMATION: X is pyrrolysine
<220> FEATURE:
<221> NAME/KEY: MISC_FEATURE
<222> LOCATION: (55)..(55)
<223> OTHER INFORMATION: X is pyrrolysine
<220> FEATURE:
<221> NAME/KEY: MISC_FEATURE
<222> LOCATION: (63)..(63)
<223> OTHER INFORMATION: X is pyrrolysine
<220> FEATURE:
<221> NAME/KEY: MISC_FEATURE
<222> LOCATION: (91)..(91)
<223> OTHER INFORMATION: X is pyrrolysine

<400> SEQUENCE: 82

Arg Val Lys Phe Ser Arg Ser Ala Asp Ala Pro Ala Tyr Xaa Gln Gly
1               5                   10                  15

Xaa Asn Xaa Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Xaa Glu Gly Leu Tyr Asn Glu Leu Xaa Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Xaa Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 83
<211> LENGTH: 21
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
```

<223> OTHER INFORMATION: X is pyrrolysine

<400> SEQUENCE: 83

```
Asn Xaa Leu Tyr Asn Glu Leu Asn Leu Gly Arg Arg Glu Glu Tyr Asp
1               5                   10                  15

Val Leu Asp Lys Arg
            20
```

<210> SEQ ID NO 84
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 84

```
Glu Gly Leu Tyr Asn Glu Leu Gln Lys Asp Lys Met Ala Glu Ala Tyr
1               5                   10                  15

Ser Glu Ile Gly Met Lys
            20
```

<210> SEQ ID NO 85
<211> LENGTH: 21
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: X is pyrrolysine
<220> FEATURE:
<221> NAME/KEY: MISC_FEATURE
<222> LOCATION: (21)..(21)
<223> OTHER INFORMATION: X is pyrrolysine

<400> SEQUENCE: 85

```
Asp Gly Leu Tyr Xaa Gly Leu Ser Thr Ala Thr Lys Asp Thr Tyr Asp
1               5                   10                  15

Ala Leu His Met Xaa
            20
```

<210> SEQ ID NO 86
<211> LENGTH: 226
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (170)..(170)
<223> OTHER INFORMATION: X is pyrrolysine
<220> FEATURE:
<221> NAME/KEY: MISC_FEATURE
<222> LOCATION: (207)..(207)
<223> OTHER INFORMATION: X is pyrrolysine

<400> SEQUENCE: 86

```
Met Pro Gly Gly Pro Gly Val Leu Gln Ala Leu Pro Ala Thr Ile Phe
1               5                   10                  15

Leu Leu Phe Leu Leu Ser Ala Val Tyr Leu Gly Pro Gly Cys Gln Ala
            20                  25                  30

Leu Trp Met His Lys Val Pro Ala Ser Leu Met Val Ser Leu Gly Glu
        35                  40                  45

Asp Ala His Phe Gln Cys Pro His Asn Ser Ser Asn Asn Ala Asn Val
    50                  55                  60
```

```
Thr Trp Trp Arg Val Leu His Gly Asn Tyr Thr Trp Pro Pro Glu Phe
65                  70                  75                  80

Leu Gly Pro Gly Glu Asp Pro Asn Gly Thr Leu Ile Ile Gln Asn Val
                85                  90                  95

Asn Lys Ser His Gly Gly Ile Tyr Val Cys Arg Val Gln Glu Gly Asn
            100                 105                 110

Glu Ser Tyr Gln Gln Ser Cys Gly Thr Tyr Leu Arg Val Arg Gln Pro
        115                 120                 125

Pro Pro Arg Pro Phe Leu Asp Met Gly Glu Gly Thr Lys Asn Arg Ile
    130                 135                 140

Ile Thr Ala Glu Gly Ile Ile Leu Leu Phe Cys Ala Val Val Pro Gly
145                 150                 155                 160

Thr Leu Leu Leu Phe Arg Lys Arg Trp Xaa Asn Glu Lys Leu Gly Leu
                165                 170                 175

Asp Ala Gly Asp Glu Tyr Glu Asp Glu Asn Leu Tyr Glu Gly Leu Asn
            180                 185                 190

Leu Asp Asp Cys Ser Met Tyr Glu Asp Ile Ser Arg Gly Leu Xaa Gly
        195                 200                 205

Thr Tyr Gln Asp Val Gly Ser Leu Asn Ile Gly Asp Val Gln Leu Glu
    210                 215                 220

Lys Pro
225
```

```
<210> SEQ ID NO 87
<211> LENGTH: 188
<212> TYPE: PRT
<213> ORGANISM: Artificial Sequence
<220> FEATURE:
<223> OTHER INFORMATION: Synthetic Peptide

<400> SEQUENCE: 87

Met Pro Gly Gly Pro Gly Val Leu Gln Ala Leu Pro Ala Thr Ile Phe
1               5                   10                  15

Leu Leu Phe Leu Leu Ser Ala Val Tyr Leu Gly Pro Gly Cys Gln Ala
            20                  25                  30

Leu Trp Met His Lys Val Pro Ala Ser Leu Met Val Ser Leu Gly Glu
        35                  40                  45

Asp Ala His Phe Gln Cys Pro His Asn Ser Ser Asn Asn Ala Asn Val
    50                  55                  60

Thr Trp Trp Arg Val Leu His Gly Asn Tyr Thr Trp Pro Pro Glu Phe
65                  70                  75                  80

Leu Gly Pro Gly Glu Asp Pro Asn Glu Pro Pro Pro Arg Pro Phe Leu
                85                  90                  95

Asp Met Gly Glu Gly Thr Lys Asn Arg Ile Ile Thr Ala Glu Gly Ile
            100                 105                 110

Ile Leu Leu Phe Cys Ala Val Val Pro Gly Thr Leu Leu Leu Phe Arg
        115                 120                 125

Lys Arg Trp Gln Asn Glu Lys Leu Gly Leu Asp Ala Gly Asp Glu Tyr
    130                 135                 140

Glu Asp Glu Asn Leu Tyr Glu Gly Leu Asn Leu Asp Asp Cys Ser Met
145                 150                 155                 160

Tyr Glu Asp Ile Ser Arg Gly Leu Gln Gly Thr Tyr Gln Asp Val Gly
                165                 170                 175

Ser Leu Asn Ile Gly Asp Val Gln Leu Glu Lys Pro
            180                 185
```

<210> SEQ ID NO 88
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 88

```
Glu Asn Leu Tyr Glu Gly Leu Asn Leu Asp Asp Cys Ser Met Tyr Glu
1               5                   10                  15

Asp Ile Ser Arg Gly
            20
```

<210> SEQ ID NO 89
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 89

```
Arg Pro Arg Arg Ser Pro Ala Gln Asp Gly Lys Val Tyr Ile Asn Met
1               5                   10                  15

Pro Gly Arg Gly
            20
```

<210> SEQ ID NO 90
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 90

```
Arg Pro Arg Arg Ser Pro Ala Gln Asp Gly Lys Val Tyr Ile Asn Met
1               5                   10                  15

Pro Gly Arg Gly
            20
```

<210> SEQ ID NO 91
<211> LENGTH: 68
<212> TYPE: PRT
<213> ORGANISM: Artificial Sequence
<220> FEATURE:
<223> OTHER INFORMATION: Synthetic Peptide

<400> SEQUENCE: 91

```
Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
    50                  55                  60

Ala Tyr Arg Ser
65
```

<210> SEQ ID NO 92
<211> LENGTH: 68
<212> TYPE: PRT
<213> ORGANISM: Artificial Sequence

```
<220> FEATURE:
<223> OTHER INFORMATION: Synthetic Peptide

<400> SEQUENCE: 92

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
    50                  55                  60

Ala Tyr Arg Ser
65


<210> SEQ ID NO 93
<211> LENGTH: 619
<212> TYPE: PRT
<213> ORGANISM: Artificial Sequence
<220> FEATURE:
<223> OTHER INFORMATION: Synthetic Peptide

<400> SEQUENCE: 93

Met Pro Asp Pro Ala Ala His Leu Pro Phe Phe Tyr Gly Ser Ile Ser
1               5                   10                  15

Arg Ala Glu Ala Glu Glu His Leu Lys Leu Ala Gly Met Ala Asp Gly
            20                  25                  30

Leu Phe Leu Leu Arg Gln Cys Leu Arg Ser Leu Gly Gly Tyr Val Leu
        35                  40                  45

Ser Leu Val His Asp Val Arg Phe His His Phe Pro Ile Glu Arg Gln
    50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
            100                 105                 110

Gly Val Phe Asp Cys Leu Arg Asp Ala Met Val Arg Asp Tyr Val Arg
        115                 120                 125

Gln Thr Trp Lys Leu Glu Gly Glu Ala Leu Glu Gln Ala Ile Ile Ser
    130                 135                 140

Gln Ala Pro Gln Val Glu Lys Leu Ile Ala Thr Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Ala Gln Thr Asp Gly Lys Phe Leu Leu Arg Pro Arg
            180                 185                 190

Lys Glu Gln Gly Thr Tyr Ala Leu Ser Leu Ile Tyr Gly Lys Thr Val
        195                 200                 205

Tyr His Tyr Leu Ile Ser Gln Asp Lys Ala Gly Lys Tyr Cys Ile Pro
    210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255

Ser Ser Ala Ser Asn Ala Ser Gly Ala Ala Ala Pro Thr Leu Pro Ala
```

```
            260                 265                 270

His Pro Ser Thr Leu Thr His Pro Gln Arg Arg Ile Asp Thr Leu Asn
        275                 280                 285

Ser Asp Gly Tyr Thr Pro Glu Pro Ala Arg Ile Thr Ser Pro Asp Lys
    290                 295                 300

Pro Arg Pro Met Pro Met Asp Thr Ser Val Tyr Glu Ser Pro Tyr Ser
305                 310                 315                 320

Asp Pro Glu Glu Leu Lys Asp Lys Lys Leu Phe Leu Lys Arg Asp Asn
                325                 330                 335

Leu Leu Ile Ala Asp Ile Glu Leu Gly Cys Gly Asn Phe Gly Ser Val
            340                 345                 350

Arg Gln Gly Val Tyr Arg Met Arg Lys Lys Gln Ile Asp Val Ala Ile
        355                 360                 365

Lys Val Leu Lys Gln Gly Thr Glu Lys Ala Asp Thr Glu Glu Met Met
    370                 375                 380

Arg Glu Ala Gln Ile Met His Gln Leu Asp Asn Pro Tyr Ile Val Arg
385                 390                 395                 400

Leu Ile Gly Val Cys Gln Ala Glu Ala Leu Met Leu Val Met Glu Met
                405                 410                 415

Ala Gly Gly Gly Pro Leu His Lys Phe Leu Val Gly Lys Arg Glu Glu
            420                 425                 430

Ile Pro Val Ser Asn Val Ala Glu Leu Leu His Gln Val Ser Met Gly
        435                 440                 445

Met Lys Tyr Leu Glu Glu Lys Asn Phe Val His Arg Asp Leu Ala Ala
    450                 455                 460

Arg Asn Val Leu Leu Val Asn Arg His Tyr Ala Lys Ile Ser Asp Phe
465                 470                 475                 480

Gly Leu Ser Lys Ala Leu Gly Ala Asp Asp Ser Tyr Tyr Thr Ala Arg
                485                 490                 495

Ser Ala Gly Lys Trp Pro Leu Lys Trp Tyr Ala Pro Glu Cys Ile Asn
            500                 505                 510

Phe Arg Lys Phe Ser Ser Arg Ser Asp Val Trp Ser Tyr Gly Val Thr
        515                 520                 525

Met Trp Glu Ala Leu Ser Tyr Gly Gln Lys Pro Tyr Lys Lys Met Lys
    530                 535                 540

Gly Pro Glu Val Met Ala Phe Ile Glu Gln Gly Lys Arg Met Glu Cys
545                 550                 555                 560

Pro Pro Glu Cys Pro Pro Glu Leu Tyr Ala Leu Met Ser Asp Cys Trp
                565                 570                 575

Ile Tyr Lys Trp Glu Asp Arg Pro Asp Phe Leu Thr Val Glu Gln Arg
            580                 585                 590

Met Arg Ala Cys Tyr Tyr Ser Leu Ala Ser Lys Val Glu Gly Pro Pro
        595                 600                 605

Gly Ser Thr Gln Lys Ala Glu Ala Ala Cys Ala
    610                 615
```

<210> SEQ ID NO 94
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 94

Tyr Pro Tyr Asp Val Pro Asp Tyr Ala

```
1               5


<210> SEQ ID NO 95
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 95

Glu Gln Lys Leu Ile Ser Glu Glu Asp Leu
1               5                   10


<210> SEQ ID NO 96
<211> LENGTH: 290
<212> TYPE: PRT
<213> ORGANISM: Artificial Sequence
<220> FEATURE:
<223> OTHER INFORMATION: Synthetic Peptide

<400> SEQUENCE: 96

Met Glu Thr Asp Thr Leu Leu Leu Trp Val Leu Leu Leu Trp Val Pro
1               5                   10                  15

Gly Ser Thr Gly Ala Gly Gly Ser Asp Tyr Lys Asp Asp Asp Asp Lys
            20                  25                  30

Gly Gly Ser Glu Val Gln Leu Val Glu Ser Gly Gly Gly Leu Val Gln
        35                  40                  45

Pro Gly Gly Ser Leu Arg Leu Ser Cys Ala Ala Ser Gly Tyr Ala Phe
    50                  55                  60

Thr Asn Tyr Leu Ile Glu Trp Val Arg Gln Ala Pro Gly Lys Gly Leu
65                  70                  75                  80

Glu Trp Val Gly Val Ile Asn Pro Gly Ser Gly Gly Ser Asn Tyr Asn
                85                  90                  95

Glu Lys Phe Lys Gly Arg Ala Thr Ile Ser Ala Asp Asn Ser Lys Asn
            100                 105                 110

Thr Leu Tyr Leu Gln Met Asn Ser Leu Arg Ala Glu Asp Thr Ala Val
        115                 120                 125

Tyr Tyr Cys Ala Arg Ser Gly Gly Phe Tyr Phe Asp Tyr Trp Gly Gln
    130                 135                 140

Gly Thr Leu Val Thr Val Ser Ser Ala Ser Thr Lys Gly Pro Ser Gly
145                 150                 155                 160

Gly Gly Gly Ser Gly Gly Gly Gly Ser Gly Gly Gly Gly Ser Asp Ile
                165                 170                 175

Gln Met Thr Gln Ser Pro Ser Ser Leu Ser Ala Ser Val Gly Asp Arg
            180                 185                 190

Val Thr Ile Thr Cys Arg Ala Ser Gln Ser Val Leu Tyr Ser Ser Asn
        195                 200                 205

Gln Lys Asn Tyr Leu Ala Trp Tyr Gln Gln Lys Pro Gly Lys Ala Pro
    210                 215                 220

Lys Leu Leu Ile Tyr Trp Ala Ser Thr Arg Glu Ser Gly Val Pro Ser
225                 230                 235                 240

Arg Phe Ser Gly Ser Gly Ser Gly Thr Asp Phe Thr Leu Thr Ile Ser
                245                 250                 255

Ser Leu Gln Pro Glu Asp Phe Ala Thr Tyr Tyr Cys His Gln Tyr Leu
            260                 265                 270

Ser Ser Asp Thr Phe Gly Gln Gly Thr Lys Val Glu Ile Lys Arg Thr
        275                 280                 285
```

```
Val Ala
    290


<210> SEQ ID NO 97
<211> LENGTH: 278
<212> TYPE: PRT
<213> ORGANISM: Artificial Sequence
<220> FEATURE:
<223> OTHER INFORMATION: Synthetic Peptide

<400> SEQUENCE: 97

Met Glu Thr Asp Thr Leu Leu Leu Trp Val Leu Leu Leu Trp Val Pro
1               5                   10                  15

Gly Ser Thr Gly Ala Gly Gly Ser Asp Tyr Lys Asp Asp Asp Asp Lys
            20                  25                  30

Gly Gly Ser Gln Val Gln Leu Val Gln Ser Gly Ala Glu Val Lys Lys
        35                  40                  45

Pro Gly Ser Ser Val Lys Val Ser Cys Lys Ala Ser Gly Tyr Thr Phe
    50                  55                  60

Ser Ser Asn Val Ile Ser Trp Val Arg Gln Ala Pro Gly Gln Gly Leu
65                  70                  75                  80

Glu Trp Met Gly Gly Val Ile Pro Ile Val Asp Ile Ala Asn Tyr Ala
                85                  90                  95

Gln Arg Phe Lys Gly Arg Val Thr Ile Thr Ala Asp Glu Ser Thr Ser
            100                 105                 110

Thr Thr Tyr Met Glu Leu Ser Ser Leu Arg Ser Glu Asp Thr Ala Val
        115                 120                 125

Tyr Tyr Cys Ala Leu Pro Arg Ala Phe Val Leu Asp Ala Met Asp Tyr
    130                 135                 140

Trp Gly Gln Gly Thr Leu Val Thr Val Ser Ser Gly Gly Gly Gly Ser
145                 150                 155                 160

Gly Gly Gly Gly Ser Gly Gly Gly Gly Ser Glu Thr Val Leu Thr Gln
                165                 170                 175

Ser Pro Gly Thr Leu Ser Leu Ser Pro Gly Glu Arg Ala Thr Leu Ser
            180                 185                 190

Cys Arg Ala Ser Gln Ser Leu Gly Ser Ser Tyr Leu Ala Trp Tyr Gln
        195                 200                 205

Gln Lys Pro Gly Gln Ala Pro Arg Leu Leu Ile Tyr Gly Ala Ser Ser
    210                 215                 220

Arg Ala Pro Gly Ile Pro Asp Arg Phe Ser Gly Ser Gly Ser Gly Thr
225                 230                 235                 240

Asp Phe Thr Leu Thr Ile Ser Arg Leu Glu Pro Glu Asp Phe Ala Val
                245                 250                 255

Tyr Tyr Cys Gln Gln Tyr Ala Asp Ser Pro Ile Thr Phe Gly Gln Gly
            260                 265                 270

Thr Arg Leu Glu Ile Lys
        275


<210> SEQ ID NO 98
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 98

Glu Ser Lys Tyr Gly Pro Pro Cys Pro Pro Cys Pro
1               5                   10
```

<210> SEQ ID NO 99
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 99

```
Glu Ser Lys Tyr Gly Pro Pro Cys Pro Ser Cys Pro
1               5                   10
```

<210> SEQ ID NO 100
<211> LENGTH: 246
<212> TYPE: PRT
<213> ORGANISM: Artificial Sequence
<220> FEATURE:
<223> OTHER INFORMATION: Synthetic Peptide

<400> SEQUENCE: 100

```
Asp Ile Val Leu Thr Gln Ser Pro Ala Ile Leu Ser Ala Ser Pro Gly
1               5                   10                  15

Glu Lys Val Thr Met Thr Cys Arg Ala Ser Ser Ser Val Asn Tyr Met
            20                  25                  30

Asp Trp Tyr Gln Lys Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Gly Gly Thr Lys Leu Glu Ile Lys Gly Ser Thr Ser Gly Gly
            100                 105                 110

Gly Ser Gly Gly Gly Ser Gly Gly Gly Gly Ser Ser Glu Val Gln Leu
        115                 120                 125

Gln Gln Ser Gly Ala Glu Leu Val Lys Pro Gly Ala Ser Val Lys Met
    130                 135                 140

Ser Cys Lys Ala Ser Gly Tyr Thr Phe Thr Ser Tyr Asn Met His Val
145                 150                 155                 160

Trp Lys Gln Thr Pro Gly Gln Gly Leu Glu Trp Ile Gly Ala Ile Tyr
                165                 170                 175

Pro Gly Asn Gly Asp Thr Ser Tyr Asn Gln Lys Phe Lys Gly Lys Ala
            180                 185                 190

Thr Leu Thr Ala Asp Lys Ser Ser Ser Thr Ala Tyr Met Gln Leu Ser
        195                 200                 205

Ser Leu Thr Ser Glu Asp Ser Ala Asp Tyr Tyr Cys Ala Arg Ser Asn
    210                 215                 220

Tyr Tyr Gly Ser Ser Tyr Trp Phe Phe Asp Val Trp Gly Ala Gly Thr
225                 230                 235                 240

Thr Val Thr Val Ser Ser
                245
```

<210> SEQ ID NO 101
<211> LENGTH: 245
<212> TYPE: PRT
<213> ORGANISM: Artificial Sequence
<220> FEATURE:
<223> OTHER INFORMATION: Synthetic Peptide

```
<400> SEQUENCE: 101

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser
                245
```

BI-SPECIFIC CHIMERIC ANTIGEN RECEPTOR

CROSS-REFERENCE TO RELATED APPLICATIONS

This application is a divisional application of U.S. patent application Ser. No. 15/772,403, filed Apr. 30, 2018, which is a national phase application under 35 U.S.C. § 371 of International Application No. PCT/US2016/059444, filed Oct. 28, 2016, which claims the benefit of priority of U.S. Provisional Patent Application No. 62/248,685, filed Oct. 30, 2015. The entire contents of the above-referenced disclosures are specifically incorporated herein by reference without disclaimer.

This invention was made with government support under OD012133, and CA183528 awarded by the National Institutes of Health. The government has certain rights in the invention.

BACKGROUND OF THE INVENTION

1. Field of the Invention

The present invention relates generally to the field of biotechnology and medicine. More particularly, it concerns polypeptides and cells containing the polypeptides useful for stimulating an immune response in the presence of TGF-β.

2. Background

TGF-β is a pleiotropic cytokine found at high levels in a variety of pathogenic states, including solid tumors, fibrosis, and disregulated wounds. Therapeutic design for solid tumors has been directed to neutralizing TGF-β in the tumor microenvironment. While many anti-TGF-β antibodies exist, antibodies as therapeutics have some drawbacks. For example, antibodies can be large compared to other antigen-binding molecules and are multi-chain proteins encoded by multiple genes. Both of these aspects lead to higher production costs. Chemicals that inhibit TGF-β have also been identified, but typically come with toxicity issues stemming from metabolic byproducts in the liver.

Strategies using adoptive T-cell therapy with TGF-β-insensitive T cells expressing a dominant-negative TGF-β receptor have been explored. However, the mere neutralization of the TGF-β signal may not be sufficient, and reversing the TGF-β signal from an immunosuppressant to an immunostimulant may provide more promising therapeutic strategies.

Therefore, there is a need in the art for more effective therapies that counteract the action of TGF-β and also provide the benefit of a more cost-effective production.

SUMMARY OF THE INVENTION

The polypeptides described herein fulfill the need in the art by providing polypeptides that, when expressed in a cell, are capable of not only neutralizing the TGF-β but also specifically triggering T-cell activation in the presence of TGF-β. T-cell activation spurs the immune cell to produce immunostimulatory cytokines and proliferate, thus turning TGF-β from an immunosuppressive signal to an activating stimulus. Accordingly, aspects of the disclosure relate to polypeptides comprising a signal peptide, an antigen-binding domain with a variable heavy (VH) and variable light (VL) region, a peptide spacer, a transmembrane domain, and an endodomain; wherein the antigen-binding domain specifically binds to TGFβ.

In some aspects the disclosure relates to a polypeptide comprising a signal peptide, an antigen-binding domain with a variable heavy (VH) and variable light (VL) region, a peptide spacer, a transmembrane domain, and an endodomain; wherein the VH region comprises SEQ ID NO:5 (HCDR1), SEQ ID NO:6 (HCDR2); and SEQ ID NO:7 (HCDR3) and the VL region comprises SEQ ID NO:8 (LCDR1), SEQ ID NO:9 (LCDR2); and SEQ ID NO:10 (LCDR3). In some embodiments, the VH comprises SEQ ID NO: 1 and the VL comprises SEQ ID NO:2.

In some aspects the disclosure relates to a polypeptide comprising a signal peptide, an antigen-binding domain with a variable heavy (VH) and variable light (VL) region, a peptide spacer, a transmembrane domain, and an endodomain; wherein the VH region comprises SEQ ID NO:11 (HCDR1), SEQ ID NO:12 (HCDR2); and SEQ ID NO:13 (HCDR3) and the VL region comprises SEQ ID NO:14 (LCDR1), SEQ ID NO:15 (LCDR2); and SEQ ID NO:16 (LCDR3). In some embodiments, the VH comprises SEQ ID NO:3 and the VL comprises SEQ ID NO:4.

In some aspects the disclosure relates to a polypeptide comprising a signal peptide, an antigen-binding domain with a variable heavy (VH) and variable light (VL) region, a peptide spacer, a transmembrane domain, and an endodomain; wherein the VH region comprises SEQ ID NO:21 (HCDR1), SEQ ID NO:22 (HCDR2); and SEQ ID NO:23 (HCDR3) and the VL region comprises SEQ ID NO:24 (LCDR1), SEQ ID NO:25 (LCDR2); and SEQ ID NO:26 (LCDR3). In some embodiments, the VH comprises SEQ ID NO:19 and the VL comprises SEQ ID NO:20.

The polypeptides described above and herein are polypeptides that are a continuous, single chain.

A polynucleotide or polynucleotide region (or a polypeptide or polypeptide region) has a certain percentage (for example, 60%, 65%, 70%, 75%, 80%, 85%, 90%, 95%, 98% or 99%—or any range derivable therein) of "sequence identity" or "homology" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology.

The polypeptides of the current disclosure may have a region, domain, linker, spacer, etc. that has at least, at most, or exactly 80, 81, 82, 83, 84, 85, 86, 87, 88, 89, 90, 91, 92, 93, 94, 95, 96, 97, 98, 99, or 100% identity (or any range derivable therein) to all or a portion of the amino acid sequences described herein. In certain embodiments, polypeptides described throughout this disclosure are isolated, meaning it is not found in the cellular milieu. In some cases, they are purified, which means it is mostly if not completely separated from polypeptides having a different amino acid sequence and/or chemical formula.

In some embodiments, the VH and VL are separated by a peptide linker. It is contemplated that a peptide linker may separate any domain/region described in the polypeptides of the disclosure. In some embodiments, the peptide linker is a peptide composed of only glycine and serine residues (a glycine-serine linker). In some embodiments, the peptide linker is at least, at most, or exactly 4, 5, 6, 7, 8, 9, 10, 15, 20, 25, 30, 35, 40, 45, 50, 55, 60, 65, 70, 75, 100, 125, 150, or 200 amino acids (or any derivable range therein). In some embodiments, the peptide linker is one known in the art or described herein.

In some embodiments, the polypeptide has the structure S-X-PL-Y-PS-T-E or S-Y-PL-X-PS-T-E wherein S is the signal peptide, X is VH, PL is a peptide linker, Y is VL, PS is the peptide spacer, T is the transmembrane domain, and E is the endodomain. In some embodiments, the polypeptide has the structure: S-X-Y-PS-T-E or S-Y-X-PS-T-E, wherein S, X, Y, PS, T, and E are defined as above. When referring to peptides and polypeptides herein, the sequences and structures are written and interpreted as proceeding from the N-terminus to the C-terminus, which is standard practice in the art.

In some embodiments, the polypeptide further comprises a co-stimulatory region. In some embodiments, the co-stimulatory region is between the transmembrane domain and endodomain. In some embodiments, the polypeptides comprise at least, at most, or exactly 1, 2, 3, 4, 5, 6, 7, 8, 9, or 10 (or any derivable ranges therein) co-stimulatory regions. In some embodiments, the co-stimulatory region is one known in the art or described herein.

In some embodiments, the transmembrane domain comprises a transmembrane domain of CD28. In some embodiments the transmembrane domain is all or part of a transmembrane domain known in the art or described herein.

In some embodiments, the endodomain comprises a CD28 or CD3-zeta signaling domain or both. In some embodiments the endodomain is all or part of an endodomain known in the art or described herein. In some embodiments, the endodomain is a CD3-zeta signaling domain. In some embodiments, the endodomain comprises one or more, such as 2, 3, 4, 5, 6, 7, 8, 9, 10 portions of suitable endodomains described herein.

In some embodiments, the peptide spacer comprises a hinge region. In some embodiments, the hinge is the hinge region of an IgG molecule. In some embodiments, the hinge is a hinge region known in the art or described herein. In some embodiments, the peptide spacer comprises or further comprises a $CH_2CH_3$ region of an IgG molecule. In some embodiments, the peptide spacer comprises one or more of a hinge region, $CH_1$, $CH_2$, and $CH_3$ region. In some embodiments, the peptide spacer is derived from a hinge, $CH_1$, $CH_2$, and/or $CH_3$ region or other region of an IgG1, IgG2, IgG3, IgG4, IgA1, IgA2, IgD, IgE, or IgM from human, mouse, rat, dog, donkey, goat, or rabbit. In some embodiments, the peptide spacer comprises the hinge and $CH_2CH_3$ region of an IgG molecule. In some embodiments, the $CH_2CH_3$ region of an IgG molecule has additional L235E/N297Q or L235D/N297Q mutations to prevent Fc receptor binding. In some embodiments, the peptide spacer consists of the hinge region of an IgG molecule. In some embodiments, the peptide spacer is less than 30, 20, 15, 10, 9, 8, 7, 6, 5, or 4 amino acids. In some embodiments, the peptide spacer is less than, more than, or exactly 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, 210, 220, 225, 230, 240, 250, 260, 270, 280, 290, 300, 310, 320, 330, 340, 350, 360, 370, 380, 390, 400, 450, 500, 550, 600, or 700 amino acids (or any derivable range therein). In some embodiments, the peptide spacer comprises less than 50 amino acids. In some embodiments, the peptide spacer comprises more than 50 amino acids.

In some embodiments, the polypeptide further comprises a detection peptide. In some embodiments, the detection peptide is a peptide of SEQ ID NO: 17, an HA tag (SEQ ID NO: 94), or a cMyc tag (SEQ ID NO:95). In some embodiments, the detection peptide is flanked by linkers. In some embodiments, a linker (e.g. peptide linker as described herein) is at the amino portion of the detection peptide. In some embodiments, a linker (e.g. peptide linker as described herein) is at the carboxy portion of the detection peptide. In some embodiments, a linker is at the amino and carboxy portion of the detection peptide. In some embodiments, the detection peptide is at the amino portion of the VH and VL regions. In some embodiments, the detection peptide is between the signal peptide and the antigen binding domain.

In some embodiments, the signal peptide comprises SEQ ID NO:18. In some embodiments, the signal peptide is one know in the art or described herein.

In some embodiments, the polypeptide further comprises a cancer-molecule-specific antigen-binding domain. For example, the polypeptide may be a bi-specific chimeric antigen receptor (CAR) wherein the polypeptide comprises an antigen-binding domain for TGF-β and an antigen-binding domain for a cancer molecule or cancer antigen. The antigen-binding domains may be separated by a peptide spacer/linker. In some embodiments, the cancer molecule comprises Her2. In some embodiments, the cancer molecule comprises CD19 or CD20. In some embodiments, the cancer molecule or cancer antigen is one known in the art or described herein.

In some embodiments, the antigen-binding domain specifically binds to soluble TGF-β. It was previously unknown that polypeptides similar to those of the disclosure could bind to soluble antigens and transduce signals in response to soluble antigens.

The polypeptides described herein may include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more variant amino acids within at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of SEQ ID NO: 1-95.

Further aspects of the disclosure relate to nucleic acids encoding a polypeptide described herein. In some aspects, the disclosure relates to a cell comprising one or more polypeptides described herein. In some embodiments, the cell further comprises a cancer-specific CAR. In some embodiments, the cancer-specific CAR is a separate polypeptide from the TGF-β CAR. In some embodiments, the cancer-specific CAR specifically binds to Her2. In some embodiments, the cancer-specific CAR specifically binds to CD19 or CD20. In some embodiments, the cancer-specific CAR specifically binds to a cancer molecule or antigen known in the art and/or described herein. In some embodiments, the cell is an immune cell. In some embodiments, the cell is a progenitor cell or stem cell. In some embodiments, the progenitor or stem cell is in vitro differentiated into an immune cell. In some embodiments, the cell is a T cell. In some embodiments, the cell is a CD4+ or CD8+ T cell. In some embodiments, the cell is a natural killer cell. In some embodiments, the cell is ex vivo. The term immune cells includes cells of the immune system that are involved in defending the body against both infectious disease and foreign materials. Immune cells may include, for example, neutrophils, eosinophils, basophils, natural killer cells, lymphocytes such as B cells and T cells, and monocytes. T cells may include, for example, CD4+, CD8+, T helper cells, cytotoxic T cells, γδ T cells, regulatory T cells, suppressor T cells, and natural killer T cells. In a specific embodiment, the T cell is a regulatory T cell.

Further aspects of the disclosure relate to methods for stimulating an immune response comprising contacting a cell of the disclosure (i.e. cell comprising an antigen-binding polypeptide described herein) with TGF-β. In some embodiments, stimulating an immune response comprises increasing expression and/or secretion of immune stimulating cytokines and/or molecules. In some embodiments, the cytokine and/or molecule is a pro-inflammatory cytokine or molecule. In some embodiments, the immune stimulating cytokines and/or molecules are one or more of TNF-α, IFN-β, IFN-γ, IL-1, IL-2, IL-4, IL-6, IL-8, IL-10, IL-12, IL-18 and granulocyte-macrophage colony stimulating factor. In some embodiments, stimulating an immune response comprises increasing proliferation of immune cells. In some embodiments, the immune cells are T cells. In some embodiments, the TGF-β is endogenous TGF-β produced in a human subject in need of immune stimulation. In some embodiments, the human subject has cancer, fibrosis, or an open wound. In some embodiments the human subject has a B-cell malignancy. In some embodiments, the human subject has a solid tumor. A solid tumor is an abnormal mass of tissue that usually does not contain cysts or liquid areas. Solid tumors may be benign (not cancer), or malignant (cancer). Different types of solid tumors are named for the type of cells that form them. Examples of solid tumors are sarcomas, carcinomas, and lymphomas. In some embodiments, the methods are for treating a person with an indication, wherein the indication is characterized by a pathogenic level of expression of TGF-β. In some embodiments, the cells and polypeptides described herein can be used for treating cancer, dysregulated wounds, fibrosis, open wounds, solid tumors, etc. . . . where the etiology of the condition, at least in part, is based on the expression of TGF-β. In some embodiments, the cell (i.e. cell of the disclosure comprising the antigen-binding polypeptide) is in the human subject in need of immune stimulation. In some embodiments, the method further comprises administering a cell described herein comprising the polypeptides or nucleic acids of the disclosure to a human subject.

Further method aspects relate to a method for detecting TGF-β in a solution comprising contacting the cells of the disclosure and measuring immune stimulation; wherein an increase in immune stimulation indicates the presence of TGF-β and no increase in immune stimulation indicates the absence of TGF-β. In some embodiments, immune stimulation comprises the expression of immune stimulating cytokines and/or molecules. In some embodiments, the immune stimulating cytokines and/or molecules are one or more of TNF-α, IFN-β, IFN-γ, IL-1, IL-2, IL-4, IL-6, IL-8, IL-10, IL-12, IL-18 and granulocyte-macrophage colony stimulating factor. In some embodiments, immune stimulation comprises an increase in the proliferation of immune cells. In some embodiments, the immune cells are T cells. In some embodiments, the cells are ex vivo.

An increase in expression or proliferation as described herein may be at least, at most, or exactly 1, 2, 3, 4, 5, 6, 7, 8, 9, 10, 50, 100, 200, 300, 500, or 1000 fold increase over a base-line expression level such as a control (non-disease, non-TGF-β or non-antigen binding polypeptide control).

Further aspects of the disclosure relate to methods for making the polypeptides of the disclosure comprising expressing a nucleotide encoding the polypeptide in a cell. Further aspects relate to cultured cells, frozen cells, suspended cells, or adhered cells comprising a polypeptide described herein.

Aspects of the disclosure relate to a method for treating a disease or pathological condition comprising administering a cell of the disclosure to a patient. In some embodiments, the patient is a human patient.

In some embodiments, the cell is a T regulatory cell (i.e., regulatory T cell comprising the TGF-β-binding polypeptides described herein). In some embodiments, the disease is an autoimmune disease. In some embodiments, the autoimmune disease is rheumatoid arthritis. In some embodiments, the autoimmune disease is one described herein.

In some embodiments of the method aspects, the method further comprises administration of TGF-β to the subject.

In some aspects, the method comprises or further comprises expanding and/or inducing proliferation of T cells in vitro, the method comprising contacting the in vitro T cell of the disclosure with a composition comprising TGF-β. In some embodiments, the T cell is a regulatory cell. In some embodiments, the T cell is a T cell described herein. In some embodiments, the expanded regulatory T cells comprise less than 10% of non-regulatory T cells. In some embodiments, the expanded regulatory T cells comprise less than 0.5, 1, 2, 3, 4, 5, 6, 7, 8, 9, 10, 12, 14, 16, 18, 20, 22, 24, 26, 28, 30, 32, 34, 36, 38, 40, 42, 44, 46, 48, or 50% or any derivable range therein.

In some embodiments, the composition comprises 1-50 ng/ml of TGF-β. In some embodiments, the composition comprises at least, at most, or about 0.5, 1, 1.5, 2, 2.5, 3, 3.5, 4, 4.5, 5, 5.5, 6, 6.5, 7, 7.5, 8, 8.5, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 ng/ml of TGF-β (or any range derivable therein).

In some embodiments, the composition further comprises IL-2. In some embodiments, the composition comprises 20-400 U/mL of IL-2. In some embodiments, the composition comprises at least, at most, or about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600 U/mL of IL-2 (or any range derivable therein).

In some embodiments, the method further comprises contacting the cells with feeder cells. In some embodiments, the feeder cells are irradiated. Feeder cells or support cells can include, for example, fibroblasts, mouse embryonic fibroblasts, JK1 cells, SNL 76/7 cells, human fetal skin cells, human fibroblasts, and human foreskin fibroblasts.

In some embodiments, the method excludes contacting T cells with feeder cells. In some cases, the excluded feeder cells are from a different animal species as the T cells.

In one embodiment of the methods described herein, the subject is a human subject. The terms "individual," "subject," "host," and "patient," used interchangeably herein, refer to a mammal, including, but not limited to, murines (e.g., rats, mice), lagomorphs (e.g., rabbits), non-human primates, humans, canines, felines, ungulates (e.g., equines, bovines, ovines, porcines, caprines), etc.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2 shows that TGF-β CARs are expressed on the cell surface. A TGF-β CAR was created using scFv #2. Surface staining and flow cytometry show that TGF-β CARs are presented at the cell surface of CD4+ and CD8+ T cells. The receptor's extracellular domain contains the FLAG epitope. EGFRt is a truncated epidermal growth factor receptor that is an indicator of cell transduction.

DESCRIPTION OF ILLUSTRATIVE EMBODIMENTS

Figure 1:
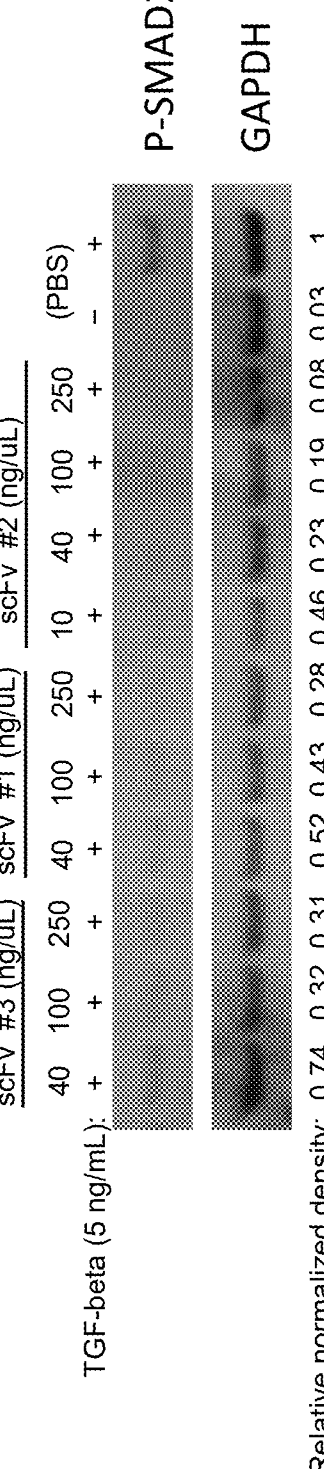
FIG. 1 shows that TGF-β scFvs neutralizes human TGF-β. The indicated amounts of TGF-β and anti-TGF-β scFvs were added to HepG2 cells in culture for 30 min. Neutralization of TGF-β is indicated by a loss in the phospho-SMAD2 response, as detected by western blot.

Polypeptides, cells, and methods described herein can be used to neutralize TGF-β and specifically trigger T-cell activation in the presence of TGF-β.

I. Definitions

The peptides of the disclosure relate to peptides comprising CARs or chimeric antigen receptors. CARs are engineered receptors, which graft an arbitrary specificity onto an immune effector cell. Typically, these receptors are used to graft the specificity of a monoclonal antibody onto a T cell. The receptors are called chimeric because they are composed of parts from different sources.

The terms "protein," "polypeptide," and "peptide" are used interchangeably herein when referring to a gene product.

"Homology," "identity," or "similarity" refers to sequence similarity between two peptides or between two nucleic acid molecules. Identity can be determined by comparing a position in each sequence which may be aligned for purposes of comparison. When a position in the compared sequence is occupied by the same base or amino acid, then the molecules share sequence identity at that position. A degree of identity between sequences is a function of the number of matching or homologous positions shared by the sequences. An "unrelated" or "non-homologous" sequence shares less than 40% identity, or less than 25% identity, with one of the sequences of the current disclosure.

The terms "amino portion," "N-terminus," "amino terminus," and the like as used herein are used to refer to order of the regions of the polypeptide. Furthermore, when something is N-terminal to a region it is not necessarily at the terminus (or end) of the entire polypeptide, but just at the terminus of the region or domain. Similarly, the terms "carboxy portion," "C-terminus," "carboxy terminus," and the like as used herein is used to refer to order of the regions of the polypeptide, and when something is C-terminal to a region it is not necessarily at the terminus (or end) of the entire polypeptide, but just at the terminus of the region or domain.

The terms "polynucleotide," "nucleic acid," and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

The term "subject," "individual," or "patient" is used interchangeably herein and refers to a vertebrate, for example a primate, a mammal or preferably a human. Mammals include, but are not limited to equines, canines, bovines, ovines, murines, rats, simians, humans, farm animals, sport animals and pets.

The term "xeno-free (XF)" or "animal component-free (ACF)" or "animal free," when used in relation to a medium, an extracellular matrix, or a culture condition, refers to a medium, an extracellular matrix, or a culture condition which is essentially free from heterogeneous animal-derived components. For culturing human cells, any proteins of a non-human animal, such as mouse, would be xeno components. In certain aspects, the xeno-free matrix may be essentially free of any non-human animal-derived components, therefore excluding mouse feeder cells or Matrigel™. Matrigel™ is a solubilized basement membrane preparation extracted from the Engelbreth-Holm-Swarm (EHS) mouse sarcoma, a tumor rich in extracellular matrix proteins to include laminin (a major component), collagen IV, heparin sulfate proteoglycans, and entactin/nidogen. In some embodiments, the compositions described herein or cells of the disclosure are cultured in and/or prepared in/with xeno-free or animal component-free or animal free medium.

Cells are "substantially free" of certain reagents or elements, such as serum, signaling inhibitors, animal components or feeder cells, exogenous genetic elements or vector elements, as used herein, when they have less than 10% of the element(s), and are "essentially free" of certain reagents or elements when they have less than 1% of the element(s). However, even more desirable are cell populations wherein less than 0.5% or less than 0.1% of the total cell population comprise exogenous genetic elements or vector elements.

A culture, matrix or medium are "essentially free" of certain reagents or elements, such as serum, signaling inhibitors, animal components or feeder cells, when the culture, matrix or medium respectively have a level of these reagents lower than a detectable level using conventional detection methods known to a person of ordinary skill in the art or these agents have not been extrinsically added to the culture, matrix or medium. The serum-free medium may be essentially free of serum.

A "gene," "polynucleotide," "coding region," "sequence," "segment," "fragment," or "transgene" which "encodes" a particular protein, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "cell" is herein used in its broadest sense in the art and refers to a living body which is a structural unit of tissue of a multicellular organism, is surrounded by a membrane structure which isolates it from the outside, has the capability of self-replicating, and has genetic information and a mechanism for expressing it. Cells used herein may be naturally-occurring cells or artificially modified cells (e.g., fusion cells, genetically modified cells, etc.).

As used herein, the term "stem cell" refers to a cell capable of self-replication and pluripotency or multipotency. Typically, stem cells can regenerate an injured tissue. Stem cells herein may be, but are not limited to, embryonic stem (ES) cells, induced pluripotent stem cells or tissue stem cells (also called tissue-specific stem cell, or somatic stem cell).

"Embryonic stem (ES) cells" are pluripotent stem cells derived from early embryos. An ES cell was first established in 1981, which has also been applied to production of knockout mice since 1989. In 1998, a human ES cell was established, which is currently becoming available for regenerative medicine.

Unlike ES cells, tissue stem cells have a limited differentiation potential. Tissue stem cells are present at particular locations in tissues and have an undifferentiated intracellular structure. Therefore, the pluripotency of tissue stem cells is typically low. Tissue stem cells have a higher nucleus/cytoplasm ratio and have few intracellular organelles. Most tissue stem cells have low pluripotency, a long cell cycle, and proliferative ability beyond the life of the individual. Tissue stem cells are separated into categories, based on the sites from which the cells are derived, such as the dermal system, the digestive system, the bone marrow system, the nervous system, and the like. Tissue stem cells in the dermal system include epidermal stem cells, hair follicle stem cells, and the like. Tissue stem cells in the digestive system include pancreatic (common) stem cells, liver stem cells, and the like. Tissue stem cells in the bone marrow system include hematopoietic stem cells, mesenchymal stem cells, and the like. Tissue stem cells in the nervous system include neural stem cells, retinal stem cells, and the like.

"Induced pluripotent stem cells," commonly abbreviated as iPS cells or iPSCs, refer to a type of pluripotent stem cell artificially prepared from a non-pluripotent cell, typically an adult somatic cell, or terminally differentiated cell, such as fibroblast, a hematopoietic cell, a myocyte, a neuron, an epidermal cell, or the like, by introducing certain factors, referred to as reprogramming factors.

"Pluripotency" refers to a stem cell that has the potential to differentiate into all cells constituting one or more tissues or organs, or particularly, any of the three germ layers: endoderm (interior stomach lining, gastrointestinal tract, the lungs), mesoderm (muscle, bone, blood, urogenital), or ectoderm (epidermal tissues and nervous system). "Pluripotent stem cells" used herein refer to cells that can differentiate into cells derived from any of the three germ layers, for example, direct descendants of totipotent cells or induced pluripotent cells.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

In some embodiments, the methods are useful for reducing the size and/or cell number of a solid tumor. In some embodiments, the method of the disclosure are useful for inhibiting the growth of tumors, such as solid tumors, in a subject.

The term "antigen" refers to any substance that causes an immune system to produce antibodies against it, or to which a T cell responds. In some embodiments, an antigen is a peptide that is 5-50 amino acids in length or is at least, at most, or exactly 5, 10, 15, 20, 25, 30, 35, 40, 45, 50, 55, 60, 65, 70, 75, 80, 85, 90, 95, 100, 125, 150, 175, 200, 250, or 300 amino acids, or any derivable range therein.

The term "antibody" includes monoclonal antibodies, polyclonal antibodies, dimers, multimers, multispecific antibodies and antibody fragments that may be human, mouse, humanized, chimeric, or derived from another species. A "monoclonal antibody" is an antibody obtained from a population of substantially homogeneous antibodies that is being directed against a specific antigenic site.

"Antibody or functional fragment thereof means an immunoglobulin molecule that specifically binds to, or is immunologically reactive with a particular antigen or epitope, and includes both polyclonal and monoclonal antibodies. The term antibody includes genetically engineered or otherwise modified forms of immunoglobulins, such as intrabodies, peptibodies, chimeric antibodies, fully human antibodies, humanized antibodies, and heteroconjugate antibodies (e.g., bispecific antibodies, diabodies, triabodies, and tetrabodies). The term functional antibody fragment includes antigen binding fragments of antibodies, including e.g., Fab', $F(ab')_2$, Fab, Fv, rlgG, and scFv fragments. The term scFv refers to a single chain Fv antibody in which the variable domains of the heavy chain and of the light chain of a traditional two chain antibody have been joined to form one chain.

The use of a single chain variable fragment (scFv) is of particular interest. scFvs are recombinant molecules in which the variable regions of light and heavy immunoglobulin chains encoding antigen-binding domains are engineered into a single polypeptide. Generally, the $V_H$ and $V_L$ sequences are joined by a linker sequence. See, for example, Ahmad (2012) Clinical and Developmental Immunology Article ID 980250, herein specifically incorporated by reference.

A "therapeutically effective amount" or "efficacious amount" refers to the amount of an agent, or combined amounts of two agents, that, when administered to a mammal or other subject for treating a disease, is sufficient to effect such treatment for the disease. The "therapeutically effective amount" will vary depending on the agent(s), the disease and its severity and the age, weight, etc., of the subject to be treated.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

II. Polypeptides

A. Signal Peptides

A "signal peptide" refers to a peptide sequence that directs the transport and localization of the protein within a cell, e.g. to a certain cell organelle (such as the endoplasmic reticulum) and/or the cell surface. A signal peptide directs the nascent protein into the endoplasmic reticulum. This is essential if the receptor is to be glycosylated and anchored in the cell membrane. Generally, the signal peptide natively attached to the amino-terminal most component is used (e.g. in a scFv with orientation light chain-linker-heavy chain, the native signal of the light-chain is used). In some embodiments the signal peptide is SEQ ID NO:18.

In some embodiments, the signal peptide is cleaved after passage of the endoplasmic reticulum (ER), i.e. is a cleavable signal peptide. In some embodiments, a restriction site is at the carboxy end of the signal peptide to facilitate cleavage.

B. Antigen-Binding Domain

The antigen-binding domain is a single-chain variable fragment (scFv) based on TGF-β antibodies. "Single-chain Fv" or "scFv" antibody fragments comprise the VH and VL domains of an antibody, wherein these domains are present in a single polypeptide chain. In some embodiments, the antigen-binding domain further comprises a peptide linker between the $V_H$ and $V_L$ domains, which enables the scFv to form the desired structure for antigen binding.

The variable regions of the antigen-binding domains of the polypeptides of the disclosure can be modified by mutating amino acid residues within the VH and/or VL CDR 1, CDR 2 and/or CDR 3 regions to improve one or more binding properties (e.g., affinity) of the antibody. The term "CDR" refers to a complementarity-determining region that is based on a part of the variable chains in immunoglobulins (antibodies) and T-cell receptors, generated by B cells and T cells respectively, where these molecules bind to their specific antigen. Since most sequence variation associated with immunoglobulins and T-cell receptors are found in the CDRs, these regions are sometimes referred to as hypervariable regions. Mutations may be introduced by site-directed mutagenesis or PCR-mediated mutagenesis and the effect on antibody binding, or other functional property of interest, can be evaluated in appropriate in vitro or in vivo assays. Preferably conservative modifications are introduced and typically no more than one, two, three, four or five residues within a CDR region are altered. The mutations may be amino acid substitutions, additions or deletions.

Framework modifications can be made to the antibodies to decrease immunogenicity, for example, by "backmutating" one or more framework residues to the corresponding germline sequence.

It is also contemplated that the antigen binding domain may be multi-specific or multivalent by multimerizing the antigen binding domain with VH and VL region pairs that bind either the same antigen (multi-valent) or a different antigen (multi-specific).

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more (or any derivable range therein), than the affinity of an antibody for unrelated amino acid sequences. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges.

C. Peptide Spacer

A spacer region links the antigen-binding domain to the transmembrane domain. It should be flexible enough to allow the antigen-binding domain to orient in different directions to facilitate antigen recognition. The simplest form is the hinge region from IgG. Alternatives include the $CH_2CH_3$ region of immunoglobulin and portions of CD3. In some embodiments, the $CH_2CH_3$ region may have L235E/N297Q or L235D/N297Q modifications, or at least 75%, at least 80%, at least 85%, at least 90%, at least 95%, at least 98%, or 100% amino acid sequence identity of the $CH_2CH_3$ region. For most scFv-based constructs, the IgG hinge suffices. However the best spacer often has to be determined empirically. In some embodiments, the spacer is from IgG4.

As used herein, the term "hinge" refers to a flexible polypeptide connector region (also referred to herein as "hinge region" or "spacer") providing structural flexibility and spacing to flanking polypeptide regions and can consist of natural or synthetic polypeptides. A "hinge" derived from an immunoglobulin (e.g., IgGl) is generally defined as stretching from Glu216 to Pro230 of human IgGl (Burton (1985) Molec. Immunol., 22:161-206). Hinge regions of other IgG isotypes may be aligned with the IgGl sequence by placing the first and last cysteine residues forming inter-heavy chain disulfide (S—S) bonds in the same positions. The hinge region may be of natural occurrence or non-natural occurrence, including but not limited to an altered hinge region as described in U.S. Pat. No. 5,677,425. The hinge region can include complete hinge region derived from an antibody of a different class or subclass from that of the $CH_1$ domain. The term "hinge" can also include regions derived from CD8 and other receptors that provide a similar function in providing flexibility and spacing to flanking regions.

The peptide spacer can have a length of at least, at most, or exactly 4, 5, 6, 7, 8, 9, 10, 15, 16, 17, 18, 19, 20, 20, 25, 30, 35, 40, 45, 50, 75, 100, 110, 120, 130, 140, 150, 160, 170, 180, 190, 200, 201, 202, 203, 204, 205, 206, 207, 208, 209, 210, 211, 212, 213, 214, 215, 216, 217, 218, 219, 220, 225, 226, 227, 228, 229, 230, 231, 232, 233, 234, 235, 236, 237, 238, 239, 240, 241, 242, 243, 244, 245, 246, 247, 248, 249, 250, 260, 270, 280, 290, 300, 325, 350, or 400 amino acids (or any derivable range therein). In some embodiments, the peptide spacer consists of or comprises a hinge region from an immunoglobulin. Immunoglobulin hinge region amino acid sequences are known in the art; see, e.g., Tan et al. (1990) Proc. Natl. Acad. Sci. USA 87:162; and Huck et al. (1986) Nucl. Acids Res.

The length of a peptide spacer may have effects on the response to TGF-β and/or expansion properties. In some embodiments, a shorter spacer such as less than 50, 45, 40, 30, 35, 30, 25, 20, 15, or 10 amino acids may have the advantage of a decrease in the concentration of TGF-β required for an effective activation response. In some embodiments, a longer spacer, such as one that is at least 50, 60, 70, 80, 90, 100, 110, 120, 130, 140, 150, 200, 201, 202, 203, 204, 205, 206, 207, 208, 209, 210, 211, 212, 213, 214, 215, 216, 217, 218, 219, 220, 225, 226, 227, 228, 229, 230, 231, 232, 233, 234, 235, 236, 237, 238, 239, 240, 241, 242, 243, 244, 245, 246, 247, 248, 249, 250, 260, 270, 280, or 290 amino acids may have the advantage of increased expansion in vivo or in vitro.

As non-limiting examples, an immunoglobulin hinge region can include one of the following amino acid sequences: DKTHT (SEQ ID NO:27); CPPC (SEQ ID NO:28); CPEPKSCDTPPPCPR (SEQ ID NO:29); ELKTPLGDTTHT (SEQ ID NO:30); KSCDKTHTCP (SEQ ID NO:31); KCCVDCP (SEQ ID NO:32); KYGPPCP (SEQ ID NO: 33); EPKSCDKTHTCPPCP (SEQ ID NO:34) (human IgG1 hinge); ERKCCVECPPCP (SEQ ID NO:35) (human IgG2 hinge); ELKTPLGDTTHTCPRCP (SEQ ID NO:36) (human IgG3 hinge); SPNMVPHAHHAQ (SEQ ID NO:37); ESKYGPPCPPCP (SEQ ID NO:98) or ESKYGPPCPSCP (SEQ ID NO:99) (human IgG4 hinge-based) and the like. In some embodiments, the hinge is SEQ ID NO:98 or SEQ ID NO:99. In some embodiments, the hinge is SEQ ID NO:99.

The hinge region can comprise an amino acid sequence of a human IgG1, IgG2, IgG3, or IgG4, hinge region. The hinge region can include one or more amino acid substitutions and/or insertions and/or deletions compared to a wild-type (naturally-occurring) hinge region. For example, His229 of human IgG1 hinge can be substituted with Tyr, so that the hinge region comprises the sequence EPKSCDKTYTCPPCP (SEQ ID NO:38).

The hinge region can comprise an amino acid sequence derived from human CD8; e.g., the hinge region can comprise the amino acid sequence: TTTPAPRPPTPAPTIASQPLSLRPEACRPAAGGAVHTRGLDFACD (SEQ ID NO:39), or a variant thereof.

D. Transmembrane Domain

The transmembrane domain is a hydrophobic alpha helix that spans the membrane. Generally, the transmembrane domain from the most membrane proximal component of the endodomain is used. Different transmembrane domains result in different receptor stability.

The transmembrane domain is interposed between the peptide spacer and the endodomain. In some embodiments, the transmembrane domain is interposed between the peptide spacer and a co-stimulatory region. In some embodiments, a linker is between the transmembrane domain and a co-stimulatory region or endodomain.

Any transmembrane domain that provides for insertion of a polypeptide into the cell membrane of a eukaryotic (e.g., mammalian) cell is suitable for use. As one non-limiting example, the transmembrane sequence IYIWAPLAGTCGVLLLSLVITLYC (SEQ ID NO: 48) can be used. In some embodiments, the transmembrane domain is CD8 beta derived: LGLLVAGVLVLLVSLGVAIHLCC (SEQ ID NO:49); CD4 derived: ALIVLGGVAGLLLFIGLGIFFCVRC (SEQ ID NO:50); CD3 zeta derived: LCYLLDGILFIYGVILTALFLRV (SEQ ID NO:51); CD28 derived: WVLVVVGGVLACYSLLVTVAFIIFWV (SEQ ID NO:52); CD134 (OX40) derived: VAAILGLGLVLGLLGPLAILLALYLL (SEQ ID NO:53); or CD7 derived: ALPAALAVISFLLGLGLGVACVLA (SEQ ID NO:54).

E. Endodomain

After antigen recognition, receptors cluster and a signal is transmitted to the cell through the endodomain and/or co-stimulatory domain. In some embodiments, the co-stimulatory domains described herein are part of the endodomain. The most commonly used endodomain component is CD3-zeta, which contains 3 ITAMs. This transmits an activation signal to the T cell after antigen is bound. CD3-zeta may not provide a fully competent activation signal and additional co-stimulatory signaling is needed. For example, chimeric CD28 and OX40 can be used with CD3-Zeta to transmit a proliferative/survival signal, or all three can be used together.

Further endodomains suitable for use in the polypeptides of the disclosure include any desired signaling domain that provides a distinct and detectable signal (e.g., increased production of one or more cytokines by the cell; change in transcription of a target gene; change in activity of a protein; change in cell behavior, e.g., cell death; cellular proliferation; cellular differentiation; cell survival; modulation of cellular signaling responses; etc.) in response to activation by way of binding of the antigen to the antigen binding domain. In some embodiments, the endodomain includes at least one (e.g., one, two, three, four, five, six, etc.) ITAM motif as described herein. In some embodiments, the endodomain includes DAP10/CD28 type signaling chains.

Endodomains suitable for use in the polypeptides of the disclosure include immunoreceptor tyrosine-based activation motif (ITAM)-containing intracellular signaling polypeptides. An ITAM motif is $YX_1X_2(L/I)$, where $X_1$ and $X_2$ are independently any amino acid (SEQ ID NO:64). In some cases, the endodomain comprises 1, 2, 3, 4, or 5 ITAM motifs. In some cases, an ITAM motif is repeated twice in an endodomain, where the first and second instances of the ITAM motif are separated from one another by 6 to 8 amino acids, e.g., $(YX_1X_2(L/I))(X_3)_n(YX_1X_2(L/I))$, where n is an integer from 6 to 8, and each of the 6-8 $X_3$ can be any amino acid (SEQ ID NO:65).

A suitable endodomain may be an ITAM motif-containing portion that is derived from a polypeptide that contains an ITAM motif. For example, a suitable endodomain can be an ITAM motif-containing domain from any ITAM motif-containing protein. Thus, a suitable endodomain need not contain the entire sequence of the entire protein from which it is derived. Examples of suitable ITAM motif-containing polypeptides include, but are not limited to: DAP12; FCER1G (Fc epsilon receptor I gamma chain); CD3D (CD3 delta); CD3E (CD3 epsilon); CD3G (CD3 gamma); CD3Z (CD3 zeta); and CD79A (antigen receptor complex-associated protein alpha chain).

In some cases, the endodomain is derived from DAP12 (also known as TYROBP; TYRO protein tyrosine kinase binding protein; KARAP; PLOSL; DN AX-activation protein 12; KAR-associated protein; TYRO protein tyrosine kinase-binding protein; killer activating receptor associated protein; killer-activating receptor-associated protein; etc.). For example, a suitable endodomain polypeptide can comprise an amino acid sequence having at least 75%, at least 80%, at least 85%, at least 90%, at least 95%, at least 98%, or 100%, amino acid sequence to identity (SEQ ID NO: 66)

```
MGGLEPCSRLLLLPLLLAVSGLRPVQAQAQSDCSCSTVSPGVLAGIVMG

DLVLTVLIALAVYFLGRLVPRGRGAAEAATRKQRITETESPYQELQGQR

SDVYSDLNTQRPYYK;
```

-continued (SEQ ID NO: 67)
MGGLEPCSRLLLLPLLLAVSGLRPVQAQAQSDCSCSTVSPGVLAGIVMG

DLVLTVLIALAVYFLGRLVPRGRGAAEATRKQRITETESPYQELQGQRS

DVYSDLNTQRPYYK;

(SEQ ID NO: 68)
MGGLEPCSRLLLLPLLLAVSDCSCSTVSPGVLAGIVMGDLVLTVLIALA

VYFLGRLVPRGRGAAEAATRKQRITETESPYQELQGQRSDVYSDLNTQR

PYYK; or (SEQ ID NO: 69)
MGGLEPCSRLLLLPLLLAVSDCSCSTVSPGVLAGIVMGDLVLTVLIALA

VYFLGRLVPRGRGAAEATRKQRITETESPYQELQGQRSDVYSDLNTQRP

YYK.

In some embodiments, a suitable endodomain polypeptide can comprise an ITAM motif-containing portion of the full length DAP12 amino acid sequence. Thus, a suitable endodomain polypeptide can comprise an amino acid sequence having at least 75%, at least 80%, at least 85%, at least 90%, at least 95%, at least 98%, or 100%, amino acid sequence identity to ESPYOELOGORSDVYSDLNTO (SEQ ID NO: 70).

In some embodiments, the endodomain is derived from FCER1G (also known as FCRG; Fc epsilon receptor I gamma chain; Fc receptor gamma-chain; fc-epsilon Rl-gamma; fcRgamma; fceRI gamma; high affinity immunoglobulin epsilon receptor subunit gamma; immunoglobulin E receptor, high affinity, gamma chain; etc.). For example, a suitable endodomain polypeptide can comprise an amino acid sequence having at least 75%, at least 80%, at least 85%, at least 90%, at least 95%, at least 98%, or 100% amino acid sequence identity to (SEQ ID NO: 71)
MIPAVVLLLLLLLVEQAAALGEPQLCYILDAILFLYGIVLTLLYCRLKIQ
VRKAAITSYEKSDGVYTGLSTRNQETYETLKHEKPPQ.

In some embodiments, a suitable endodomain polypeptide can comprise an ITAM motif-containing portion of the full length FCER1G amino acid sequence. Thus, a suitable endodomain polypeptide can comprise an amino acid sequence having at least 75%, at least 80%, at least 85%, at least 90%, at least 95%, at least 98%, or 100%, amino acid sequence identity to DGVYTGLSTRNOETYETLKHE (SEQ ID NO: 72).

In some embodiments, the endodomain is derived from T-cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T-cell receptor T3 delta chain; T-cell surface glycoprotein CD3 delta chain; etc.). For example, a suitable endodomain polypeptide can comprise an amino acid sequence having at least 75%, at least 80%, at least 85%, at least 90%, at least 95%, at least 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 170 aa, of either of the following amino acid sequences (2 isoforms):

(SEQ ID NO: 73)
MEHSTFLSGLVLATLLSQVSPFKIPIEELEDRVFVNCNTSITWVEGTVG

TLLSDITRLDLGKRILDPRGIYRCNGTDIYKDKESTVQVHYRMCQSCVE

LDPATVAGIIVTDVIATLLLALGVFCFAGHETGRLSGAADTQALLRNDQ

VYQPLRDRDDAQYSHLGGNWARNK
or (SEQ ID NO: 74)
MEHSTFLSGLVLATLLSQVSPFKIPIEELEDRVFVNCNTSITWVEGTVG

TLLSDITRLDLGKRILDPRGIYRCNGTDIYKDKESTVQVHYRTADTQAL

LRNDQVYQPLRDRDDAQYSHLGGNWARNK.

In some embodiments, a suitable endodomain polypeptide can comprise an ITAM motif-containing portion of the full length CD3 delta amino acid sequence. Thus, a suitable endodomain polypeptide can comprise an amino acid sequence having at least 75%, at least 80%, at least 85%, at least 90%, at least 95%, at least 98%, or 100%, amino acid sequence identity to DOVYOPLRDRDDAOYSHLGGN (SEQ ID NO:75).

In some embodiments, the endodomain is derived from T-cell surface glycoprotein CD3 epsilon chain (also known as CD3e, T-cell surface antigen T3/Leu-4 epsilon chain, T-cell surface glycoprotein CD3 epsilon chain, AI504783, CD3, CD3epsilon, T3e, etc.). For example, a suitable endodomain polypeptide can comprise an amino acid sequence having at least 75%, at least 80%, at least 85%, at least 90%, at least 95%, at least 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 205 aa, of the following amino acid sequence:

(SEQ ID NO: 76)
MQSGTHWRVLGLCLLSVGVWGQDGNEEMGGITQTPYKVSISGTTVILTCP

QYPGSEILWQHNDKNIGGDEDDKNIGSDEDHLSLKEFSELEQSGYYVCYP

RGSKPEDANFYLYLRARVCENCMEMDVMSVATIVIVDICITGGLLLLVYY

WSKNRKAKAKPVTRGAGAGGRQRGQNKERPPPVPNPDYEPIRKGQRDLYS

GLNQRRI.

In some embodiments, a suitable endodomain polypeptide can comprise an ITAM motif-containing portion of the full length CD3 epsilon amino acid sequence. Thus, a suitable endodomain polypeptide can comprise an amino acid sequence having at least 75%, at least 80%, at least 85%, at least 90%, at least 95%, at least 98%, or 100%, amino acid sequence identity to NPDYEPIRKGQRDLYSGLNQR (SEQ ID NO:77).

In some embodiments, the endodomain is derived from T-cell surface glycoprotein CD3 gamma chain (also known as CD3G, T-cell receptor T3 gamma chain, CD3-GAMMA, T3G, gamma polypeptide (TiT3 complex), etc.). For example, a suitable endodomain polypeptide can comprise an amino acid sequence having at least 75%, at least 80%, at least 85%, at least 90%, at least 95%, at least 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 180 aa, of the following amino acid sequence:

(SEQ ID NO: 78)
MEQGKGLAVLILAIILLQGTLAQSIKGNHLVKVYDYQEDGSVLLTCDAEA
KNITWFKDGKMIGFLTEDKKKWNLGSNAKDPRGMYQCKGSQNKSKPLQVY
YRMCQNCIELNAATISGFLFAEIVSIFVLAVGVYFIAGODGVROSRASDK
OTLLPNDOLYOPLKDREDDQYSHLQGNQLRRN.

In some embodiments, a suitable endodomain polypeptide can comprise an ITAM motif-containing portion of the full length CD3 gamma amino acid sequence. Thus, a suitable endodomain polypeptide can comprise an amino acid sequence having at least 75%, at least 80%, at least 85%, at least 90%, at least 95%, at least 98%, or 100%, amino acid sequence identity to DOLYOPLKDREDDOYSHLOGN (SEQ ID NO:79).

In some embodiments, the endodomain is derived from T-cell surface glycoprotein CD3 zeta chain (also known as CD3Z, T-cell receptor T3 zeta chain, CD247, CD3-ZETA, CD3H, CD3Q, T3Z, TCRZ, etc.). For example, a suitable intracellular signaling domain polypeptide can comprise an amino acid sequence having at least 75%, at least 80%, at least 85%, at least 90%, at least 95%, at least 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences (2 isoforms):

(SEQ ID NO: 80)
MKWKALFTAAILQAQLPITEAQSFGLLDPKLCYLLDGILFIYGVILTALF
LRVKFSRSADAPAYQQGQNQLYNELNLGRREEYDVLDKRRGRDPEMGGKP
RRKNPQEGLYNELOKDKMAEAYSEIGMKGERRRGKGHDGLYOGLSTATKD
TYDALHMQALPPR
or (SEQ ID NO: 81)
MKWKALFTAAILQAQLPITEAQSFGLLDPKLCYLLDGILFIYGVILTALF
LRVKFSRSADAPAYQQGQNQLYNELNLGRREEYDVLDKRRGRDPEMGGKP
QRRKNPQEGLYNELOKDKMAEAYSEIGMKGERRRGKGHDGLYOGLSTATK
DTYDALHMQALPPR.

In some embodiments, a suitable endodomain polypeptide can comprise an ITAM motif-containing portion of the full length CD3 zeta amino acid sequence. Thus, a suitable endodomain polypeptide can comprise an amino acid sequence having at least 75%, at least 80%, at least 85%, at least 90%, at least 95%, at least 98%, or 100%, amino acid sequence identity to any of amino the following acid sequences:

(SEQ ID NO: 82)
RVKFSRSADAPAYOQGONOLYNELNLGRREEYDVLDKRRGRDPEMGGKP
RRKNPOEGLYNELOKDKMAEAYSEIGMKGERRRGKGHDGLYOGLSTATK
DTYDALHMQALPPR;

-continued (SEQ ID NO: 83)
NOLYNELNLGRREEYDVLDKR;

(SEQ ID NO: 84)
EGLYNELQKDKMAEAYSEIGMK;
or (SEQ ID NO: 85)
DGLYOGLSTATKDTYDALHMO.

In some embodiments, the endodomain is derived from CD79A (also known as B-cell antigen receptor complex-associated protein alpha chain; CD79a antigen (immunoglobulin-associated alpha); MB-1 membrane glycoprotein; ig-alpha; membrane-bound immunoglobulin-associated protein; surface IgM-associated protein; etc.). For example, a suitable endodomain polypeptide can comprise an amino acid sequence having at least 75%, at least 80%, at least 85%, at least 90%, at least 95%, at least 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 150 aa, from about 150 aa to about 200 aa, or from about 200 aa to about 220 aa, of either of the following amino acid sequences (2 isoforms):

(SEQ ID NO: 86)
MPGGPGVLQALPATIFLLFLLSAVYLGPGCQALWMHKVPASLMVSLGED
AHFQCPHNSSNNANVTWWRVLHGNYTWPPEFLGPGEDPNGTLIIQNVNK
SHGGIYVCRVQEGNESYQQSCGTYLRVRQPPPRPFLDMGEGTKNRIITA
EGIILLFCAVVPGTLLLFRKRWONEKLGLDAGDEYEDENLYEGLNLDDC
SMYEDISRGLOGTYQDVGSLNIGDVQLEKP;
or (SEQ ID NO: 87)
MPGGPGVLQALPATIFLLFLLSAVYLGPGCQALWMHKVPASLMVSLGED
AHFQCPHNSSNNANVTWWRVLHGNYTWPPEFLGPGEDPNEPPPRPFLDM
GEGTKNRIITAEGIILLFCAVVPGTLLLFRKRWQNEKLGLDAGDEYEDE
NLYEGLNLDDCSMYEDISRGLQGTYQDVGSLNIGDVQLEKP.

In some embodiments, a suitable endodomain polypeptide can comprise an ITAM motif-containing portion of the full length CD79A amino acid sequence. Thus, a suitable endodomain polypeptide can comprise an amino acid sequence having at least 75%, at least 80%, at least 85%, at least 90%, at least 95%, at least 98%, or 100%, amino acid sequence identity to the following amino acid sequence: ENLYEGLNLDDCSMYEDISRG (SEQ ID NO: 88).

In some embodiments, suitable endodomains can comprise a DAP10/CD28 type signaling chain. An example of a DAP 10 signaling chain is the amino acid sequence: RPRRSPAQDGKVYINMPGRG (SEQ ID NO:89). In some embodiments, a suitable endodomain comprises an amino acid sequence having at least 85%, at least 90%, at least 95%, at least 98%, or at least 99%, amino acid sequence identity to the entire length of the amino acid sequence RPRRSPAQDGKVYINMPGRG (SEQ ID NO:90).

An example of a CD28 signaling chain is the amino acid sequence FWVLVVVGGVLACYSLLVTVAFIIFWVRSKRSRLLHSDYMNMTPRRPGPTRKHYQP YAPPRDFAAYRS (SEQ ID NO:91). In some embodiments, a suitable endodomain comprises an amino acid sequence having at least 85%, at least 90%, at least 95%, at least 98%, or at least 99%, amino acid sequence identity to the entire length of the amino acid sequence (SEQ ID NO: 92)
FWVLVVVGGVLACYSLLVTVAFIIFWVRSKRSRLLHSDYMNMTPRRPGPT
RKHYQPYAPPRDFAAYRS.

Further endodomains suitable for use in the polypeptides of the disclosure include a ZAP70 polypeptide, e.g., a polypeptide comprising an amino acid sequence having at least 85%, at least 90%, at least 95%, at least 98%, at least 99%, or 100%, amino acid sequence identity to a contiguous stretch of from about 300 amino acids to about 400 amino acids, from about 400 amino acids to about 500 amino acids, or from about 500 amino acids to 619 amino acids, of the following amino acid sequence:

(SEQ ID NO: 93)
MPDPAAHLPFFYGSISRAEAEEHLKLAGMADGLFLLRQCLRSLGGYVLS

LVHDVRFHHFPIERQLNGTYAIAGGKAHCGPAELCEFYSRDPDGLPCNL

RKPCNRPSGLEPQPGVFDCLRDAMVRDYVRQTWKLEGEALEQAIISQAP

QVEKLIATTAHERMPWYHSSLTREEAERKLYSGAQTDGKFLLRPRKEQG

TYALSLIYGKTVYHYLISQDKAGKYCIPEGTKFDTLWQLVEYLKLKADG

LIYCLKEACPNSSASNASGAAAPTLPAHPSTLTHPQRRIDTLNSDGYTP

EPARITSPDKPRPMPMDTSVYESPYSDPEELKDKKLFLKRDNLLIADIE

LGCGNFGSVRQGVYRMRKKQIDVAIKVLKQGTEKADTEEMMREAQIMHQ

LDNPYIVRLIGVCQAEALMLVMEMAGGGPLHKFLVGKREEIPVSNVAEL

LHQVSMGMKYLEEKNFVHRDLAARNVLLVNRHYAKISDFGLSKALGADD

SYYTARSAGKWPLKWYAPECINFRKFSSRSDVWSYGVTMWEALSYGQKP

YKKMKGPEVMAFIEQGKRMECPPECPPELYALMSDCWIYKWEDRPDFLT

VEQRMRACYYSLASKVEGPPGSTQKAEAACA.

F. Detection Peptides

Suitable detection peptides include hemagglutinin (HA; e.g., YPYDVPDYA (SEQ ID NO:94); FLAG (e.g., DYKDDDDK (SEQ ID NO:17); c-myc (e.g., EQKLISEEDL; SEQ ID NO:95), and the like. Other suitable detection peptides are known in the art.

G. Peptide Linkers

In some embodiments, the polypeptides of the disclosure include peptide linkers (sometimes referred to as a linker). A peptide linker may be separating any of the peptide domain/regions described herein. As an example, a linker may be between the signal peptide and the antigen binding domain, between the VH and VL of the antigen binding domain, between the antigen binding domain and the peptide spacer, between the peptide spacer and the transmembrane domain, flanking the co-stimulatory region or on the N- or C-region of the co-stimulatory region, and/or between the transmembrane domain and the endodomain. The peptide linker may have any of a variety of amino acid sequences. Domains and regions can be joined by a peptide linker that is generally of a flexible nature, although other chemical linkages are not excluded. A linker can be a peptide of between about 6 and about 40 amino acids in length, or between about 6 and about 25 amino acids in length. These linkers can be produced by using synthetic, linker-encoding oligonucleotides to couple the proteins.

Peptide linkers with a degree of flexibility can be used. The peptide linkers may have virtually any amino acid sequence, bearing in mind that suitable peptide linkers will have a sequence that results in a generally flexible peptide. The use of small amino acids, such as glycine and alanine, are of use in creating a flexible peptide. The creation of such sequences is routine to those of skill in the art.

Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, $(GSGGS)_n$ (SEQ ID NO:40) and $(GGGS)_n$ (SEQ ID NO: 41), where n is an integer of at least one, glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains. Exemplary spacers can comprise amino acid sequences including, but not limited to, GGSG (SEQ ID NO:42), GGSGG (SEQ ID NO:43), GSGSG (SEQ ID NO:44), GSGGG (SEQ ID NO:45), GGGSG (SEQ ID NO:46), GSSSG (SEQ ID NO:47), and the like.

H. Co-Stimulatory Region

Non-limiting examples of suitable co-stimulatory regions include, but are not limited to, polypeptides from 4-1BB (CD137), CD28, ICOS, OX-40, BTLA, CD27, CD30, GITR, and HVEM.

A co-stimulatory region may have a length of at least, at most, or exactly 20, 25, 30, 35, 40, 50, 60, 70, 80, 90, 100, 150, 200, or 300 amino acids or any range derivable therein. In some embodiments, the co-stimulatory region is derived from an intracellular portion of the transmembrane protein 4-1BB (also known as TNFRSF9; CD137; 4-1BB; CDw137; ILA; etc.). For example, a suitable co-stimulatory region can comprise an amino acid sequence having at least 75%, at least 80%, at least 85%, at least 90%, at least 95%, at least 98%, or 100% amino acid sequence identity to (SEQ ID NO: 55)
KRGRKKLLYIFKQPFMRPVQTTQEEDGCCRFPEEEEGGCEL.

In some embodiments, the co-stimulatory region is derived from an intracellular portion of the transmembrane protein CD28 (also known as Tp44). For example, a suitable co-stimulatory region can comprise an amino acid sequence having at least 75%, at least 80%, at least 85%, at least 90%, at least 95%, at least 98%, or 100% amino acid sequence identity to FWVRSKRSRLLHSDYMNMTPRRPGPTRKHYQPYAPPRDFAAYRS (SEQ ID NO: 56).

In some embodiments, the co-stimulatory region is derived from an intracellular portion of the transmembrane protein ICOS (also known as AILIM, CD278, and CVID1). For example, a suitable co-stimulatory region can comprise an amino acid sequence having at least 75%, at least 80%, at least 85%, at least 90%, at least 95%, at least 98%, or 100% amino acid sequence identity to TKKKYSSSVHDPNGEYMFMRAVNTAKKSRLTDVTL (SEQ ID NO: 57).

In some embodiments, the co-stimulatory region is derived from an intracellular portion of the transmembrane protein OX-40 (also known as TNFRSF4, RP5-902P8.3, ACT35, CD134, OX40, TXGP1L). For example, a suitable co-stimulatory region can comprise an amino acid sequence having at least 75%, at least 80%, at least 85%, at least 90%, at least 95%, at least 98%, or 100% amino acid sequence identity to

```
                                    (SEQ ID NO: 58)
RRDQRLPPDAHKPPGGGSFRTPIQEEQADAHSTLAKI.
```

In some embodiments, the co-stimulatory region is derived from an intracellular portion of the transmembrane protein BTLA (also known as BTLA1 and CD272). For example, a suitable co-stimulatory region can comprise an amino acid sequence having at least 75%, at least 80%, at least 85%, at least 90%, at least 95%, at least 98%, or 100% amino acid to sequence identity

```
                                    (SEQ ID NO: 59)
CCLRRHQGKQNELSDTAGREINLVDAHLKSEQTEASTRQNSQVLLSETGI

YDNDPDLCFRIVIQEGSEVYSNPCLEENKPGIVYASLNHSVIGPNSRLAR

NVKEAPTEYASICVRS.
```

In some embodiments, the co-stimulatory region is derived from an intracellular portion of the transmembrane protein CD27 (also known as S 152, T14, TNFRSF7, and Tp55). For example, a suitable co-stimulatory region can comprise an amino acid sequence having at least 75%, at least 80%, at least 85%, at least 90%, at least 95%, at least 98%, or sequence identity to 100% amino acid

```
                                    (SEQ ID NO: 60)
HQRRKYRSNKGESPVEPAEPCRYSCPREEEGSTIPIQEDYRKPEPACS
P.
```

In some embodiments, the co-stimulatory region is derived from an intracellular portion of the transmembrane protein CD30 (also known as TNFRSF8, D1S166E, and Ki-1). For example, a suitable co-stimulatory region can comprise an amino acid sequence having at least 75%, at least 80%, at least 85%, at least 90%, at least 95%, at least 98%, or 100% amino acid to sequence identity

```
                                    (SEQ ID NO: 61)
RRACRKRIRQKLHLCYPVQTSQPKLELVDSRPRRSSTQLRSGASVTEPVA

EERGLMSQPLMETCHSVGAAYLESLPLQDASPAGGPSSPRDLPEPRVSTE

HTNNKIEKIYIMKADTVIVGTVKAELPEGRGLAGPAEPELEEELEADHTP

HYPEQETEPPLGSCSDVMLSVEEEGKEDPLPTAASGK.
```

In some embodiments, the co-stimulatory region is derived from an intracellular portion of the transmembrane protein GITR (also known as TNFRSF18, RP5-902P8.2, AITR, CD357, and GITR-D). For example, a suitable co-stimulatory region can comprise an amino acid sequence having at least 75%, at least 80%, at least 85%, at least 90%, at least 95%, at least 98%, or 100% amino acid sequence identity to

```
                                    (SEQ ID NO: 62)
HIWQLRSQCMWPRETQLLLEVPPSTEDARSCQFPEEERGERSAEEKGRL
GDLWV.
```

In some embodiments, the co-stimulatory region derived from an intracellular portion of the transmembrane protein HVEM (also known as TNFRSF14, RP3-395M20.6, ATAR, CD270, HVEA, HVEM, LIGHTR, and TR2). For example, a suitable co-stimulatory region can comprise an amino acid sequence having at least 75%, at least 80%, at least 85%, at least 90%, at least 95%, at least 98%, or 100% amino acid sequence identity to

```
                                    (SEQ ID NO: 63)
CVKRRKPRGDVVKVIVSVQRKRQEAEGEATVIEALQAPPDVTTVAVEET
IPSFTGRSPNH.
```

I. Additional Modifications

Additionally, the polypeptides of the disclosure may be chemically modified. Glycosylation of the polypeptides can be altered, for example, by modifying one or more sites of glycosylation within the polypeptide sequence to increase the affinity of the polypeptide for antigen (U.S. Pat. Nos. 5,714,350 and 6,350,861).

The polypeptides of the invention can be pegylated to increase biological half-life by reacting the polypeptide with polyethylene glycol (PEG) or a reactive ester or aldehyde derivative of PEG, under conditions in which one or more PEG groups become attached to the polypeptide. Polypeptide pegylation may be carried out by an acylation reaction or an alkylation reaction with a reactive PEG molecule (or an analogous reactive water soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. Methods for pegylating proteins are known in the art and can be applied to the polypeptides of the invention (EP 0 154 316 and EP 0 401 384).

Additionally, polypeptides may be chemically modified by conjugating or fusing the polypeptide to serum protein, such as human serum albumin, to increase half-life of the resulting molecule. Such approach is for example described in EP 0322094 and EP 0 486 525.

The polypeptides of the disclosure may be conjugated to a diagnostic or therapeutic agent and used diagnostically, for example, to monitor the development or progression of a disease and determine the efficacy of a given treatment regimen. The polypeptides may also be conjugated to a therapeutic agent to provide a therapy in combination with the immunostimulating effect of the polypeptide. Examples of diagnostic agents include enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the polypeptide, or indirectly, through a linker using techniques known in the art. Examples of suitable enzymes include horseradish peroxidase, alkaline phosphatase, beta-galactosidase, or acetylcholinesterase. Examples of suitable prosthetic group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. An example of a luminescent material includes luminol. Examples of bioluminescent materials include luciferase, luciferin, and aequorin. Examples of suitable radioactive material include .sup.125I, .sup.131I, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-111, Gallium-67, Praseodymium-142, Samarium-153, Terbium-161, Dysprosium-166, Holmium-166, Rhenium-186, Ithenium-188, Rhenium-189, Lead-212, Radium-223, Actinium-225, Iron-59, Selenium-75, Arsenic-77, Strontium-89, Molybdenum-99, Rhodium-1105, Palladium-109, Praseodymium-143, Promethium-149, Erbium-169, Iridium-194, Gold-198, Gold-199, and Lead-211. Chelating agents may be attached through amities (Meares et al., 1984 Anal. Biochem. 142: 68-78); sulfhydral groups (Koyama 1994 Chem. Abstr. 120: 217262t) of amino acid residues and carbohydrate groups (Rodwell et al. 1986 PNAS USA 83:2632-2636; Quadri et al. 1993 Nucl. Med. Biol. 20:559-570).

The polypeptides may also be conjugated to a therapeutic agent to provide a therapy in combination with the immunostimulating effect of the polypeptide.

Additional suitable conjugated molecules include ribonuclease (RNase), DNase I, an antisense nucleic acid, an inhibitory RNA molecule such as a siRNA molecule, an immunostimulatory nucleic acid, aptamers, ribozymes, triplex forming molecules, and external guide sequences. Aptamers are small nucleic acids ranging from 15-50 bases in length that fold into defined secondary and tertiary structures, such as stern-loops or G-quartets, and can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Ribozymes are nucleic acid molecules that are capable of catalyzing a chemical reaction, either intramolecularly or intermolecularly. Ribozymes typically cleave nucleic acid substrates through recognition and binding of the target substrate with subsequent cleavage. Triplex forming function nucleic acid molecules can interact with double-stranded or single-stranded nucleic acid by forming a triplex, in which three strands of DNA form a complex dependent on both Watson-Crick and Hoogsteen base-pairing. Triplex molecules can bind target regions with high affinity and specificity.

The functional nucleic acid molecules may act as effectors, inhibitors, modulators, and stimulators of a specific activity possessed by a target molecule, or the functional nucleic acid molecules may possess a de novo activity independent of any other molecules.

J. Cancer-Specific Chimeric Antigen Receptors

In some embodiments, the cells may further comprise a cancer-specific chimeric antigen receptor (CAR). The term "cancer-specific" in the context of CARs refers to CARs that have an antigen binding specificity for a cancer-specific molecule, such as a cancer-specific antigen. In some embodiments, the cancer specific CAR is in a cell with a TGF-β CAR. In some embodiments, the cancer-specific CAR and TGF-β care are on separate polypeptides. In some embodiments, the CAR is a bi-specific CAR that has antigen binding for a cancer-specific molecule and for TGF-β. For example, a bi-specific CAR may have a signaling peptide, a cancer molecule-specific scFv, optionally a peptide linker/spacer, followed by a TGF-β scFv, followed by a spacer, a transmembrane domain, and a costimulatory domain. In some embodiments, the bi-specific CAR comprises one or more additional peptide segments described herein.

In some embodiments, polypeptides of the disclosure may comprise a CD20 scFv. An exemplary CD20 scFv comprises the following:

```
                                        (SEQ ID NO: 100)
DIVLTQSPAILSASPGEKVTMTCRASSSVNYMDWYQKKPGSSPKPWIYA

TSNLASGVPARFSGSGSGTSYSLTISRVEAEDAATYYCQQWSFNPPTFG

GGTKLEIKGSTSGGGSGGGSGGGGSSEVQLQQSGAELVKPGASVKMSCK

ASGYTFTSYNMHVWKQTPGQGLEWIGAIYPGNGDTSYNQKFKGKATLTA

DKSSSTAYMQLSSLTSEDSADYYCARSNYYGSSYWFFDVWGAGTTVTVS

S.
```

In some embodiments, polypeptides of the disclosure may comprise a CD19 scFv. An exemplary CD19 scFv comprises the following:

```
                                        (SEQ ID NO: 101)
DIQMTQTTSSLSASLGDRVTISCRASQDISKYLNWYQQKPDGTVKLLIYH

TSRLHSGVPSRFSGSGSGTDYSLTISNLEQEDIATYFCQQGNTLPYTFGG

GTKLEITGSTSGSGKPGSGEGSTKGEVKLQESGPGLVAPSQSLSVTCTVS

GVSLPDYGVSWIRQPPRKGLEWLGVIWGSETTYYNSALKSRLTIIKDNSK

SQVFLKMNSLQTDDTAIYYCAKHYYYGGSYAMDYWGQGTSVTVSS
```

Other cancer-specific molecules (in addition to CD19 and CD20) can include CAIX, CD33, CD44v7/8, CEA, EGP-2, EGP-40, erb-B2, erb-B3, erb-B4, FBP, fetal acetylcholine receptor, GD2, GD3, Her2/neu, IL-13R-a2, KDR, k-light chain, LeY, L1 cell adhesion molecule, MAGE-A1, mesothelin, MUC1, NKG2D ligands, oncofetal antigen (h5T4), PSCA, PSMA, TAA targeted by mAb IgE, TAG-72, and VEGF-R2. In some embodiments, the cancer-specific molecule comprises Her2.

III. Cells

Certain embodiments relate to cells comprising polypeptides or nucleic acids of the disclosure. In some embodiments the cell is an immune cell or a T cell. "T cell" includes all types of immune cells expressing CD3 including T-helper cells ($CD4^+$ cells), cytotoxic T-cells ($CD8^+$ cells), T-regulatory cells (Treg) and gamma-delta T cells. A "cytotoxic cell" includes $CD8^+$ T cells, natural-killer (NK) cells, and neutrophils, which cells are capable of mediating cytotoxicity responses.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), human embryonic kidney (HEK) 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RATI cells, mouse L cells (ATCC No. CCLI.3), HLHepG2 cells, Hut-78, Jurkat, HL-60, NK cell lines (e.g., NKL, NK92, and YTS), and the like.

In some instances, the cell is not an immortalized cell line, but is instead a cell (e.g., a primary cell) obtained from an individual. For example, in some cases, the cell is an immune cell obtained from an individual. As an example, the cell is a T lymphocyte obtained from an individual. As another example, the cell is a cytotoxic cell obtained from an individual. As another example, the cell is a stem cell or progenitor cell obtained from an individual.

IV. Methods

Aspects of the current disclosure relate to methods for stimulating an immune response. The immune response stimulation may be done in vitro, in vivo, or ex vivo. In some embodiments, the methods relate to cells capable of stimulating an immune response in the presence of TGF-β. The method generally involves genetically modifying a mammalian cell with an expression vector, or an RNA (e.g., in vitro transcribed RNA), comprising nucleotide sequences encoding a polypeptide of the disclosure or directly transferring the polypeptide to the cell. The cell can be an immune cell (e.g., a T lymphocyte or NK cell), a stem cell, a progenitor cell, etc. In some embodiments, the cell is a cell described herein.

In some embodiments, the genetic modification is carried out ex vivo. For example, a T lymphocyte, a stem cell, or an NK cell (or cell described herein) is obtained from an individual; and the cell obtained from the individual is genetically modified to express a polypeptide of the disclosure. In some cases, the genetically modified cell is activated ex vivo (i.e., TGF-β is contacted with the cells ex vivo). In other cases, the genetically modified cell is introduced into an individual (e.g., the individual from whom the cell was obtained); and the genetically modified cell is activated in vivo (i.e., by endogenously produced TGF-β).

In some embodiments, the methods further comprise the administration of additional therapeutic agents, such as bi-specific T cell engagers (BITE). Such therapeutic agents may be administered in peptide form to the patient or expressed in cells of the disclosure, such as those that that comprise the TGF-β CAR. The BITE may have antigen specificity for a cancer antigen/cancer molecule known in the art and/or described herein and may also have antigen specificity for a T cell molecule such as CD3.

In some embodiments, the methods relate to administration of the cells or peptides described herein for the treatment of a cancer or administration to a person with a cancer. In some embodiments the cancer is adrenal cancer, anal cancer, bile duct cancer, bladder cancer, bone cancer, brain/CNS tumors in children or adults, breast cancer, cervical cancer, colon/rectum cancer, endometrial cancer, esophagus cancer, ewing family of tumors, eye cancer, gallbladder cancer, gastrointestinal carcinoid tumors, gastrointestinal stromal tumor (GIST), gestation trophoblastic disease, hodgkin disease, kaposi sarcoma, kidney cancer, laryngeal and hypopharyngeal cancer, leukemia, acute lymphocytic leukemia, acute myeloid leukemia, chronic lymphocytic leukemia, chronic myeloid leukemia, chronic myelomonocytic leukemia, liver cancer, lung cancer, non-small cell lung cancer, small cell lung cancer, lung carcinoid tumor, lymphoma, malignant mesothelioma, multiple myeloma, myelodysplastic syndrome, nasal cavity and paranasal sinum cancer, nasopharyngeal cancer, neuroblastoma, non-hodgkin lymphoma, oral cavity or oropharyngeal cancer, osteosarcoa, ovarian cancer, pancreatic cancer, penile cancer, pituitary tumors, prostate cancer, retinoblastoma, rhabdomyosarcoma, salivary gland cancer, skin cancer, sarcoma, basal skin cancer, squamous cell skin cancer, melanoma, merkel cell skin cancer, small intestine cancer, stomach cancer, testicular cancer, thymus cancer, thyroid cancer, uterine sarcoma, vaginal cancer, vulvar cancer, waldenstrom macroglobulinemia, or wilms tumor.

Embodiments can be used to treat or ameliorate a number of immune-mediated, inflammatory, or autoimmune-inflammatory diseases, e.g., allergies, asthma, diabetes (e.g. type 1 diabetes), graft rejection, etc. Examples of such diseases or disorders also include, but are not limited to arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and systemic juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, guttate psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, proliferative nephritis, autoimmune polyglandular endocrine failure, balanitis including balanitis circumscripta plasmacellularis, balanoposthitis, erythema annulare centrifugum, erythema dyschromicum perstans, erythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, allergic reaction, eczema including allergic or atopic eczema, asteatotic eczema, dyshidrotic eczema, and vesicular palmoplantar eczema, asthma such as asthma bronchiale, bronchial asthma, and auto-immune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus, juvenile onset (Type I) diabetes mellitus, including pediatric insulin-dependent diabetes mellitus (IDDM), and adult onset diabetes mellitus (Type II diabetes) and autoimmune diabetes. Also contemplated are immune responses associated with acute and delayed hypersensitivity mediated by cytokines and T-lymphocytes, sarcoidosis, granulomatosis including lymphomatoid granulomatosis, Wegener's granulomatosis, agranulocytosis, vasculitides, including vasculitis, large-vessel vasculitis (including polymyalgia rheumatica and gianT cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), Addison's disease, autoimmune neutropenia, pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Behcet's disease/syndrome, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, thermal injury, preeclampsia, an immune complex disorder such as immune complex nephritis, antibody-mediated nephritis, polyneuropathies, chronic neuropathy such as IgM polyneuropathies or IgM-mediated neuropathy, autoimmune or immune-mediated thrombocytopenia such as idiopathic thrombocytopeniarpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), experimental autoimmune encephalomyelitis, myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, gianT cell hepatitis, chronic active hepatitis or autoimmune chronic active hepatitis, lymphoid interstitial pneumonitis (LIP), bronchiolitis obliterans (non-transplant) vs NSIP, Guillain-Barre syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia greata, alopecia totalis, CREST syndrome (calcinosis, Raynaud's phenomenon, esophageal dysmotility, sclerodactyly), and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, filariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis, endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, gianT cell polymyalgia, chronic hypersensitivity pneumonitis, keratoconjunctivitis sicca, epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders, asperniogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, non-malignant thymoma, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane allergic disease, neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, autoimmune polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism, neurological disease, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, graft versus host disease, contact hypersensitivity, asthmatic airway hyperreaction, and endometriosis.

V. Pharmaceutical Compositions

The present disclosure includes methods for modulating immune responses in a subject in need thereof. The disclosure includes cells that may be in the form of a pharmaceutical composition that can be used to induce or modify an immune response.

Administration of the compositions according to the current disclosure will typically be via any common route. This includes, but is not limited to parenteral, orthotopic, intradermal, subcutaneous, intramuscular, intraperitoneal, intranasal, or intravenous injection.

Typically, compositions of the invention are administered in a manner compatible with the dosage formulation, and in such amount as will be therapeutically effective and immune modifying. The quantity to be administered depends on the subject to be treated. Precise amounts of active ingredient required to be administered depend on the judgment of the practitioner.

The manner of application may be varied widely. Any of the conventional methods for administration of pharmaceutical compositions comprising cellular components are applicable. The dosage of the pharmaceutical composition will depend on the route of administration and will vary according to the size and health of the subject.

In many instances, it will be desirable to have multiple administrations of at most about or at least about 3, 4, 5, 6, 7, 8, 9, 10 or more. The administrations may range from 2-day to 12-week intervals, more usually from one to two week intervals. The course of the administrations may be followed by assays for alloreactive immune responses and T cell activity.

The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. The pharmaceutical compositions of the current disclosure are pharmaceutically acceptable compositions.

The compositions of the disclosure can be formulated for parenteral administration, e.g., formulated for injection via the intravenous, intramuscular, subcutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol. It also should be stable under the conditions of manufacture and storage and must be preserved against the contaminating action of microorganisms, such as bacteria and fungi.

Sterile injectable solutions are prepared by incorporating the active ingredients (i.e. cells of the disclosure) in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above.

An effective amount of a composition is determined based on the intended goal. The term "unit dose" or "dosage" refers to physically discrete units suitable for use in a subject, each unit containing a predetermined quantity of the composition calculated to produce the desired responses discussed herein in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions will be administered in a manner compatible with the dosage formulation and in such amount as is therapeutically or prophylactically effective. The formulations are easily administered in a variety of dosage forms, such as the type of injectable solutions described above.

VI. Sequences

Antigen binding domains of the disclosure include the following VH (variable heavy) and VL (variable light) regions:

```
scFv#1 VH:
                                         (SEQ ID NO: 1)
EVQLVESGGGLVQPGGSLRLSCAASGYAFTNYLIEWVRQAPGKGLEWVGV

INPGSGGSNYNEKFKGRATISADNSKNTLYLQMNSLRAEDTAVYYCARSG

GFYFDYWGQGTLVTVSSASTKGPS

scFv#1 VL:
                                         (SEQ ID NO: 2)
DIQMTQSPSSLSASVGDRVTITCRASQSVLYSSNQKNYLAWYQQKPGKAP

KLLIYWASTRESGVPSRFSGSGSGTDFTLTISSLQPEDFATYYCHQYLSS

DTFGQGTKVEIKRTVA

scFv#2 VH:
                                         (SEQ ID NO: 3)
QVQLVQSGAEVKKPGSSVKVSCKASGYTFSSNVISWVRQAPGQGLEWMGG

VIPIVDIANYAQRFKGRVTITADESTSTTYMELSSLRSEDTAVYYCALPR

AFVLDAMDYWGQGTLVTVSS
```

-continued

```
scFv#2 VL:
                                         (SEQ ID NO: 4)
ETVLTQSPGTLSLSPGERATLSCRASQSLGSSYLAWYQQKPGQAPRLLIY

GASSRAPGIPDRFSGSGSGTDFTLTISRLEPEDFAVYYCQQYADSPITFG

QGTRLEIK

scFv#3 VH:
                                         (SEQ ID NO: 19)
EVQLVESGGGVVQPGRSLRLSCAASGFTFSSYGMHWVRQAPGKELEWVAV

ISYDGSIKYYADSVKGRFTISRDNSKNTLYLQMNSLRAEDTAVYYCARTG

EYSGYDTDPQYSWGQGTTVTVSS

scFv#3 VL:
                                         (SEQ ID NO: 20)
EIVLTQSPSSLSASVGDRVTITCRSSQGIGDDLGWYQQKPGKAPILLIYG

TSTLQSGVPSRFSGSGSGTDFTLTINSLQPEDFATYYCLQDSNYPLTFGG

GTRLEIK
```

The corresponding CDRs of the VH and VL regions of scFv #1 are the following amino acid sequences: scFv #1 HCDR1: GYAFTNYLIE (SEQ ID NO:5); scFv #1 HCDR2: VINPGSGGSNYNEKFKG (SEQ ID NO:6); scFv #1 HCDR3: SGGFYFDY (SEQ ID NO:7); scFv #1 LCDR1: RASQSVLYSSNQKNYLA (SEQ ID NO:8); scFv #1 LCDR2: WASTRES (SEQ ID NO:9); scFv #1 LCDR3: HQYLSSDT (SEQ ID NO:10).

The corresponding CDRs of the VH and VL regions of scFv #2 are the following amino acid sequences: scFv #2 HCDR1: SNVIS (SEQ ID NO:11); scFv #2 HCDR2: GVIPIVDIANYAQRFKG (SEQ ID NO:12); scFv #2 HCDR3: PRAFVLDAMDY (SEQ ID NO: 13); scFv #2 LCDR1: RASQSLGSSYLA (SEQ ID NO:14); scFv #2 LCDR2: GASSRAP (SEQ ID NO:15); and scFv #2 LCDR3: QQYADSPIT (SEQ ID NO:16)

The corresponding CDRs of the VH and VL regions of scFv #3 are the following amino acid sequences: scFv #3 HCDR1: SYGMH (SEQ ID NO:21); scFv #3 HCDR2: VISYDGSIKYYADSVKG (SEQ ID NO:22); scFv #3 HCDR3: TGEYSGYDTDPQYS (SEQ ID NO: 23); scFv #3 LCDR1: RSSQGIGDDLG (SEQ ID NO:24); scFv #3 LCDR2: GTSTLQS (SEQ ID NO:25); and scFv #3 LCDR3: LQDSNYPLT (SEQ ID NO:26).

Detection peptides of the disclosure can include, for example, HA: YPYDVPDYA (SEQ ID NO:94); FLAG: DYKDDDDK (SEQ ID NO:17); and c-myc: EQKLISEEDL; SEQ ID NO: 95).

An exemplary signal peptide includes: METDTLLLWVLLLWVPGSTG (SEQ ID NO: 18). Other exemplary signal peptides include: MLLVTSLLLCELPHPAFLLIPDT (SEQ ID NO: 94) or MGTSLLCWMALCLLGADHADG (SEQ ID NO:95).

Exemplary peptide spacer hinge regions include: DKTHT (SEQ ID NO:27), CPPC (SEQ ID NO:28), CPEPKSCDTPPPCPR (SEQ ID NO:29), ELKTPLGDTTHT (SEQ ID NO: 30), KSCDKTHTCP (SEQ ID NO:31), KCCVDCP (SEQ ID NO:32), KYGPPCP (SEQ ID NO:33), EPKSCDKTHTCPPCP (SEQ ID NO:34; human IgG1 hinge), ERKCCVECPPCP (SEQ ID NO:35; human IgG2 hinge), ELKTPLGDTTHTCPRCP (SEQ ID NO: 36; human IgG3 hinge), SPNMVPHAHHAQ (SEQ ID NO:37); ESKYGPPCPPCP (SEQ ID NO:98), ESKYGPPCPSCP (SEQ ID NO:99) (human IgG4 hinge-based), EPKSCDKTYTCPPCP (SEQ ID NO:38), and TTTPAPRPPTPAPTIASQPLSLRPEACRPAAGGAVHTRGLDFACD (SEQ ID NO:39)

Exemplary peptide linkers include, for example, (GSGGS)n (SEQ ID NO:40); $(GGGS)_n$ (SEQ ID NO:41); GGSG (SEQ ID NO:42); GGSGG (SEQ ID NO:43); GSGSG (SEQ ID NO:44); GSGGG (SEQ ID NO:45); GGGSG (SEQ ID NO:46); and GSSSG (SEQ ID NO: 47).

Exemplary transmembrane domains include IYIWAPLAGTCGVLLLSLVITLYC (SEQ ID NO:48), CD8 beta derived: LGLLVAGVLVLLVSLGVAIHLCC (SEQ ID NO:49), CD4 derived: ALIVLGGVAGLLLFIGLGIFFCVRC (SEQ ID NO:50), CD3 zeta derived: LCYLLDGILFIYGVILTALFLRV (SEQ ID NO:51), CD28 derived: WVLVVVGGVLACYSLLVTVAFIIFWV (SEQ ID NO:52), CD134 (OX40) derived: VAAILGLGLVLGLLGPLAILLALYLL (SEQ ID NO:53), and CD7 derived: ALPAALAVISFLLGLGLGVACVLA (SEQ ID NO:54).

Exemplary co-stimulatory regions include:

(SEQ ID NO: 55)
KRGRKKLLYIFKQPFMRPVQTTQEEDGCSCRFPEEEEGGCEL, (SEQ ID NO: 56)
FWVRSKRSRLLHSDYMNMTPRRPGPTRKHYQPYAPPRDFAAYRS, (SEQ ID NO: 57)
TKKKYSSSVHDPNGEYMFMRAVNTAKKSRLTDVTL, (SEQ ID NO: 58)
RRDQRLPPDAHKPPGGGSFRTPIQEEQADAHSTLAKI, (SEQ ID NO: 59)
CCLRRHQGKQNELSDTAGREINLVDAHLKSEQTEASTRQNSQVLLSETGI
YDNDPDLCFRMQEGSEVYSNPCLEENKPGIVYASLNHSVIGPNSRLARNV
KEAPTEYASICVRS, (SEQ ID NO: 60)
HQRRKYRSNKGESPVEPAEPCRYSCPREEEGSTIPIQEDYRKPEPACSP, (SEQ ID NO: 61)
RRACRKRIRQKLHLCYPVQTSQPKLELVDSRPRRSSTQLRSGASVTEPVA
EERGLMSQPLMETCHSVGAAYLESLPLQDASPAGGPSSPRDLPEPRVSTE
HTNNKIEKIYIMKADTVIVGTVKAELPEGRGLAGPAEPELEEELEADHTP
HYPEQETEPPLGSCSDVMLSVEEEGKEDPLPTAASGK, (SEQ ID NO: 62)
HIWQLRSQCMWPRETQLLLEVPPSTEDARSCQFPEEERGERSAEEKGRLG
DLWV, and (SEQ ID NO: 63)
CVKRRKPRGDVVKVIVSVQRKRQEAEGEATVIEALQAPPDVTTVAVEETI
PSFTGRSPNH.

In some embodiments, the endodomain comprises an ITAM motif. An ITAM motif is $YX_1X_2(L/I)$, where $X_1$ and $X_2$ are independently any amino acid (SEQ ID NO:64). In some cases, an ITAM motif is repeated twice in an endodomain, where the first and second instances of the ITAM motif are separated from one another by 6 to 8 amino acids, e.g., $(YX_1X_2(L/I))\ (X_3)_n(YX_1X_2(L/I))$, where n is an integer from 6 to 8, and each of the 6-8 $X_3$ can be any amino acid (SEQ ID NO:65).

Exemplary endodomains include polypeptides from:

(SEQ ID NO: 66)
MGGLEPCSRLLLLPLLLAVSGLRPVQAQAQSDCSCCSTVSPGVLAGIVMG
DLVLTVLIALAVYFLGRLVPRGRGAAEAATRKORITETESPYOELOGORS
DVYSDLNTQRPYYK, (SEQ ID NO: 67)
MGGLEPCSRLLLLPLLLAVSGLRPVQAQAQSDCSCSTVSPGVLAGIVMGD
LVLTVLIALAVYFLGRLVPRGRGAAEATRKORITETESPYOELOGORSDV
YSDLNTQRPYYK;

(SEQ ID NO: 68)
MGGLEPCSRLLLLPLLLAVSDCSCSTVSPGVLAGIVMGDLVLTVLIALAV
YFLGRLVPRGRGAAEAATRKORITETESPYOELOGORSDVYSDLNTQRPY
YK;

(SEQ ID NO: 69)
MGGLEPCSRLLLLPLLLAVSDCSCSTVSPGVLAGIVMGDLVLTVLIALAV
YFLGRLVPRGRGAAEATRKORITETESPYOELOGORSDVYSDLNTQRPYY
K;

(SEQ ID NO: 70)
ESPYOELOGORSDVYSDLNTO;

(SEQ ID NO: 71)
MIPAVVLLLLLLVEQAAALGEPQLCYILDAILFLYGIVLTLLYCRLKIQV
RKAAITSYEKSDGVYTGLSTRNQETYETLKHEKPPQ;

(SEQ ID NO: 72)
DGVYTGLSTRNOETYETLKHE;

(SEQ ID NO: 73)
MEHSTFLSGLVLATLLSQVSPFKIPIEELEDRVFVNCNTSITWVEGTVGT
LLSDITRLDLGKRILDPRGIYRCNGTDIYKDKESTVQVHYRMCQSCVELD
PATVAGIIVTDVIATLLLALGVFCFAGHETGRLSGAADTOALLRNDOVYO
PLRDRDDAOYSHLGGNWARNK;

(SEQ ID NO: 74)
MEHSTFLSGLVLATLLSQVSPFKIPIEELEDRVFVNCNTSITWVEGTVGT
LLSDITRLDLGKRILDPRGIYRCNGTDIYKDKESTVOVHYRTADTOALLR
NDOVYOPLRDRDDAQYSHLGGNWARNK;

(SEQ ID NO: 75)
DOVYOPLRDRDDAOYSHLGGN;

(SEQ ID NO: 76)
MQSGTHWRVLGLCLLSVGVWGQDGNEEMGGITQTPYKVSISGTTVILTCP
QYPGSEILWQHNDKNIGGDEDDKNIGSDEDHLSLKEFSELEQSGYYVCYP
RGSKPEDANFYLYLRARVCENCMEMDVMSVATIVIVDICITGGLLLLVYY
WSKNRKAKAKPVTRGAGAGGRQRGQNKERPPPVPNPDYEPIRKGQRDLYS
GLNQRRI;

(SEQ ID NO: 77)
NPDYEPIRKGQRDLYSGLNQR;

(SEQ ID NO: 78)
MEQGKGLAVLILAIILLQGTLAQSIKGNHLVKVYDYQEDGSVLLTCDAEA
KNITWFKDGKMIGFLTEDKKKWNLGSNAKDPRGMYQCKGSQNKSKPLQVY

-continued

YRIVICQNCIELNAATISGFLFAEIVSIFVLAVGVYFIAGODGVROSRAS

DKOTLLPNDOLYOPLKDREDDQYSHLQGNQLRRN;

(SEQ ID NO: 79)
DOLYOPLKDREDDOYSHLOGN;

(SEQ ID NO: 80)
MKWKALFTAAILQAQLPITEAQSFGLLDPKLCYLLDGILFIYGVILTALF

LRVKFSRSADAPAYQQGQNQLYNELNLGRREEYDVLDKRRGRDPEMGGKP

RRKNPQEGLYNELKDKMAEAYSEIGMKGERRRGKGHDGLYOGLSTATKDT

YDALHMQALPPR;

(SEQ ID NO: 81)
MKWKALFTAAILQAQLPITEAQSFGLLDPKLCYLLDGILFIYGVILTALF

LRVKFSRSADAPAYQQGQNQLYNELNLGRREEYDVLDKRRGRDPEMGGKP

QRRKNPQEGLYNELOKDKMAEAYSEIGMKGERRRGKGHDGLYOGLSTATK

DTYDALHMQALPPR;

(SEQ ID NO: 82)
RVKFSRSADAPAYOQGONOLYNELNLGRREEYDVLDKRRGRDPEMGGKPR

RKNPOEGLYNELOKDKMAEAYSEIGMKGERRRGKGHDGLYOGLSTATKDT

YDALHMQALPPR;

(SEQ ID NO: 83)
NOLYNELNLGRREEYDVLDKR;

(SEQ ID NO: 84)
EGLYNELQKDKMAEAYSEIGMK;

(SEQ ID NO: 85)
DGLYOGLSTATKDTYDALHMO;

(SEQ ID NO: 86)
MPGGPGVLQALPATIFLLFLLSAVYLGPGCQALWMHKVPASLMVSLGEDA

HFQCPHNSSNNANVTWWRVLHGNYTWPPEFLGPGEDPNGTLIIQNVNKSH

GGIYVCRVQEGNESYQQSCGTYLRVRQPPPRPFLDMGEGTKNRIITAEGI

ILLFCAVVPGTLLLFRKRWONEKLGLDAGDEYEDENLYEGLNLDDCSMYE

DISRGLOGTYQDVGSLNIGDVQLEKP;

(SEQ ID NO: 87)
MPGGPGVLQALPATIFLLFLLSAVYLGPGCQALWMHKVPASLMVSLGEDA

HFQCPHNSSNNANVTWWRVLHGNYTWPPEFLGPGEDPNEPPPRPFLDMGE

GTKNRIITAEGIILLFCAVVPGTLLLFRKRWQNEKLGLDAGDEYEDENLY

EGLNLDDCSMYEDISRGLQGTYQDVGSLNIGDVQLEKP;

(SEQ ID NO: 88)
ENLYEGLNLDDCSMYEDISRG;

(SEQ ID NO: 89)
RPRRSPAQDGKVYINMPGRG;

(SEQ ID NO: 90)
RPRRSPAQDGKVYINMPGRG;

(SEQ ID NO: 91)
FWVLVVVGGVLACYSLLVTVAFIIFWVRSKRSRLLHSDYMNMTPRRPGPT

RKHYQPYAPPRDFAAYRS;

(SEQ ID NO: 92)
FWVLVVVGGVLACYSLLVTVAFIIFWVRSKRSRLLHSDYMNMTPRRPGPT

RKHYQPYAPPRDFAAYRS;
and

-continued (SEQ ID NO: 93)
MPDPAAHLPFFYGSISRAEAEEHLKLAGMADGLFLLRQCLRSLGGYVLSL

VHDVRFHHFPIERQLNGTYAIAGGKAHCGPAELCEFYSRDPDGLPCNLRK

PCNRPSGLEPQPGVFDCLRDANIVRDYVRQTWKLEGEALEQAIISQAPQV

EKLIATTAHERMPWYHSSLTREEAERKLYSGAQTDGKFLLRPRKEQGTYA

LSLIYGKTVYHYLISQDKAGKYCIPEGTKFDTLWQLVEYLKLKADGLIYC

LKEACPNSSASNASGAAAPTLPAHPSTLTHPQRRIDTLNSDGYTPEPARI

TSPDKPRPMPMDTSVYESPYSDPEELKDKKLFLKRDNLLIADIELGCGNF

GSVRQGVYRMRKKQIDVAIKVLKQGTEKADTEEMMREAQIMHQLDNPYIV

RLIGVCQAEALMLVMEMAGGGPLHKFLVGKREEIPVSNVAELLHQVSMGM

KYLEEKNFVHRDLAARNVLLVNRHYAKISDFGLSKALGADDSYYTARSAG

KWPLKWYAPECINFRKFSSRSDVWSYGVTMWEALSYGQKPYKKMKGPEVM

AFIEQGKRMECPPECPPELYALMSDCWIYKWEDRPDFLTVEQRMRACYYS

LASKVEGPPGSTQKAEAACA
or portions thereof.

or portions thereof.

VII. Examples

The following examples are included to demonstrate embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

This disclosure describes single-chain variable fragments (scFvs) that neutralize human and mouse TGF-β, as well as chimeric antigen receptors (CARs) that are responsive to human and mouse TGF-β. The level of TGF-β conservation across mammals suggests that the scFvs and CARs described can be used to bind most mammalian TGF-β. Two scFvs are constructed from anti-TGF-β antibodies by connecting the heavy-chain variable domain (VH) to the light-chain variable domain (VL) with a (G4S)3 linker such that the final orientation is N-terminus-VH-$(G_4S)_3$-VL-C-terminus. These scFvs can be produced by transfecting eukaryotic cells with DNA sequences encoding the scFv amino acid sequences indicated in the table below:

| Single Chain Variable Fragment | Amino Acid Sequence (Single Letter Abbreviations) |
|---|---|
| scFv #1 | METDTLLLWVLLLWVPGSTGAGGSDYKDDDDKGGSEVQLVESGGGL VQPGGSLRLSCAASGYAFTNYLIEWVRQAPGKGLEWVGVINPGSGGSN YNEKFKGRATISADNSKNTLYLQMNSLRAEDTAVYYCARSGGFYFDY WGQGTLVTVSSASTKGPSGGGGSGGGGSGGGGSDIQMTQSPSSLSASV GDRVTITCRASQSVLYSSNQKNYLAWYQQKPGKAPKLLIYWASTRESG VPSRFSGSGSGTDFTLTISSLQPEDFATYYCHQYLSSDTFGQGTKVEIKR TVA (SEQ ID NO: 96) |
| scFv #2 | METDTLLLWVLLLWVPGSTGAGGSDYKDDDDKGGSQVQLVQSGAEV KKPGSSVKVSCKASGYTFSSNVISWVRQAPGQGLEWMGGVIPIVDIAN YAQRFKGRVTITADESTSTTYMELSSLRSEDTAVYYCALPRAFVLDAM DYWGQGTLVTVSSGGGGSGGGGSGGGGSETVLTQSPGTLSLSPGERAT LSCRASQSLGSSYLAWYQQKPGQAPRLLIYGASSRAPGIPDRFSGSGSG TDFTLTISRLEPEDFAVYYCQQYADSPITFGQGTRLEIK (SEQ ID NO: 97) |

Figure 7:
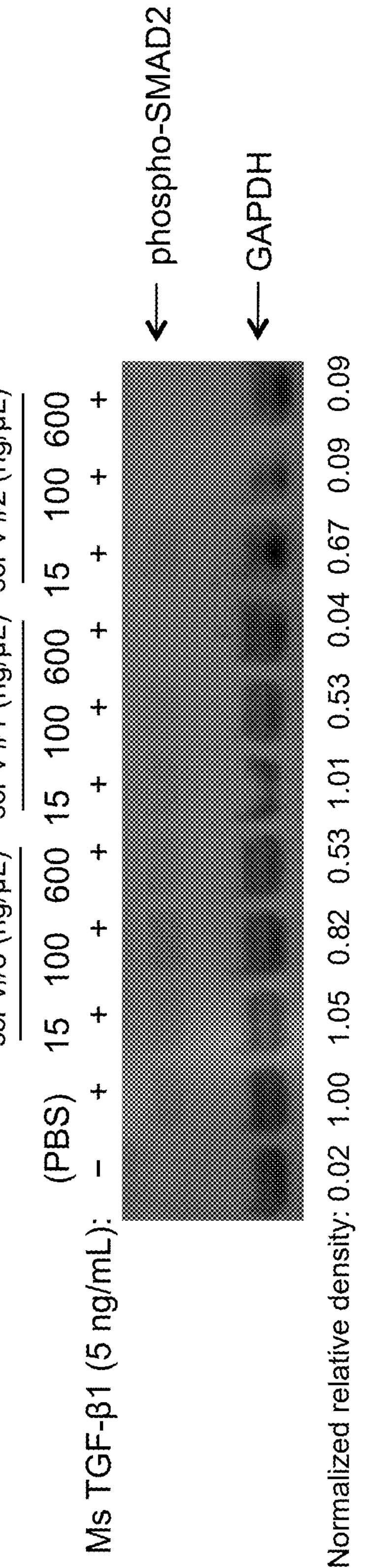
FIG. 7 shows the inhibition of murine TGF-β/SMAD signaling. Indicated amounts of scFv and mouse TGF-β1 were applied to NIH3T3 fibroblasts for 30 min. Cells were lysed and probed for SMAD2 phosphorylation.

Each scFv can be tagged with the leader (i.e. signal) peptide from the murine kappa light chain so that scFvs are secreted and can be directly collected from the media in which the producer cells are cultured. The scFvs can also be tagged at the N-terminal end (after the leader peptide but before the VH sequence) with markers such as the DYKDDDDK (SEQ ID NO:17) epitope, HA tag, or cMyc tag flanked by GGS linkers. Each scFv can be directly administered to neutralize human or mouse TGF-β. scFv #1 and #2 are superior to scFv #3 (FIGS. 1 and 7). Furthermore, each scFv can be used to construct a CAR responsive to TGF-β. CARs are fusion proteins composed of an extracellular antigen-binding domain, an extracellular spacer, a transmembrane domain, costimulatory signaling regions (the number of which varies depending on the specific CAR design), and a CD3-zeta signaling domain/endodomain. TGF-β CARs can be constructed using the scFvs described above as the extracellular antigen-binding domain. Immune cells, including T cells and natural killer (NK) cells, can be engineered to express TGF-β CARs by a variety of methods, including viral transduction, DNA nucleofection, and RNA nucleofection. TGF-β binding to the TGF-β CAR can activate human T cells, thereby redirecting TGF-β signaling from an immunosuppressive response to an immunostimulatory response. The TGF-β CAR can also be used as an accessory receptor to counter immunosuppression and boost T-cell-mediated responses in all adoptive T-cell therapies, whether based on tumor infiltrating lymphocytes, T-cell receptor engineering, or other CARs.

Figure 9:
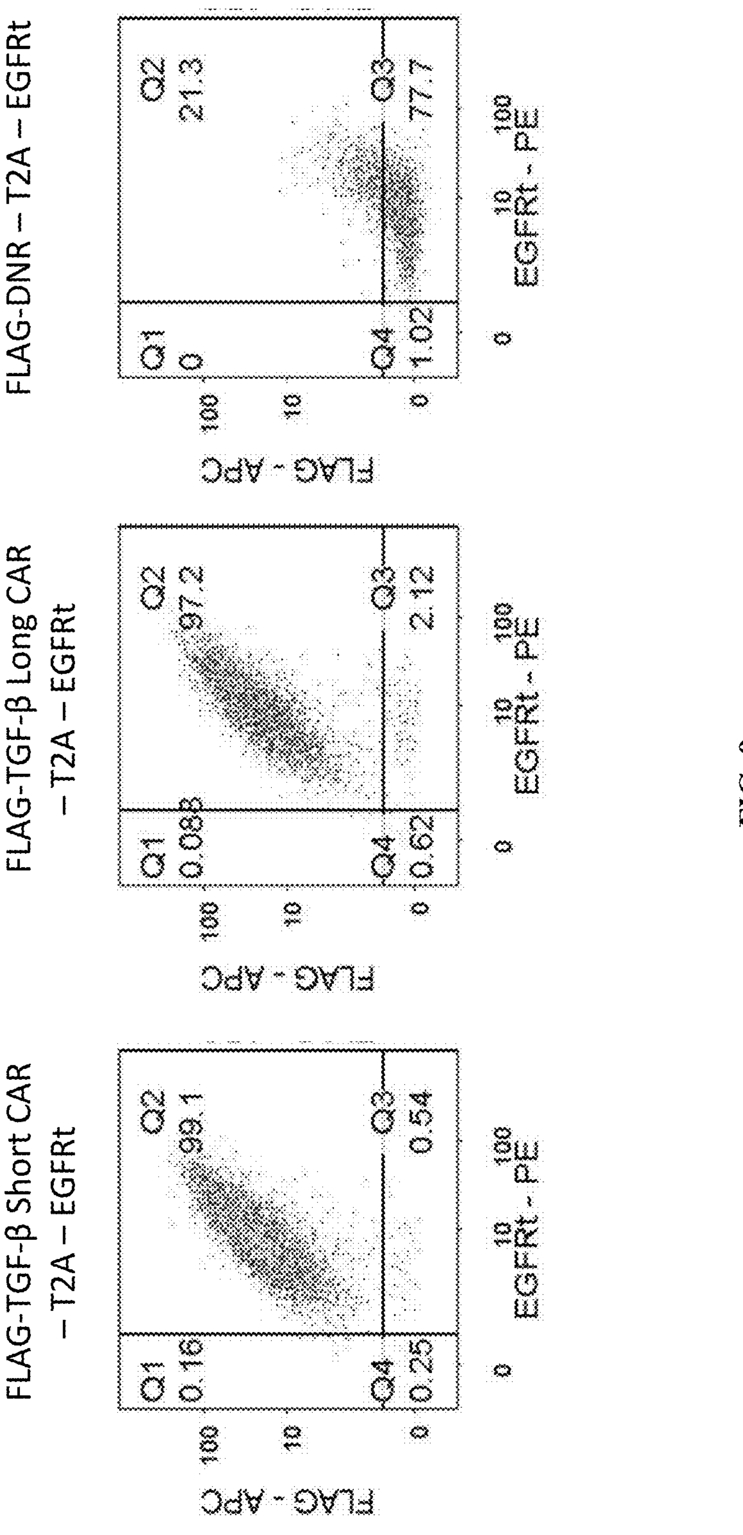
FIG. 9. TGF-β CAR presents to the cell surface more efficiently than the dominant-negative TGF-β receptor.

As shown in FIG. 2, TGF-β CARs are efficiently expressed on the surface of primary human T cells. A TGF-β CAR was created using scFv #2. Surface staining and flow cytometry show that TGF-β CARs are presented on the surface of primary human CD4+ and CD8+ T cells. The receptor's extracellular domain contains an N-terminal FLAG epitope. EGFRt is a truncated epidermal growth factor receptor that is an indicator of cell transduction. It was further found that TGF-β CAR presents to the cell surface more efficiently than the dominant-negative TGF-β receptor (FIG. 9). A dominant-negative TGF-β receptor (DNR) comprising a truncated TGF-β receptor chain II that is missing the intracellular signaling domain has been reported to inhibit TGF-β signaling and improve T-cell effector function. However, the DNR is not efficiently expressed on the cell surface whereas the TGF-β CAR is. The data shown in FIG. 9 are from the transduction of primary human CD4+ T cells with lentiviruses encoding either FLAG-tagged TGF-β CARs or FLAG-tagged DNR. Each receptor is tagged via a T2A cleavage peptide to truncated epidermal growth factor receptor (EGFRt), such that transduced cells can be identified by EGFRt staining whereas receptor surface expression can be identified by FLAG staining. The results of FIG. 9 indicate that TGF-β CARs are much more efficiently expressed on T cell surfaces than the DNR.

Figure 3:
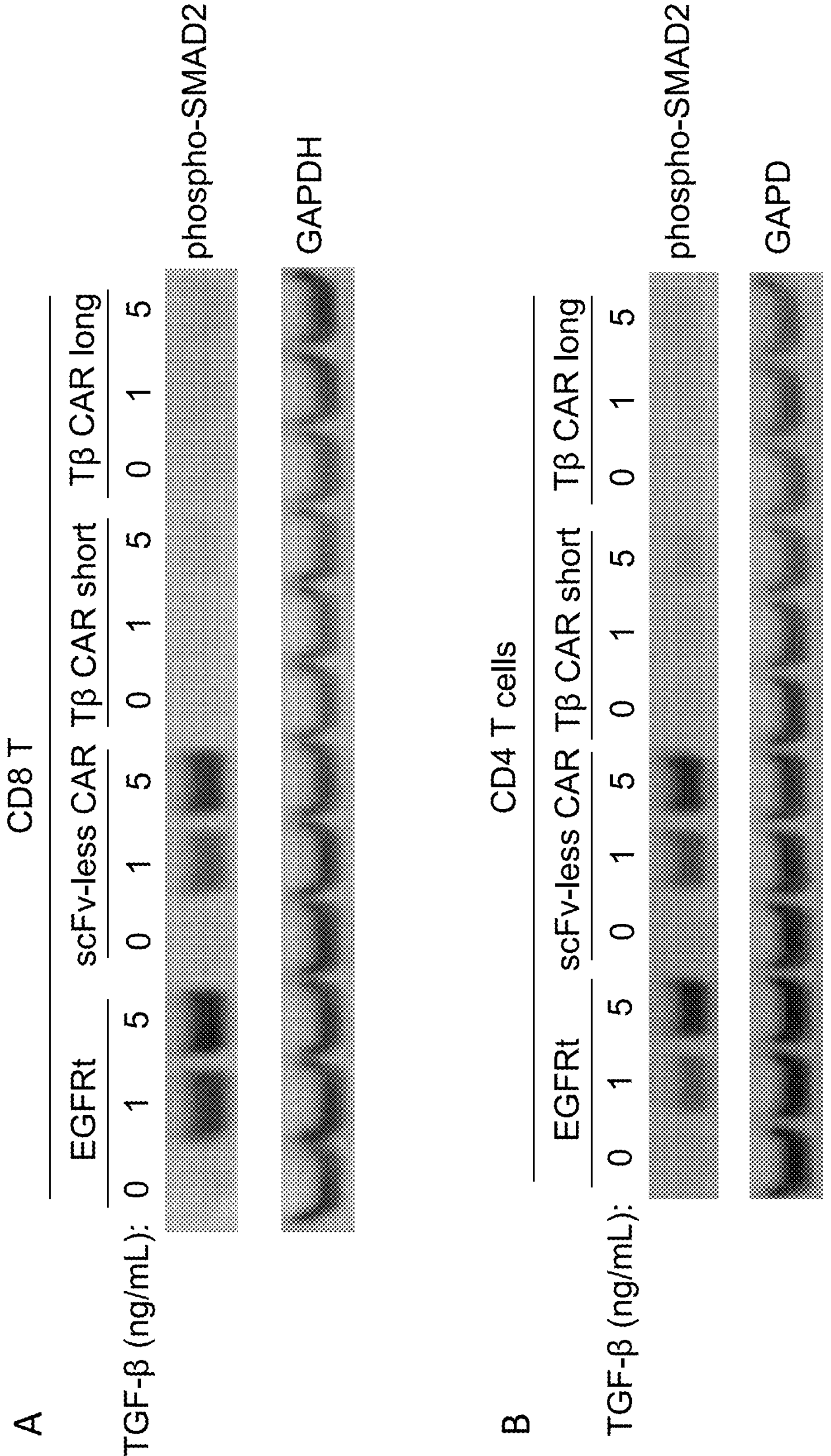
FIG. 3A-B demonstrates that TGF-β CARs block endogenous TGF-β signaling in CD8+ (A) and CD4+ (B) T cells. TGF-β CAR expression in T cells blocks TGF-β signaling via the SMAD pathway. T cells expressing the indicated receptor were incubated with TGF-β for 30 min and probed for phospho-SMAD2 via western blot. scFv-less refers to a CAR that lacks any ligand (antigen)-binding scFv domain, EGFRt refers to a truncated epidermal growth factor receptor that is irrelevant to the other components here.
Figure 6:
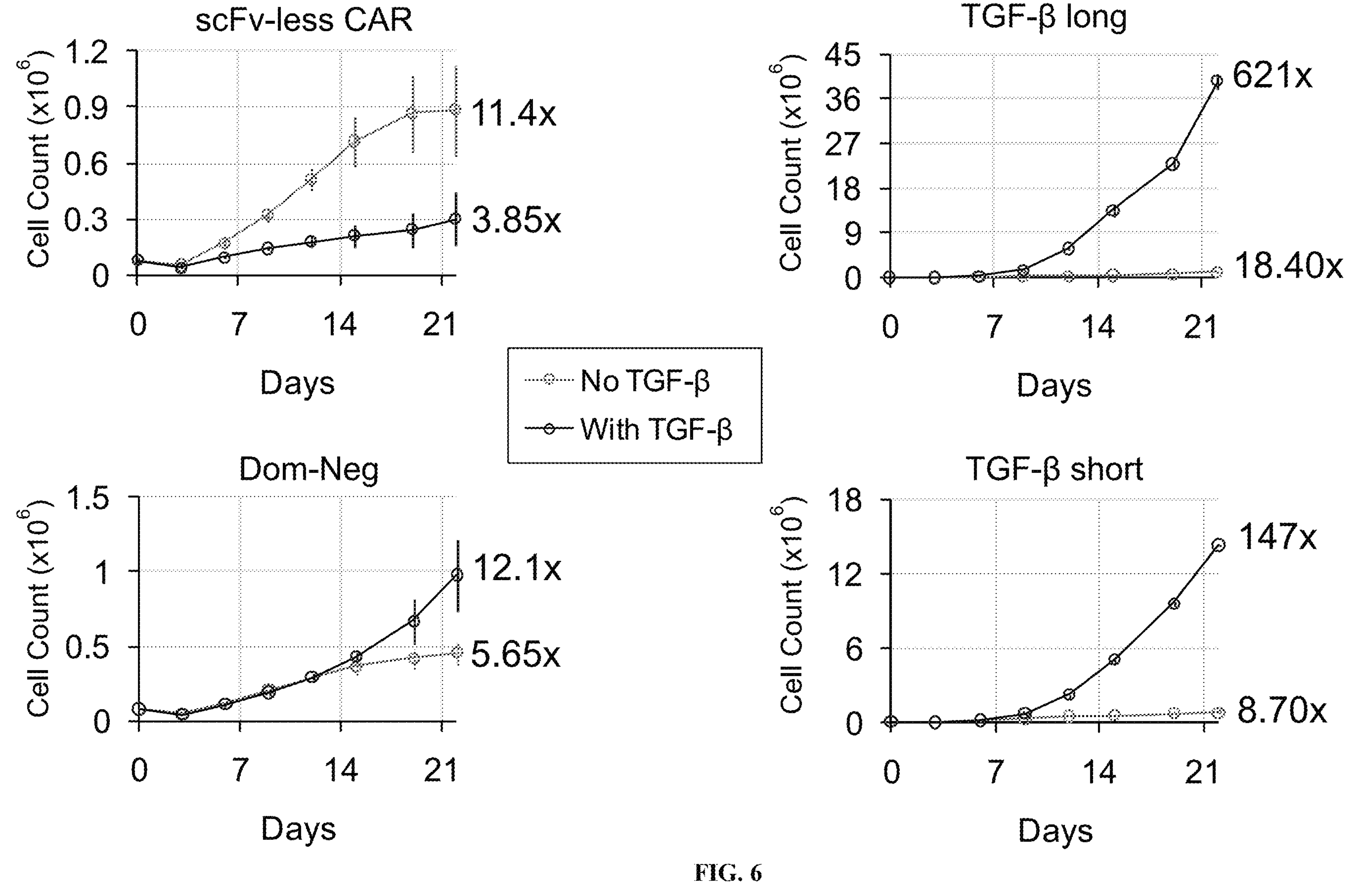
FIG. 6 demonstrates that TGF-β CAR-T cells proliferate in response to TGF-β.

FIG. 3 shows that TGF-β CARs block endogenous TGF-β signaling. TGF-β CAR expression in primary human T cells blocks TGF-β signaling via the SMAD pathway. T cells expressing the indicated receptor were incubated with TGF-β at the indicated concentration for 30 min and probed for phospho-SMAD2 via Western Blot. EGFRt refers to T cells expressing a truncated epidermal growth factor receptor and serves as a "no CAR" control; scFv-less refers to T cells expressing a CAR that lacks any ligand-binding scFv domain but is otherwise identical to the TGF-β CAR long. "Long" and "short" labels behind TGF-β CARs refer to the length of their extracellular peptide spacers. As shown in FIG. 6, TGF-β CAR-T cells proliferate in response to TGF-β. T cells expressing TGF-β CARs convert TGF-β from a growth-inhibitory cytokine to a growth-promoting cytokine.

Figure 4:
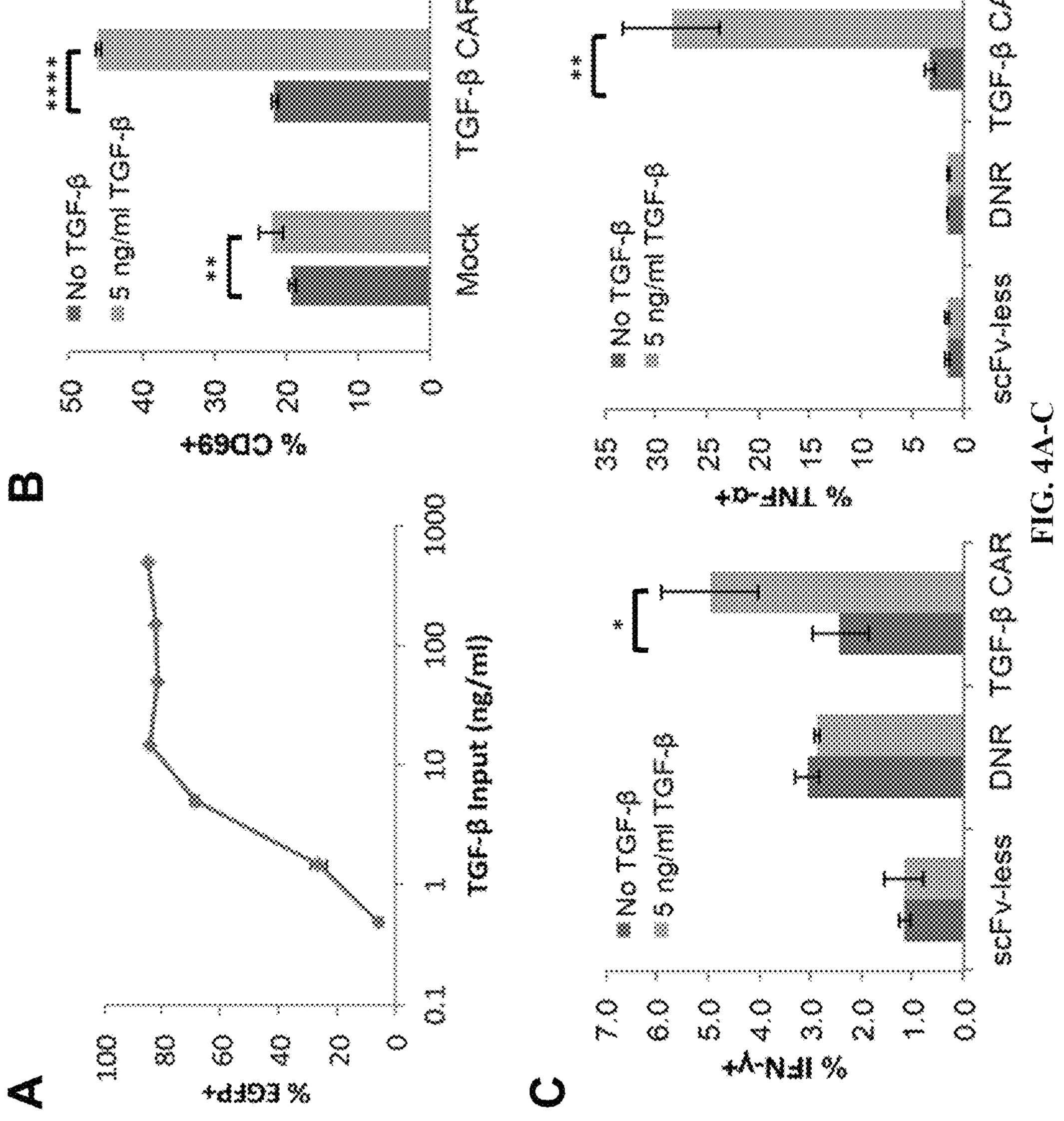
FIG. 4A-C. (A) Jurkat cells stably expressing the TGF-β CAR and an NFAT reporter (EGFP expressed from an NFAT-inducible promoter) show increased activation in response to increasing TGF-β concentrations. (B,C) Primary human CD4+ T cells stably expressing the TGF-β CAR upregulate (B) CD69 expression and (C) Th1 cytokine production in response to TGF-β stimulation. CD69 upregulation was monitored by surface staining after a one-day incubation with or without TGF-β. Cytokine production was detected by applying the protein transport inhibitor Brefeldin A and performing intracellular staining after a one-day incubation with or without TGF-β. "Mock" denotes T cells transduced with an irrelevant construct. "scFv-less" denotes T cells expressing a CAR that is identical to the TGF-β CAR except it lacks the scFv domain and thus cannot bind to TGF-β. "DNR" is the dominant-negative TGF-β receptor, which is a truncated TGF-β receptor chain 2 that lacks the cytoplasmic signaling domain. Values shown are the means of triplicates with error bars indicating ±1 standard deviation (s.t.d.). *$p<0.05$; $p<0.005$, *$p<0.0005$, *****$p\leq 0.0005$.

It was also found that TGF-β CARs activate T cells and trigger cytokine production (FIG. 4). As shown in FIG. 4, TGF-β CAR-T cells upregulate expression of the CD69 activation marker and produce the immunostimulatory cytokines IFN-γ and TNF-α in response to TGF-β exposure. CD69 upregulation was monitored by surfaced staining after a 24-hour incubation with or without TGF-β. Cytokine production was detected by applying the protein transport inhibitor Brefeldin A and performing intracellular staining after a 24-hour incubation with or without TGF-β. "scFv-less" refers to a CAR lacking any ligand-binding scFv domain.

Figure 5:
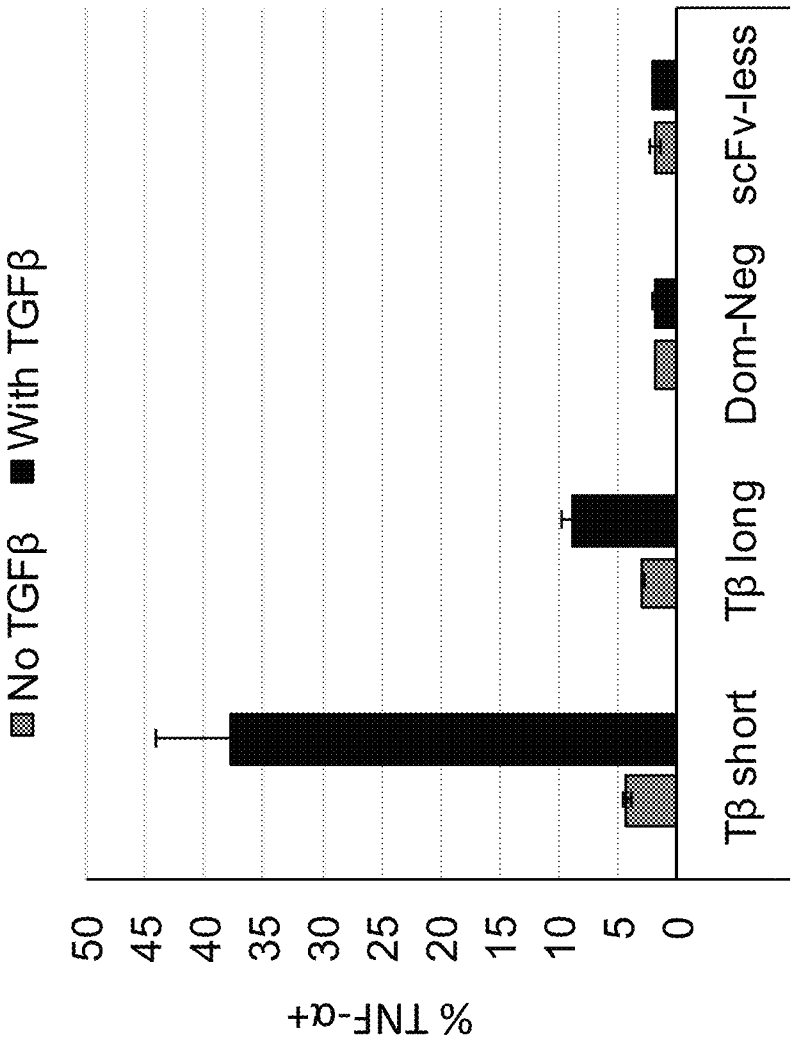
FIG. 5 shows that dominant-negative TGF-β receptor is unable to trigger cytokine production. While the dominant-negative TGF-β receptor has been reported to also inhibit TGF-β signaling, it does not trigger immunostimulatory actions such as TNF-α production. Tβ short and Tβ long are two different TGF-β CARs, Dom-Neg refers to the dominant-negative TGF-β receptor, and scFv-less refers to a CAR that lacks any ligand-binding scFv domain. Tβ short refers to the TGF-β CAR polypeptide with a peptide spacer consisting of the IgG4 hinge region only. Tβ long refers to the TGF-β CAR polypeptide with a peptide spacer that contains the IgG4 hinge and $CH_2CH_3$ regions.

Unlike TGF-β CARs, the dominant-negative TGF-β receptor cannot trigger cytokine production. While the dominant-negative TGF-β receptor has been reported to also inhibit TGF-β signaling, it does not trigger immunostimulatory actions such as TNF-α production (FIG. 5). "Tβ short" and "Tβ long" are two different TGF-β CARS, "Dom-Neg" refers to the dominant-negative TGF-β receptor, and "scFv-less" refers to a CAR that lacks any ligand-binding scFv domain.

Figure 10:
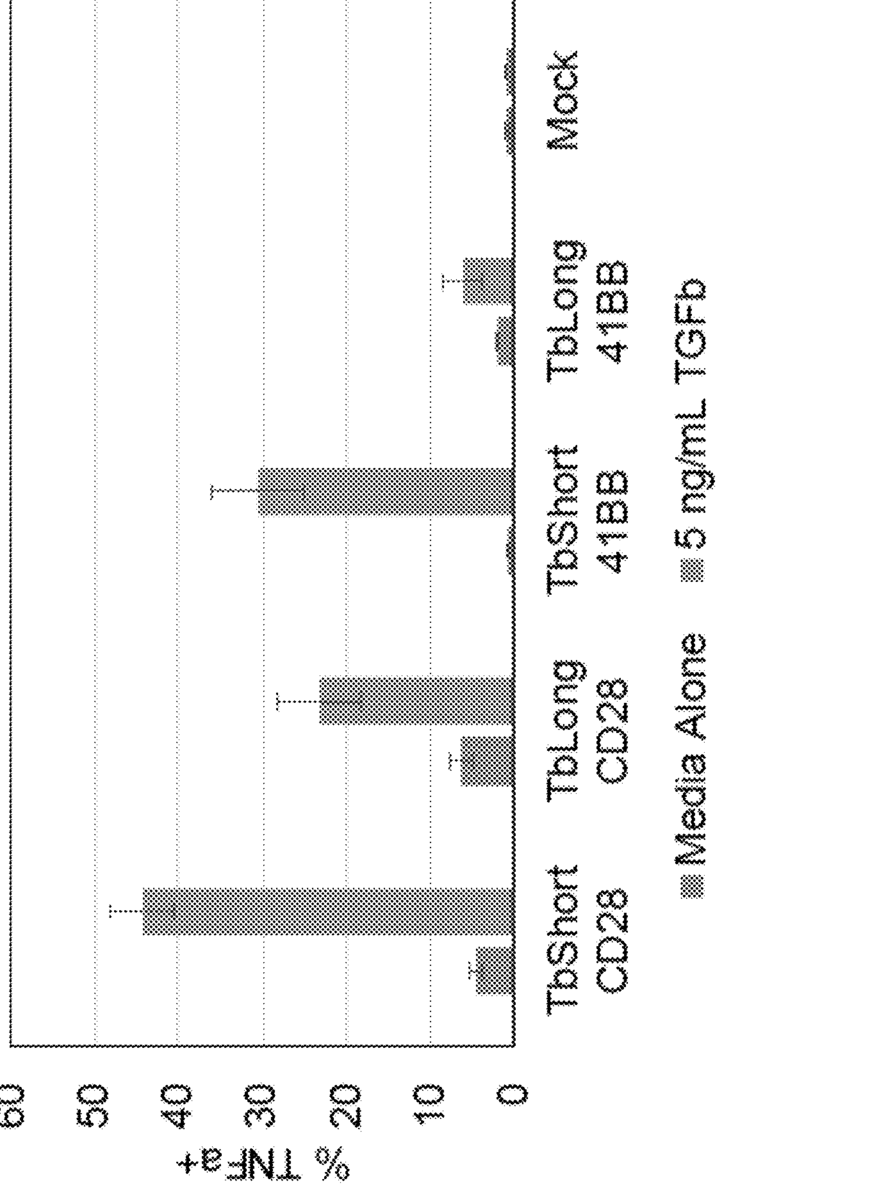
FIG. 10. TGF-β CAR function can be tuned by co-stimulatory domain choice.
Figure 11:
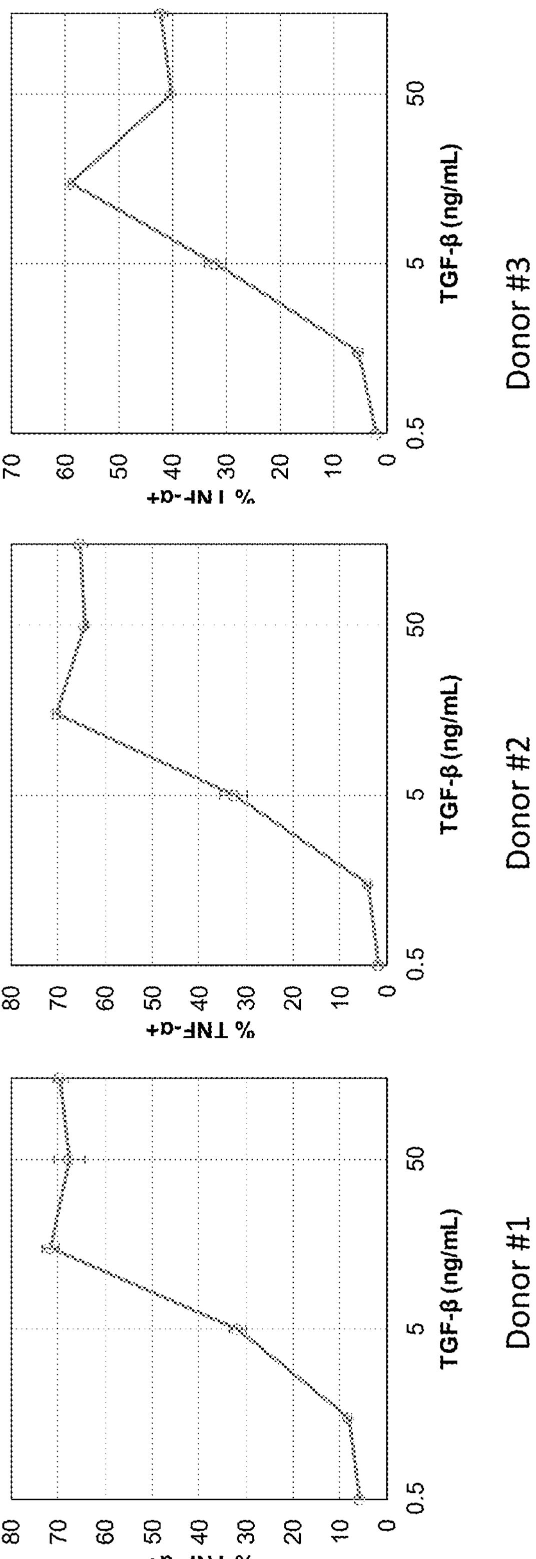
FIG. 11. TGF-β consistently triggers TNF-α production in a dose-dependent manner across cells from different donors.

It was further found that TGF-β CAR function can be tuned by co-stimulatory domain choice. As shown in FIG. 10, switching between CD28 and 4-1BB co-stimulatory domains alters the cytokine production levels in response to TGF-β. Furthermore, it was found that TGF-β consistently triggers TNF-α production in a dose-dependent manner across cells with the TGF-β CAR from different donors, suggesting that the performance of the CAR is robust enough to be relied upon for clinical applications (FIG. 11).

Figure 12:
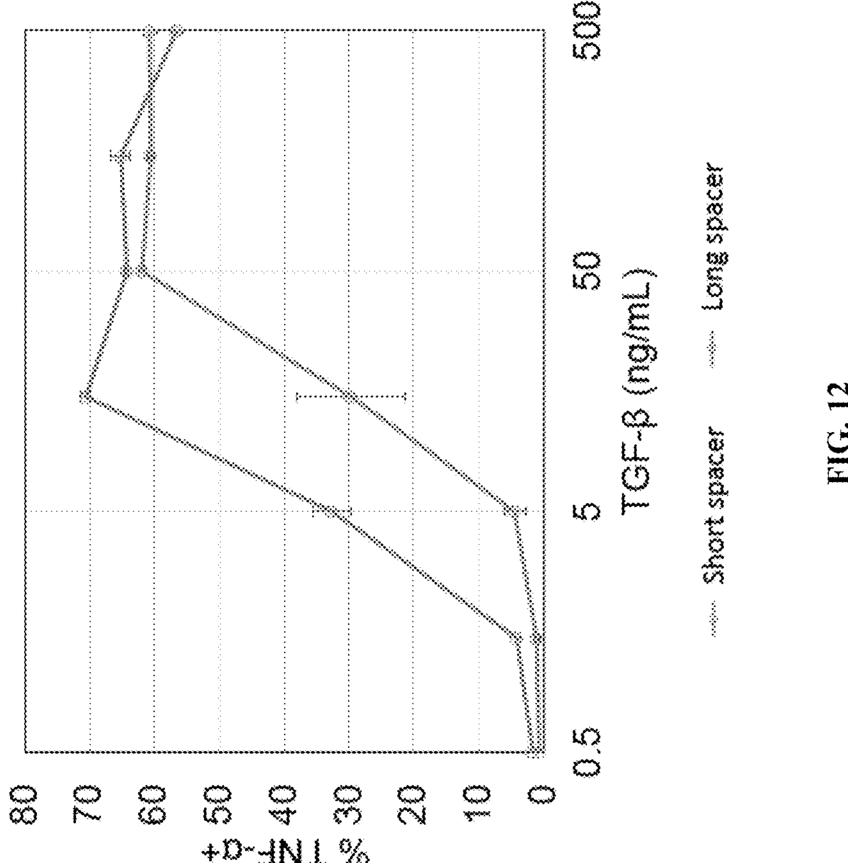
FIG. 12. TGF-β CAR's peptide spacer length modulates the triggering threshold.

It was further found that the TGF-β CAR spacer length modulates the triggering threshold. Increasing the extracellular spacer length increases the TGF-β threshold of CAR triggering (FIG. 12). This suggests that one can customize the CAR responsiveness to the needs of the application by altering the coupling between the ligand binding domain and the intracellular signaling domains. "Short spacer" comprises the hinge portion of human IgG4; "long spacer" comprises IgG4 hinge-CH2-CH3.

Figure 13:
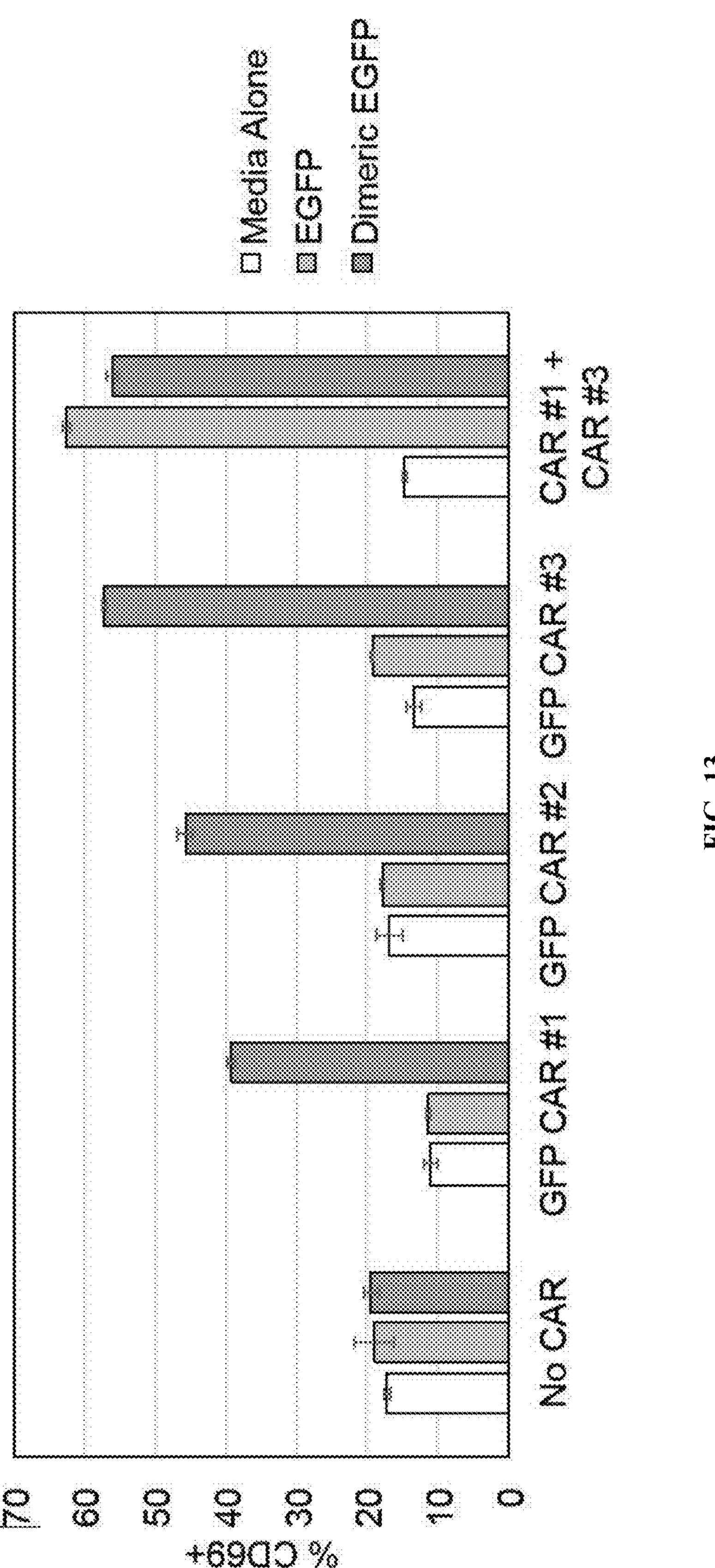
FIG. 13. CAR signaling requires ligand-mediated CAR dimerization, but there is no requirement that the ligand or the CAR itself pre-exists as a dimer. CD69 surface staining was performed on Jurkat cell lines that carry the indicated CAR(s). GFP CAR #1 and GFP CAR #3 both exist predominantly as homodimers, and the two CARs bind to different epitopes on EGFP and can concurrently bind a monomeric EGFP molecule. GFP CAR #1 and GFP CAR #2 bind to the same epitope on EGFP, but CAR #2 exists as a monomer rather than a homodimer.
Figure 14:
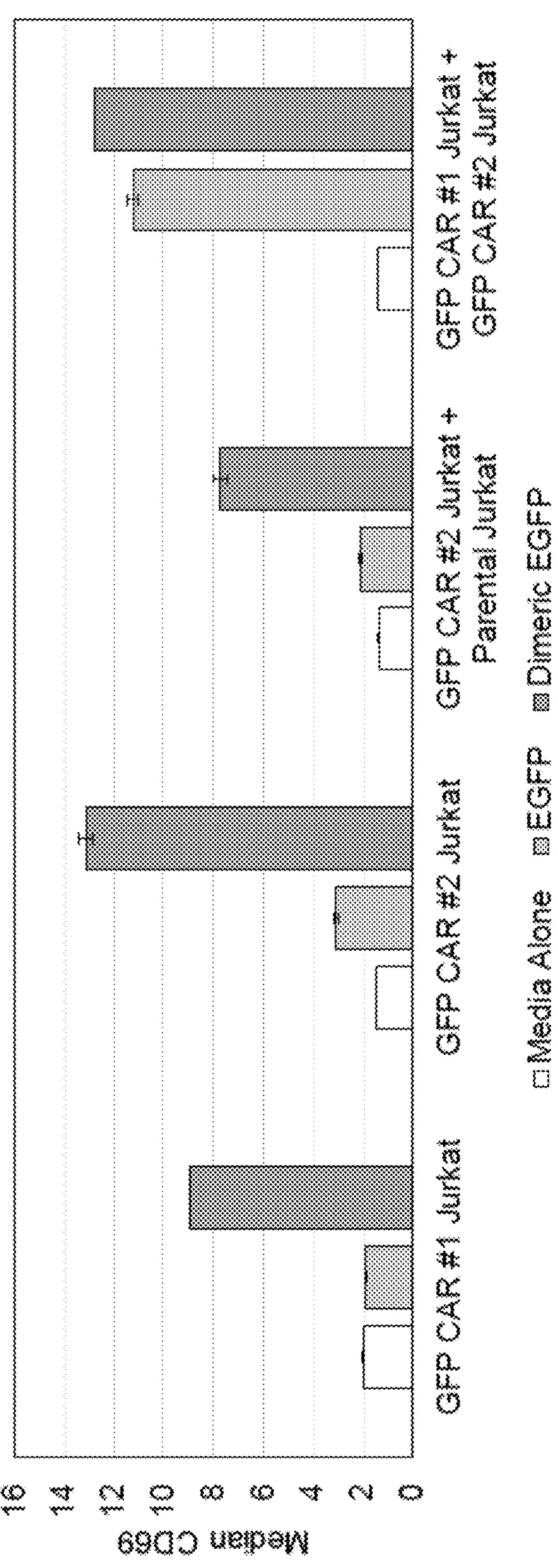
FIG. 14. Soluble, dimeric antigen molecules can trigger signaling by ligating receptors on different cells.

Next, it was discovered that soluble ligand-mediated CAR dimerization triggers CAR signaling. Shown in FIG. 13 are Jurkat cell lines carrying the indicated CAR(s). GFP CAR #1 and GFP CAR #3 both exist predominantly in homodimer form, and the two CARs bind to different epitopes on EGFP and can concurrently bind an individual EGFP molecule. GFP CAR #1 and GFP CAR #2 bind to the same epitope on EGFP, but CAR #2 exists as a monomer rather than a homodimer. Results indicate that CAR signaling can be facilitated by ligand-mediated CAR dimerization, but there is no requirement that the ligand or the CAR itself pre-exist as a dimer (FIG. 13). One possible mechanism by which soluble ligands can trigger CAR signaling is by ligating receptors on two different cells, thereby forming an immunological synapse. This mechanism is consistent with the observation that Jurkat cells expressing a single type of GFP CAR can be activated by dimeric but not monomeric EGFP. It is also consistent with the observation that a mixture of two Jurkat cell lines, each expressing a different GFP CAR, can be activated by both dimeric and monomeric EGFP. In this instance, monomeric EGFP can also trigger cell-cell ligation since the CARs on the two Jurkat cell lines bind to two different epitopes on the same EGFP molecule (FIG. 14).

Figure 15:
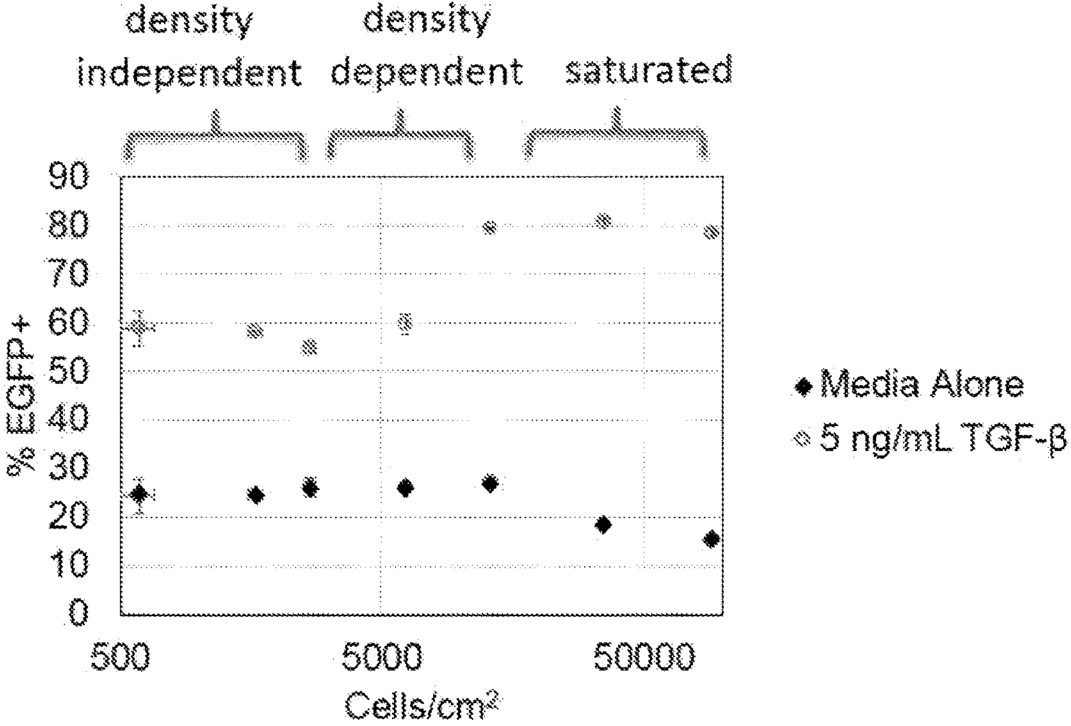
FIG. 15. TGF-β CAR can be triggered in both cell-cell contact-dependent and -independent manners.
Figure 16:
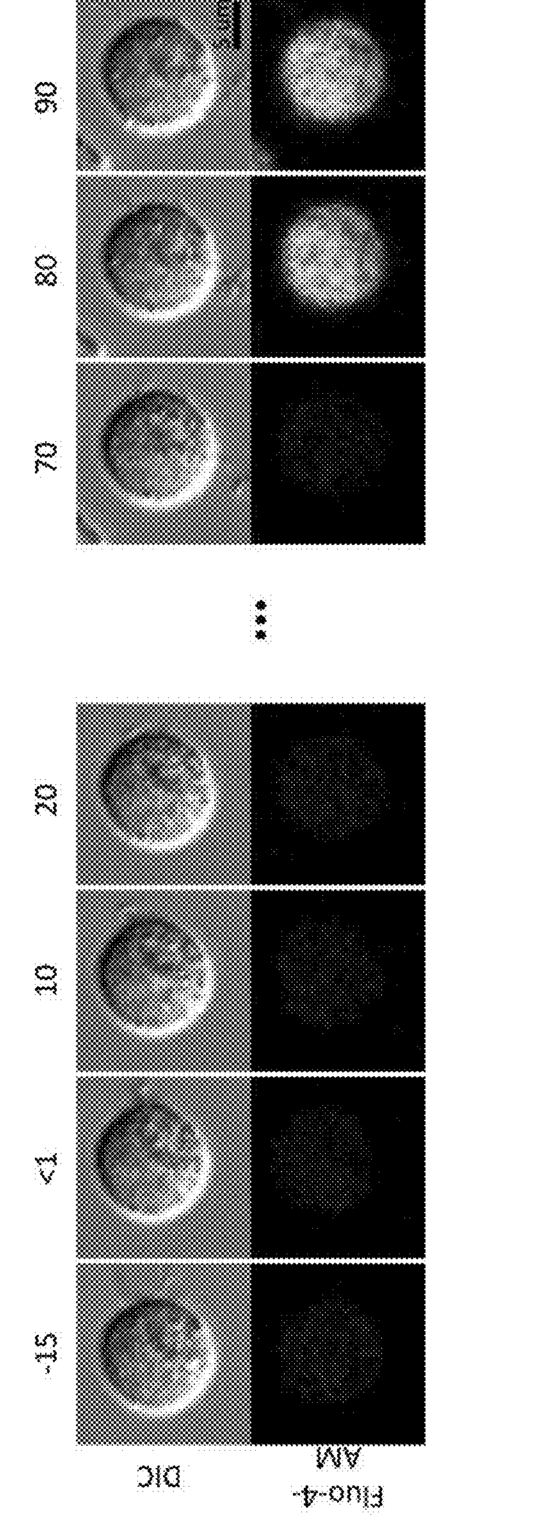
FIG. 16. TGF-β CAR-T cells can be activated in the absence of cell-cell contact.

It was found that TGF-β CAR can be triggered in both cell-cell contact-dependent and -independent manners. Although cell-cell contact is one possible mechanism by which soluble ligands such as EGFP and TGF-β can trigger CAR signaling, CAR-T cell activation can also be triggered by soluble ligand in the absence of cell-cell contact. In FIG. 15, Jurkat cells stably expressing the TGF-β CAR and an EGFP reporter expressed from an NFAT promoter are seeded at various cell densities and incubated with or without 5 ng/ml TGF-β. Even at very low cell densities where cells exist predominantly as single-cell isolates, clear EGFP signal is observed in the presence of TGF-β. Furthermore, for a 10-fold range in cell density (from 500 to 5000 cells/cm^2), there is no increase in EGFP output with cell density (FIG. 15). These results indicate that soluble TGF-β can trigger T-cell activation independently of cell-cell contact. However, EGFP output increases significantly beyond a threshold cell density, confirming the contribution of cell-cell contact at higher cell density levels. To further test this, primary human CD4+ T cells expressing TGF-β CAR were labeled with the calcium indicator Fluo-4-AM and imaged by fluorescence microscopy. Fluo-4-AM signals observed after TGF-β addition in the absence of cell-cell contact confirms that TGF-β CAR-T cells can be activated by soluble ligands without cell-cell ligation (FIG. 16).

The TGF-β CAR addresses the need for immune cells to counteract TGF-β's role as a driver of immunosuppression in the tumor microenvironment. While CAR-T-cell therapy has yielded remarkable clinical outcomes against B-cell malignancies, its efficacy against solid tumors has been significantly more limited. Solid tumors are known to generate a highly immunosuppressive microenvironment through the overproduction of TGF-β and other cytokines, ultimately resulting in the inactivation of T cells. The TGF-β CAR endows T cells with the ability to not only counter immunosuppression by reducing signaling through the endogenous TGF-β pathway, but also specifically trigger T-cell activation in the presence of TGF-β. T-cell activation spurs the immune cell to produce immunostimulatory cytokines and proliferate, thus turning TGF-β from an immunosuppressive signal to an activating stimulus that invigorates the anti-tumor immune response.

Example 2: Engineering Multi-Functional Regulatory T-Cell Therapy for Autoimmune Diseases This example describes methods that can be used to engineer chimeric antigen receptor (CAR)-expressing regulatory T cells (Tregs) that can be activated by tumor growth factor beta (TGF-β) to selectively expand ex vivo, maintain robust suppressive function in vivo, and secrete anti-interleukin 6 receptor alpha (IL-6Rα) single-chain variable fragments (scFvs) to effectively reduce inflammation in a mouse model of rheumatoid arthritis (RA). It is contemplated that other autoimmune diseases, such as those known in the art and/or described herein, can also be treated by methods described in this example and disclosure.

Adoptive T-cell therapy using conventional T cells (Tconvs) expressing chimeric antigen receptors (CARs) have demonstrated remarkable clinical efficacy against refractory cancers, particularly B-cell malignancies. However, the application of CAR-T-cell therapy to the treatment of autoimmune diseases is still in its infancy.

Tregs suppress Tconv function through multiple mechanisms, one of which is the secretion of TGF-β, a potent immunosuppressive cytokine that inhibits both effector T-cell and natural killer cell functions. The inventors have developed a TGF-β CAR that specifically activates Tconvs in the presence of TGF-β (FIG. 4), and have confirmed that TGF-β CAR-T cells respond to TGF-β in both soluble and immobilized forms. Human CD4+ and CD8+ Tconvs expressing the TGF-β CAR trigger robust NFAT signaling and produce Th2 cytokines in the presence of TGF-β, despite the fact that TGF-β is normally a highly immunosuppressive agent (FIG. 4).

It is contemplated that the TGF-β CAR would be uniquely suited for Treg therapy for the following reasons: 1) TGF-β is known to promote Treg differentiation, thus TGF-β-mediated expansion of CAR-expressing T cells present a method to selectively expand Tregs while preventing the outgrowth of contaminating Tconvs. We have observed that TGF-β drives robust proliferation of TGF-β CAR-expressing Tconvs, but only in the presence of irradiated feeder cells. In the absence of feeder cells, the proliferation of TGF-β CAR-Tconvs is specifically inhibited by the presence of TGF-β, and the inhibition is significantly stronger against TGF-β CAR-Tconvs compared to unmodified Tconvs or Tconvs expressing non-TGFβ CARs. The inventor's experimental results suggest that TGF-β, which exists as a natural homodimer, can cause conjugation between two T cells that both express the TGF-β CAR. This cell-cell conjugation may result in fratricidal toxicity among Tconvs. This toxicity can be more than compensated by the proliferative response that results from CAR signaling, but only with the support of irradiated feeder cells. Unlike Tconvs, Tregs do not exhibit granzyme-mediated cytotoxicity and they are not suppressed by endogenous TGF-β signaling. Therefore, it is contemplated that—in the absence of feeder-cell support-TGF-β CAR-expressing Tregs can be selectively expanded over contaminating Tconvs in a TGF-β-driven ex vivo expansion protocol, thereby addressing one of the major obstacles in the production of therapeutic Tregs. 2) Activated Tregs naturally produce TGF-β, thus providing a mechanism for self-sustaining activation of TGF-β CAR-Tregs in vitro and in vivo. It has been shown that antigen-specific Tregs are more effective than polyclonal Tregs in immunosuppression. On the other hand, it has also been shown that once activated, Tregs can exert suppressor function in an antigen-nonspecific manner. Furthermore, pre-activated, polyclonal Tregs have been demonstrated to inhibit collagen-induced arthritis in mice. Taken together, these results suggest that antigen-specific Tregs may be more effective because they are more likely to be activated than non-antigen-specific Tregs, and that specificity toward the target cell-though likely advantageous—is not essential for therapeutic function. Naturally antigen-specific Tregs are difficult to isolate and expand to large enough quantities for therapeutic applications. Although the introduction of transgenic T-cell receptors (TCRs) provide an appealing alternative, each disease would require its own specific TCR and the availability of a suitable antigen target, the latter of which has been recognized as a major bottleneck in the development of T-cell therapies. Since TGF-β production is a natural output of Tregs regardless of TCR specificity, the TGF-β CAR presents a generalizable strategy to enable self-sustaining Treg activation, which could support Treg-mediated suppression against a wide variety of disease targets without the need for disease-specific receptors.

This example provides novel methodologies and specific Treg products for cell-based immunotherapy against autoimmune diseases, with RA as the disease model for initial studies. The overall objective is to establish a generalizable approach to the generation of therapeutic Tregs with sustained therapeutic function, and to demonstrate the utility of engineered Tregs in a collagen-induced arthritis model in mice.

A. Develop a TGF-β-Mediated Ex Vivo Expansion Protocol for Robust Treg Propagation Primary human Tregs can be isolated from healthy donor blood samples using a RosetteSep CD4+ T-Cell Enrichment Kit followed by magnetic bead-based enrichment of CD127− and CD25+ cells. Isolated cells can be activated with CD3/CD28 Dynabeads and cultured in complete media (RPMI+10% heat-inactivated fetal bovine serum) supplemented with 300 U/ml IL-2 for 2 days prior to lentiviral transduction. Lentiviral vectors encoding the TGF-β CAR tagged (via a T2A cleavage peptide) with a truncated epidermal growth factor receptor (EGFRt) have already been constructed and validated by transduction into primary human Tconvs. CAR-expressing cells can be isolated by magnetic bead-based sorting for EGFRt+ cells. This sorting scheme avoids the need for direct antibody binding to the CAR and reduces the likelihood for unproductive T-cell activation. Sorted CAR-Tregs can be expanded in 96-well plates under a variety of culture conditions: (a) 300 U/ml IL-2 only, (b) TGF-β only at a gradient of concentrations (1-20 ng/ml), (c) a gradient of IL-2 (50-300 U/ml) plus TGF-β (1-20 ng/ml), and (d) a gradient of IL-2 and TGF-β concentrations plus irradiated feeder cells (TM-LCLs) at a 1:7 T-cell:TM-LCL ratio. Viable cell counts can be quantified by flow cytometry through a 3-week period. Furthermore, Foxp3 expression levels can be quantified by intracellular staining throughout the cell-preparation process, beginning with freshly isolated CD4+/CD25+/CD127− cells. A "scFv-less" CAR that is identical to the TGF-β CAR except it lacks the TGF-β-binding scFv domain has been constructed and can be included as a negative control.

Through the studies described in this example, one may determine the following: (1) whether TGF-β CAR expression confers Tregs with the ability to proliferate specifically in response to TGF-β addition and (2) identify the optimal combination of IL-2, TGF-β, and/or feeder cells for ex vivo Treg expansion with high efficiency (defined by large fold-expansion) and high purity (defined by minimal presence of contaminating Tconvs). The inventors have developed multiple TGF-β CARs with differing structural properties, and have observed distinct signaling thresholds of these CARs in response to TGF-β. Two different TGF-β CARs, one with a short (12-amino acid) extracellular spacer and another with a long (229-amino acid) extracellular spacer can be evaluated to determine the optimal construct for Treg applications.

B. Optimize the Suppressor Function of TGF-β CAR-Tregs In Vitro and in Vivo

The suppressor functions of Tregs that stably express the TGF-β CAR can be further investigated. Tregs will be isolated, transduced, and sorted as described above. Both the long-spacer and short-spacer TGF-β CARs can be evaluated. As a negative control, a fraction of the CD4+ T cells (prior to enrichment for CD127−/CD25+ phenotype) can be transduced and sorted to provide a TGF-β CAR-Tconv comparison against the engineered Tregs. As a second negative control, Tregs transduced with the scFv-less CAR described above can be included in the study. Sorted CAR-Tregs can be expanded in complete media supplemented with 300 U/ml IL-2, as this IL-2 concentration has been reported to support Treg survival and proliferation ex vivo and is an intermediate concentration among those reported in published studies. The expansion procedure can be updated to the condition determined to support optimal Treg expansion. Tconvs will be expanded in complete media supplemented with 50 U/ml IL-2 and 1 ng/ml IL-15.

The suppressor function of the TGF-β CAR-Tregs can be evaluated in co-cultures with target Tconvs. Target Tconvs will be CD4+ T cells lentivirally transduced to express the CD19 CAR. To assay Treg function, TGF-β CAR-Tregs can be co-incubated with both CFSE-labeled CD19 CAR-Tconvs and CD19+ Raji lymphoma cells in the presence or absence of soluble TGF-β. Proliferation of the CD19 CAR-Tconvs can be evaluated by CFSE dilution as well as viable cell counting via flow cytometry. CFSE-based proliferation assay can be performed instead of the more widely used 3H-thymidine incorporation assay in order to clearly distinguish Treg vs. Tconv proliferation in this co-culture setting. CFSE-labeled cells can be accurately quantified by flow cytometry starting from early time points, while CFSE dilution peaks will reveal cell-division dynamics over a 7-day period. As negative controls, TGF-β CAR-Tconvs or scFv-less CAR-Tregs can replace TGF-β CAR-Tregs in the co-incubation samples. It is expected that the scFv-less CAR-Tregs will show some suppressive function, but that TGF-β CAR-Tregs will show enhanced suppression due to TGF-β production and subsequent autocrine Treg activation through the TGF-β CAR. Furthermore, it is anticipated that the addition of exogenous TGF-β will further strengthen the TGF-β CAR-Tregs' suppressor function, resulting in minimal CD19 CAR-Tconv expansion despite the presence of CD19+ target cells.

Figure 8:
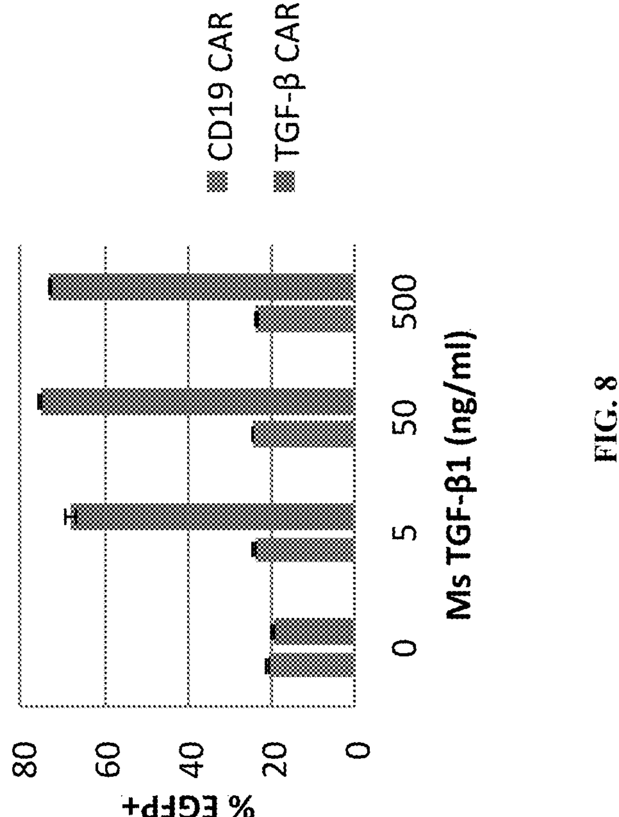
FIG. 8. Jurkat cells stably expressing the TGF-β CAR and an NFAT reporter (EGFP expressed from an NFAT-inducible promoter) show increased activation in response to increasing input of murine TGF-β1, indicating that the TGF-β CAR engineered to recognize human TGF-β also cross-reacts with murine TGF-β.

Upon verification of the TGF-β CAR-Tregs' suppressor function in vitro, the engineered Tregs' ability to execute suppressor function in vivo can be evaluated. For animal studies, murine CD4+/CD25+ Tregs will be isolated from the lymph nodes and spleens of DBA/1 mice by magnetic bead-based cell sorting. Sorted cells can be activated by murine CD3/CD28 Dynabeads and transduced, expanded, and sorted for TGF-β CAR expression as previously described for human Tregs. Although the TGF-β CAR is constructed with an scFv that targets human TGF-β, inventors have confirmed that this receptor cross-reacts with murine TGF-β with high efficiency (FIG. 8). To trigger collagen-induced arthritis (CIA), DBA/1 mice can be injected at the base of the tail with a 100-μl emulsion containing complete Freund adjuvant mixed at 1:1 ratio with 2 mg/ml chicken type II collagen dissolved in PBS with 0.1 M acetic acid. One million Tregs can be administered via tail-vein injection either one day before CIA immunization or two weeks after CIA immunization in order to evaluate the performance of Tregs at different stages of disease progression. TGF-β CAR-Tregs can be compared against scFv-less CAR-Tregs and a "no-Treg" control (i.e., no Treg administration after CIA immunization) for their ability to prevent or ameliorate arthritis. Mice can be assessed for clinical arthritis in the paws based on a 4-point scale as previously described by Kelchtermans, H. et al. (*Arthritis Res Ther* 7, R402-415 (2005)). Ten animals can be included for each test condition (40 animals total). The n=10 sample size will provide 92% power to detect a difference of 1.5 standard deviations in arthritis scoring in a two-sided t-test with $\alpha$=0.05. Based on available literature, it is anticipated that the scFv-less CAR-Tregs will achieve noticeable suppression of arthritic symptoms in the CIA model. However, it is anticipated that addition of the TGF-β CAR will result in enhanced Treg functionality, leading to more effective inhibition of CIA. It remains to be see whether the long-spacer or the short-spacer CAR will exhibit superior in vivo functionality in the CIA model.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All references, cited literature articles, patent publications, and sequences associated with any recited GenBank accession numbers are specifically incorporated herein by reference in their entirety for all purposes.

REFERENCES

The following references, to the extent that they provide exemplary procedural or other details supplementary to those set forth herein, are specifically incorporated herein by reference.

US20110008364;

U.S. Pat. No. 7,151,169;

Yingling et al, Nat Rev Drug Discov 2004;

U.S. Pat. No. 8,012,482;

US20060135517;

US2004026871;

US20070142376;

Gorelik and Flavell, Nat Med 2001;

Bollard et al, Blood 2002;

Zhang et al, Cancer Res 2005;

Foster et al, J Immunother 2008;

Zhang et al, Gene Ther 2012;

Quatromoni et al, J Transl Med 2012;

Bendle et al, J Immunol 2013

Brentjens, R. J. et al. CD19-targeted T cells rapidly induce molecular remissions in adults with chemotherapy-refractory acute lymphoblastic leukemia. *Sci Transl Med* 5, 177ra138 (2013).

Kalos, M. et al. T cells with chimeric antigen receptors have potent antitumor effects and can establish memory in patients with advanced leukemia. *Sci Transl Med* 3, 95ra73 (2011).

Kochenderfer, J. N. et al. B-cell depletion and remissions of malignancy along with cytokine-associated toxicity in a clinical trial of anti-CD19 chimeric-antigen-receptor-transduced T cells. *Blood* 119, 2709-2720 (2012).

Porter, D. L., Levine, B. L., Kalos, M., Bagg, A. & June, C. H. Chimeric antigen receptor-modified T cells in chronic lymphoid leukemia. *N Engl J Med* 365, 725-733 (2011).

Davila, M. L. et al. Efficacy and toxicity management of 19-28z CAR T cell therapy in B cell acute lymphoblastic leukemia. *Sci Transl Med* 6, 224ra225 (2014).

Ellebrecht, C. T. et al. Reengineering chimeric antigen receptor T cells for targeted therapy of autoimmune disease. *Science* 353, 179-184 (2016).

Wright, G. P., Ehrenstein, M. R. & Stauss, H. J. Regulatory T-cell adoptive immunotherapy: potential for treatment of autoimmunity. *Expert Rev Clin Immunol* 7, 213-225 (2011).

Wright, G. P. et al. Adoptive therapy with redirected primary regulatory T cells results in antigen-specific suppression of arthritis. *Proc Natl Acad Sci USA* 106, 19078-19083 (2009).

Kelchtermans, H. et al. Activated CD4+CD25+ regulatory T cells inhibit osteoclastogenesis and collagen-induced arthritis. *Ann Rheum Dis* 68, 744-750 (2009).

Morgan, M. E. et al. Effective treatment of collagen-induced arthritis by adoptive transfer of CD25+ regulatory T cells. *Arthritis Rheum* 52, 2212-2221 (2005). Blat, D., Zigmond, E., Alteber, Z., Waks, T. & Eshhar, Z. Suppression of murine colitis and its associated cancer by carcinoembryonic antigen-specific regulatory T cells. *Mol Ther* 22, 1018-1028 (2014).

Tang, Q. & Bluestone, J. A. Regulatory T-cell therapy in transplantation: moving to the clinic. *Cold Spring Harb Perspect Med* 3 (2013).

Nakamura, K. et al. TGF-beta 1 plays an important role in the mechanism of CD4+CD25+ regulatory T cell activity in both humans and mice. *J Immunol* 172, 834-842 (2004).

Thornton, A. M. & Shevach, E. M. Suppressor effector function of CD4+CD25+ immunoregulatory T cells is antigen nonspecific. *J Immunol* 164, 183-190 (2000).

Brusko, T. M. et al. Human antigen-specific regulatory T cells generated by T cell receptor gene transfer. *PLOS One* 5, e11726 (2010).

Rosenberg, S. A. Finding suitable targets is the major obstacle to cancer gene therapy. *Cancer Gene Ther* 21, 45-47 (2014).

Myasoedova, E., Crowson, C. S., Kremers, H. M., Therneau, T. M. & Gabriel, S. E. Is the incidence of rheumatoid arthritis rising?: results from Olmsted County, Minnesota, 1955-2007. *Arthritis Rheum* 62, 1576-1582 (2010).

Widdifield, J. et al. The epidemiology of rheumatoid arthritis in Ontario, Canada. *Arthritis Rheumatol* 66, 786-793 (2014).

Lee, D. W. et al. Current concepts in the diagnosis and management of cytokine release syndrome. *Blood* 124, 188-195 (2014).

Brudno, J. N. & Kochenderfer, J. N. Toxicities of chimeric antigen receptor T cells: recognition and management. *Blood* 127, 3321-3330 (2016).

Brunstein, C. G. et al. Umbilical cord blood-derived T regulatory cells to prevent GVHD: kinetics, toxicity profile, and clinical effect. *Blood* 127, 1044-1051 (2016).

Kelchtermans, H. et al. Defective CD4+CD25+ regulatory T cell functioning in collagen-induced arthritis: an important factor in pathogenesis, counter-regulated by endogenous IFN-gamma. *Arthritis Res Ther* 7, R402-415 (2005).

Wu, Y. et al. FOXP3 controls regulatory T cell function through cooperation with NFAT. *Cell* 126, 375-387 (2006).

The invention claimed is:

1. A polypeptide comprising a bi-specific chimeric antigen receptor (CAR), wherein the CAR comprises a signal peptide, an anti-TGF-β region comprising a variable heavy (VH) and variable light (VL) region, an IL13Rα2 binding region, a peptide spacer, a transmembrane domain, and an endodomain; wherein the anti-TGF-β region comprises:

i) a VH region comprising SEQ ID NO:5 (HCDR1), SEQ ID NO:6 (HCDR2); and SEQ ID NO: 7 (HCDR3) and a VL region comprising SEQ ID NO:8 (LCDR1), SEQ ID NO:9 (LCDR2); and SEQ ID NO:10 (LCDR3);

ii) a VH region comprising SEQ ID NO:11 (HCDR1), SEQ ID NO:12 (HCDR2); and SEQ ID NO: 13 (HCDR3) and a VL region comprising SEQ ID NO:14 (LCDR1), SEQ ID NO:15 (LCDR2); and SEQ ID NO:16 (LCDR3); or iii) a VH region comprising SEQ ID NO:21 (HCDR1), SEQ ID NO:22 (HCDR2); and SEQ ID NO:23 (HCDR3) and a VL region comprising SEQ ID NO:24 (LCDR1), SEQ ID NO:25 (LCDR2); and SEQ ID NO:26 (LCDR3).

2. The polypeptide of claim 1, wherein the polypeptide further comprises a co-stimulatory region between the transmembrane domain and endodomain.

3. The polypeptide of claim 1, wherein the transmembrane domain comprises a transmembrane domain of CD28.

4. The polypeptide of claim 1, wherein the endodomain is a CD3-zeta signaling domain.

5. The polypeptide of claim 1, wherein the peptide spacer comprises less than 50 amino acids.

6. The polypeptide of claim 1, wherein the peptide spacer comprises the hinge region of an IgG molecule or comprises the hinge and $CH_2CH_3$ region of an IgG molecule.

7. The polypeptide of claim 1, wherein the polypeptide further comprises a detection peptide.

8. The polypeptide of claim 1, wherein the anti-TGF-β region binds to soluble TGF-β.

9. An isolated nucleic acid encoding the polypeptide of claim 1.

10. A method for making the polypeptide of claim 1 comprising expressing a nucleotide encoding the polypeptide in a cell.

* * * * *